(12) United States Patent
McAllister et al.

(10) Patent No.: US 10,295,530 B2
(45) Date of Patent: May 21, 2019

(54) FUNCTIONAL ASSAY FOR CANCER RECURRENCE AND MALIGNANT POTENTIAL

(71) Applicant: THE BRIGHAM AND WOMEN'S HOSPITAL, INC., Boston, MA (US)

(72) Inventors: Sandra S. McAllister, Needham, MA (US); Zafira Castano, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 191 days.

(21) Appl. No.: 14/424,948

(22) PCT Filed: Aug. 14, 2013

(86) PCT No.: PCT/US2013/054859
§ 371 (c)(1),
(2) Date: Feb. 27, 2015

(87) PCT Pub. No.: WO2014/035668
PCT Pub. Date: Mar. 6, 2014

(65) Prior Publication Data
US 2015/0212072 A1    Jul. 30, 2015

Related U.S. Application Data

(60) Provisional application No. 61/693,984, filed on Aug. 28, 2012.

(51) Int. Cl.
*G01N 33/50* (2006.01)
*G01N 33/574* (2006.01)
*C12Q 1/6886* (2018.01)

(52) U.S. Cl.
CPC ....... *G01N 33/5091* (2013.01); *C12Q 1/6886* (2013.01); *G01N 33/5011* (2013.01); *G01N 33/574* (2013.01); *G01N 33/57484* (2013.01); *C12Q 2600/158* (2013.01); *G01N 2500/00* (2013.01); *G01N 2800/44* (2013.01); *G01N 2800/52* (2013.01); *G01N 2800/54* (2013.01); *G01N 2800/7028* (2013.01)

(58) Field of Classification Search
CPC ............. G01N 33/574; G01N 33/5011; G01N 33/5091; C12Q 1/6886
See application file for complete search history.

(56) References Cited

U.S. PATENT DOCUMENTS

2011/0206614 A1   8/2011  McAllister et al.

OTHER PUBLICATIONS

Dolznig et al. "Modeling Colon Adenocarcinomas in Vitro: A 3D Co-Culture System Induces Cancer-Relevant Pathways upon Tumor Cell and Stromal Fibroblast Interaction" (Jul. 2011) American Journal of Pathology, vol. 179, No. 1: 487-501.*
Heneweer et al. "Co-culture of Primary Human Mammary Fibroblasts and MCF-7 Cells as an in Vitro Breast Cancer Model" (2005) Toxicology Sciences, vol. 83: 257-263.*
Gottfried et al. "Brave Little World: Spheroids as an in Vitro Model to Study Tumor-Immune-Cell Interactions" (2006), Cell Cycle, vol. 5, No. 7: 691-695.*
Ong et al. "Macrophages in human colorectal cancer are pro-inflammatory and prime T cells towards an anti-tumor type-1 inflammatory response", 2012 (published online Oct. 18, 2011) vol. 42: 89-100.*
Kunz-Schughart et al. "The Use of 3-D Cultures for High-Throughput Screening: The Multicellular Spheroid Model" (2004), Journal of Biomolecular Screening, vol. 9, No. 4: 273-285.*
Green et al. "Chemoattractants Signaling between tumor cells and macrophages regulates cancer cell migration, metastasis and neovascularization" (2009) PLoS One, vol. 4, No. 8: e6713.*
Silzle et al. "Tumor-assocated fibroblasts recruit blood monocytes into tumor tissue" (2003) European Journal of Immunology, vol. 33: 1311-1320.*
Phillips, "The Response of CD24-low/CD44+ Breast Cancer-Initiating Cells to Radiation" (2006) Journal of National Cancer Institute, vol. 98, No. 24: 1777-1785.*
Castano et al. Cancer Discovery. 3(8): 922-935 (2013). "Stromal EGF and IGF-I Together Modulate Plasticity of Disseminated Triple-Negative Breast Tumors.".
Elkabets et al., The Journal fo Clinical Investigation, 121(2):784-799 (2011). "Human tumors instigate granulin-expressing hematopoietic cells that promote malignancy by activating stromal fibroblasts in mice.".
Kaufmann et al., Tissue Eng, 5(6):583-596 Abstract (1999). "Influence of pancreatic islets on growth and differentiation of hepatocytes in co-culture.".
Kuznetsov et al., Cancer Discovery. 2(12): 1150-1165 (2012). Identifcation of Luminal Breast Cancers that Establish a Tumor Supportive Macroenvironment Defined by Pro-Angiogenic Platelets and Bone Marrow Derived Cells.
Lippert et al., International Journal ofMedical Sciences, 8(3):245-253 abstract (2011). "Current Status of Methods to Assess Cancer Drug Resistance.".
McAllister et al., Cell. 133(6):994-1005 (2008)."Systemic endocrine instigation of indolent tumor growth requires osteopontin".
McGowan et al. Mol Cancer Res, 9(7):834-844 (2011). "Notch 1 Inhibition Alters the CDFF hi/CD24lo Population and Reduces the Foormation of Brain Metastases from Breast Cancer.".
Perou et al., Nature 406:747-752 (2000). "Molecular portraits of human breast tumours.".
Tyan et al., Plos ONE, 6(1):e15313 (2011). "Breast Cancer Cells Induce Cancer-Associated Fibroblasts to Secrete Hepatocyte Growth Factor to Enhance Breast Tumorigenesis.".
van't Veer et al., Nature 415:530-536 (2002). "Gene Expression profiling predicts clinical outcome of breats cancer.".

* cited by examiner

*Primary Examiner* — Teresa E Knight
(74) *Attorney, Agent, or Firm* — Nixon Peabody LLP

(57) ABSTRACT

Embodiments herein provides an in vitro co-culture system comprising a population of cancer responder cells and a population of non-tumor cells wherein the cancer responder cells can convert to a malignant state and exhibit hallmark malignant phenotype when the cells are placed in a tumor supportive environment. The system is useful for prognosis evaluation of cancer recurrence, malignancy development, cancer drug screening and surveillance for resistance to cancer drug therapy.

13 Claims, 46 Drawing Sheets

Specification includes a Sequence Listing.

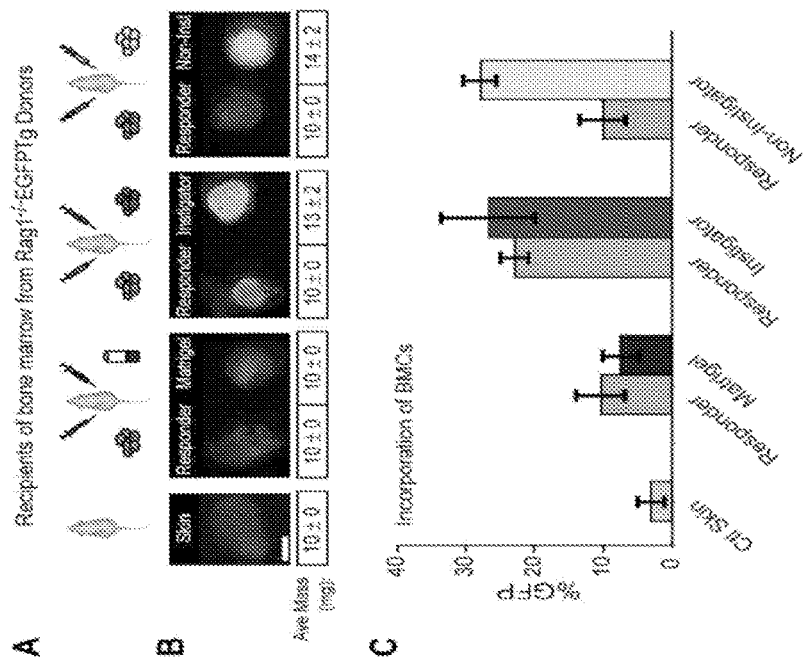
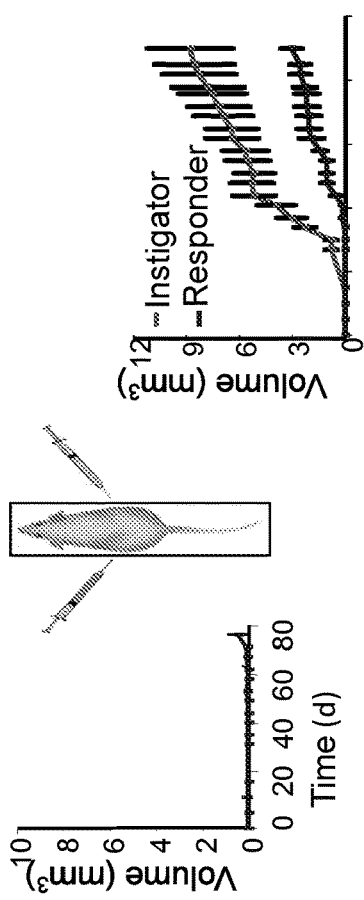
FIGURE 9
FIGURE 10

FIGURE 26, continued

FUNCTIONAL ASSAY FOR CANCER RECURRENCE AND MALIGNANT POTENTIAL

CROSS REFERENCE TO RELATED APPLICATION

This application is a 35 U.S.C. 371 National Stage Application of International Application No. PCT/US2013/054859 filed on Aug. 14, 2013, which designates the United States, and which claims the benefit under 35 U.S.C. § 119(e) of U.S. Provisional Application Ser. No. 61/693,984 filed on Aug. 28, 2012, the contents of each of which are incorporated herein by reference in its entirety.

SEQUENCE LISTING

The instant application contains a Sequence Listing which has been submitted electronically in ASCII format and is hereby incorporated by reference in its entirety. Said ASCII copy, created on Jan. 31, 2018, is named 043214-075232-US_SL.txt and is 10,291 bytes in size.

FIELD

The assays and methods relate to cancer recurrence, malignancy development, cancer drug screening and surveillance for resistance to cancer drug therapy.

BACKGROUND

Breast cancer is a heterogeneous disease that is categorized into molecular and histopathological subtypes based predominantly on analysis of hormone and growth factor receptors—namely estrogen (ER), progesterone (PR), and HER2/Erbb2 (Her2). Women with triple-negative breast cancer (TNBC; i.e. ER−/PR−/Her2−) are at the greatest risk of early recurrence. Luminal breast cancers (LBC), which often include ER+ tumors, are the most prevalent form of breast cancer. These tumors are often differentiated and associated with good prognosis, yet some patients with LBC experience recurrent disease even 15-20 years after their initial diagnosis and surgery. Although classification into these categories has some correlation with patient outcome, it is difficult to accurately predict which patients will relapse. Furthermore, there is no correlation between molecular classification and patient response to current treatment therapies.

In some patients with metastatic breast cancer, tumor cells clearly disseminate prior to surgery, but remain undetected for protracted periods of time before the patient becomes symptomatic. Incipient primary tumors and second primary tumors can also exist in a state of indolence before being detected. For example, autopsy studies of people without a medical history of cancer revealed that indolent cancers are highly prevalent within the general population. What causes indolent tumors to erupt into overt disease is unknown, making it difficult to predict which cancer patients are likely to relapse or to benefit from preemptive therapy.

The systemic environment is appreciated as an important determinant of tumor malignancy and progression. It was previously established that indolent cancer cells ("responders") that are disseminated to various anatomical locations within host mice can be stimulated to form malignant tumors as a consequence of aggressively growing triple-negative breast tumors, luminal breast cancer tumors and colon tumor samples located at distant anatomical sites. These tumors are seen as "instigators" or inducers of the transformation and conversion of the indolent cancer responder cells to form malignant tumors. A growing body of evidence supports the notion that tumors that co-exist within a patient who has multiple tumor burden (e.g., multiple disseminated metastases) can interact systemically to modulate overall cancer progression. Responding tumor outgrowth occurs as a consequence of systemically-acting cytokines and bone marrow derived cells that are rendered pro-tumorigenic by the instigating triple-negative breast tumors. This cascade of events, termed "systemic instigation", results in the outgrowth of highly desmoplastic, malignant tumors. A deeper understanding of systemic tumor-promoting processes should improve identification of patients who would benefit from adjuvant therapy.

SUMMARY

The technology described herein is based on the discovery of an in vitro co-culture assay comprising two populations of cells that enables one to determine whether there are cells and/or factors in a cancer patient that support the further development of malignant cancers from otherwise quiescent, indolent cancer cells. The two populations of cells are the non-tumor cells derived from the cancer patient and indolent cancer cells, cells that have not acquire a malignant phenotype yet but are capable when provided with a malignant supportive environment. The non-tumor cells derived from the cancer patient provide the malignant supportive environment for the indolent cancer cells in order to convert to a malignant state. When the indolent cancer cells convert to the malignant state, the indolent cancer cells manifest a number of malignant phenotypes such as the ability to proliferation on soft agar, the ability to grow in suspension (i.e., loss of contact inhibition), the ability to grow in any standard 3-dimensional culture conditions, the ability to proliferate and form tumor in vitro, the expression of malignancy markers, the acquisition of cancer stem cell markers, the ability to proliferate faster, and the acquisition of expression of genes associated with poor prognosis in cancer patients.

Such an in vitro cell culture assay can be useful for diagnosing/prognosing the likelihood that a cancer patient would develop malignant cancer/tumor in the future, for determining whether a cancer patient has any quiescent, indolent cancer cells that can convert to malignant cancer cells when provided with a malignant supportive environment, for determining whether there are fibroblast cells that contribute to the creation of a malignant supportive environment in a cancer patient, for screening of drugs/agents/compounds that can inhibit the "indolent conversion to malignant" process, and for surveillance for resistance to cancer drug therapy.

Accordingly, embodiments herein provides an in vitro co-culture system comprising a population of cancer responder cells and a population of non-tumor cells wherein the cancer responder cells can convert to a malignant state and exhibit hallmarks of the malignant phenotypes when the cells are placed in a tumor supportive environment. The system is useful for prognosis evaluation of cancer recurrence, malignancy development, cancer drug screening and surveillance for resistance to cancer drug therapy.

In one embodiment, provided herein is an assay comprising in vitro co-culturing a population of cancer responder cells with a population of non-tumor cells; and measuring for at least one malignant phenotype exhibited by the cancer responder cells. Depending on the source and types of cancer responder cells and of non-tumor cells used, this assay can be adapted for prognosis evaluation of cancer recurrence, malignancy development, cancer drug screening and surveillance for resistance to cancer drug therapy.

In one embodiment, provided herein is an assay comprising in vitro co-culturing a population of cancer responder cells with a population of non-tumor cells, wherein the non-tumor cells are obtained from a subject who has been diagnosed with cancer; and measuring a malignant phenotype exhibited by the cancer responder cells. In one embodiment of this assay, the cancer responder cells are standard positive responder cells. In one embodiment, this assay is useful for prognosis evaluation of cancer recurrence.

In one embodiment, provided herein is an assay comprising in vitro co-culturing (i) a population of cancer responder cells obtained from a subject who has been diagnosed with cancer with (ii) a population of non-tumor cells, the non-tumor cells having a capability to induce indolent cancer responder cells to convert to a malignant state when the non-tumor cells are co-cultured with indolent cancer responder cells; and measuring a malignant phenotype exhibited by the cancer responder cells. In one embodiment of this assay, the non-tumor cells are standard positive non-tumor cells known to provide a tumor supportive environment. In one embodiment, this assay is useful for determining whether a cancer patient has quiescent, indolent cancer cells that can convert to malignant cancer cells when provided with a malignant supportive environment.

In one embodiment, provided herein is an assay comprising in vitro co-culturing a population of cancer responder cells with a population of non-tumor cells; contacting the co-culture with at least one agent or compound; and measuring for at least one malignant phenotype exhibited by the cancer responder cells. In one embodiment, this assay is useful for screening of drugs/agents/compounds that can inhibit the "indolent conversion to malignant" process.

In one embodiment of any assay described, the cancer responder cells are selected from a group consisting of defined cancer responder cell lines, primary cancer/tumor cells, or circulating cancer cells. In one embodiment, the defined cancer responder cell lines are standard positive responder cells.

In one embodiment of any assay described, the non-tumor cells are selected from the group consisting of bone marrow-derived circulating cells, bone marrow-aspirated cells, buffy coat cells, peripheral circulating cells, and immune cells. In one embodiment, the non-tumor cells standard positive non-tumor cells known to provide a tumor supportive environment.

In one embodiment of any assay described, the at least one malignant phenotype measured is selected from the group consisting of the ability to proliferation on soft agar, the ability to form colonies ion soft agar, the ability to acquire the expression of genes associated with poor prognosis in cancer patients, the expression of malignancy markers, the acquisition of cancer stem cells markers and/or and form tumor in vitro, the ability to proliferate faster and form tumors in vivo, the ability to proliferate and form tumor in vitro, the expression of malignancy markers, and the expression of cancer stem cell markers.

In one embodiment of any assay described, the assay further comprises co-culturing the populations of cancer responder cells and non-tumor cells in the presence of plasma or platelets or exosomes. In one embodiment, the plasma or platelets or exosomes are obtained from the subject diagnosed with cancer. In one embodiment, the plasma or platelets or exosomes are standard positive plasma or platelets or exosomes known to provide a tumor supportive environment. In one embodiment, the standard positive plasma or platelets or exosomes provides a tumor supportive environment together with standard positive non-tumor cells.

In one embodiment of any assay described, the assay further comprises co-culturing the populations of responder cells and non-tumor cells with a population of fibroblast cells. In one embodiment, this assay is useful for determining whether there are fibroblast cells that contribute to a malignant supportive environment in a cancer patient.

In one embodiment of any assay described, the population of fibroblast cells is obtained from a healthy, cancer-free tissue from a subject.

In another embodiment of any assay described, the population of fibroblast cells is obtained from a cancer tumor tissue excised from a subject.

In one embodiment of any assay described, the population of fibroblast cells is separated by a membrane from the population of cancer responder cells and the population of non-tumor cells in the co-culture.

In one embodiment of any assay described, the assay further comprises contacting the co-culture with at least a test agent or compound. For example, a test agent or compound that can inhibit the conversion of the cancer responder cells to the malignant state.

In one embodiment of any assay described, the population of cancer responder cells is selected from HME, HMLE, HMLER hygro-H-rasV12 (HMLER-HR), HMLER-puro-H rasV12, BPE, BPLER, BT-549, and MCF7, MCF7-Ras human breast tumor cells. These are examples are defined cancer responder cell lines and are also examples of standard positive responder cells.

In one embodiment of any assay described, the cancer responder cells are in an indolent state.

In one embodiment of any assay described, when the cancer responder cells exhibit an increase expression of any one of the following: Oct4, Oct4A, c-Myc, Zeb1, osteopontin, EGFR and IGF-1R, CD24, phospho-STAT3, or there is an increase in the number of CD44hi+/CD24low− cells indicates that the cancer responder cells exhibit a malignant phenotype.

In one embodiment of any assay described, when the cancer responder cells exhibit an increased expression of any one of the following: CD24, or there is an increased in CD44hi+/CD24low− cells indicates that the responder cells exhibit a malignant phenotype.

In one embodiment of any assay described, the non-tumor cells are obtained from a bone marrow aspirate, a bone marrow biopsy, a spleen biopsy, a lymph node aspirate or biopsy, a blood sample, the non-tumor portion of a cancer from a subject.

In one embodiment of any assay described, the non-tumor cells are selected from the group consisting of bone marrow-derived circulating cells, spleen-derived cells, lymph node-derived cells, buffy coat cells, peripheral blood circulating cells, and immune cells.

In one embodiment of any assay described, the subject has been diagnosed with triple-negative breast cancer (TNBC) or luminal breast cancer (LBC) or Her2+ breast cancer.

In one embodiment of any assay described, the subject has undergone breast reduction mammoplasty, breast biopsy, breast lumpectomy, partial mastectomy or total mastectomy.

In one embodiment of any assay described, the subject has undergone bone marrow cell mobilization therapy, bone marrow transplantation, immune-suppression therapy, non-steroidal anti-inflammatory therapy, anti-oxidant therapy, radiation therapy, chemotherapy, hormone therapy and/or targeted therapy or treated with placebo.

In one embodiment of any assay described, the assay further comprises selecting a subject who has been diagnosed with cancer.

In one embodiment of any assay described, the assay further comprises providing a sample of bone marrow, a sample of bone marrows-derived cells, a blood sample, a sample of spleen-derived cells, a sample of lymph node-derived cells, a healthy breast tissue sample, and/or a cancer tissue from the subject.

In one embodiment of any assay described, the assay further comprises diagnosing that the subject likely has malignant tumor supportive cells and/or factors and/or fibroblast when the cancer responder cells exhibition of at least one malignant phenotype when the assay uses non-tumor cells that are derived from the subject diagnosed with cancer.

In one embodiment of any assay described, the assay further comprises diagnosing that the subject likely to developed malignant cancer when the cancer responder cells exhibit of at least one malignant phenotype when the assay uses non-tumor cells that are derived from the subject diagnosed with cancer.

In one embodiment of any assay described, the assay further comprises diagnosing that the subject likely has indolent cancer responder cells capable of converting to malignant tumor when the cancer responder cells exhibit of at least one malignant phenotype when the assay uses cancer responder cells that are derived from the subject diagnosed with cancer.

In one embodiment of any assay described, the non-tumor cells have a capability to induce indolent cancer responder cells to convert to a malignant state when the non-tumor cells are co-cultured with indolent cancer responder cells.

In one embodiment of any assay described, the cancer responder cells are indolent but will convert to a malignant state when the non-tumor cells that have a capability to induce indolent cancer responder cells to convert to a malignant state are present.

In one embodiment of any assay described, the assay further comprises determining that the at least one agent or compound added to the co-culture likely has a capability of inhibiting or blocking the conversion of cancer responder cells to a malignant state when the cancer responder cells in the co-culture exhibit at least one less malignant phenotype or at least a reduced or decreased malignant phenotype compared to in the absence of the at least one agent or compound.

In one embodiment, provided herein is an assay comprising performing a first co-culture comprising in vitro co-culturing a population of cancer responder cells with a population of non-tumor cells obtained from a subject at a first time point, wherein the cancer responder cells are indolent but capable of converting to a malignant, and wherein the subject has been diagnosed with cancer; contacting the co-culture with at least one anti-cancer therapeutic agent or compound that is currently being used to treat the cancer in the subject; and measuring for at least one malignant phenotype exhibited by the cancer responder cells; performing a second co-culture comprising in vitro co-culturing a population of cancer responder cells with a population of non-tumor cells obtained from a subject at a second time point, wherein the cancer responder cells are the same cells as used in the first co-culture; contacting the second co-culture with the at least one anti-cancer therapeutic agent or compound used in the first co-culture; and measuring for at least one malignant phenotype exhibited by the cancer responder cells; and comparing the malignant phenotype exhibited by the cancer responder cells of the first and second co-cultures. This assay is useful for surveillance for resistance to cancer drug therapy.

In one embodiment, the assay further comprising determining that the subject has developed resistance to the at least one anti-cancer therapeutic agent or compound currently being used to treat the cancer when the cancer responder cells in the co-culture exhibit at least one additional malignant phenotype or at least an increased malignant phenotype in the second co-culture compared to the first co-culture.

In one embodiment, the assay further comprises determining that the at least one agent or compound currently being used to treat the cancer is still effective against the cancer when the cancer responder cells in the second co-culture exhibit no additional malignant phenotype or at least an increased malignant phenotype compared to the first co-culture.

In one embodiment, provided herein is an in vitro method for surveillance of cancer recurrence in a subject comprising: (a) providing a biological sample at a first time point and a second time point, the biological samples are from a subject who has previously been diagnosed with cancer, wherein the second time point is after the first time point and both time points are after the subject has been diagnosed with cancer; conducting the in vitro co-culture assay described herein; and comparing the measurement of the malignant phenotype of the cancer responder cells in the assay of step b for the second time point with that of the first time point. In one embodiment of this assay, the cancer responder cells used in the assay is a standard positive responder cells and the non-tumor cells are obtained from the subject at the first and second time point.

In one embodiment of the method, the cancer responder cells of the two time points do not exhibit a malignant phenotype indicate that there is unlikely cancer recurrence and the cancer is in remission.

In one embodiment of the method, when the cancer responder cells of the first time point do not exhibit a malignant phenotype but the cancer responder cells of the second time point do exhibit a malignant phenotype indicate that there is likely cancer recurrence in the subject.

In one embodiment of any method described, the method further comprises treating the subject when it is observed that the cancer responder cells at the second time point exhibit a malignant phenotype.

In one embodiment, provided herein is a kit comprising a cell culture of a population of cancer responder cells for diagnosing the likelihood of cancer recurrence in a subject or for determining the likelihood of development of cancer drug resistance in a subject. In one embodiment of the kit, the cancer responder cells are standard positive responder cells.

In one embodiment of the kit, the cancer responder cells are selected from HME, HMLE, HMLER hygro-H-rasV12 (HMLER-HR), HMLER-puro-H rasV12, BPE, BPLER, BT-549, and MCF7, MCF7-Ras human breast tumor cells.

In one embodiment of the kit, the kit further comprises a population of positive control non-tumor cells capable of inducing the cancer responder cells to exhibit a malignant phenotype in an assay of described herein.

In one embodiment, provided herein is an assay comprising co-culturing a population of breast cancer responder cells with a population of bone marrow derived-cells (BMCs) obtained from a subject who has been diagnosed with breast cancer; and measuring for at least a malignant phenotype exhibited by the breast cancer responder cells. In other embodiments, any other non-tumor cells obtained from a subject who has been diagnosed with breast cancer can be used for the assay.

In one embodiment, the assay further comprises co-culturing the populations of breast cancer responder cells and BMCs in the presence of plasma or platelets or exosomes derived from the subject.

In one embodiment, the assay further comprises comprising co-culturing the populations of responder cells and BMCs with a population of fibroblast cells derived from the subject. In one embodiment, the population of fibroblast cells is obtained from a healthy, cancer-free breast tissue from the subject. In another embodiment, the population of fibroblast cells is obtained from a breast cancer tumor tissue excised from the subject.

In one embodiment, the population of fibroblast cells is separated by a membrane from the population of breast cancer responder cells and the population of BMCs in the co-culture. In one embodiment, the membrane is semi-pemeable and cell-impeameable.

In one embodiment, the population of breast cancer responder cells are selected from HME, HMLE, HMLER hygro-H-rasV12 (HMLER-HR), HMLER-puro-H rasV12, BPE, BPLER, BT-549, and MCF7, MCF7-Ras human breast tumor cells.

In one embodiment, the population of breast cancer responder cells is in an indolent state.

In one embodiment, the subject has been diagnosed with triple-negative breast cancer (TNBC) or luminal breast cancer (LBC) or Her2+ breast cancer.

In one embodiment, when the diagnosed breast cancer is TNBC and the population of breast cancer responder cells exhibit an increase expression of any one of the following: Oct4, Oct4A, c-Myc, Zeb1, osteopontin, EGFR and IGF-1R, or there is an increased in CD44hi+/CD24low− cells indicates that the breast cancer responder cells exhibit a malignant phenotype, and it is highly likely that the subject would have cancer recurrence.

In one embodiment, when the diagnosed breast cancer is LBC and the population of breast cancer responder cells exhibit an increase expression of any one of the following: CD24, or there is an increased in CD44hi+/CD24low− cells indicates that the breast cancer responder cells exhibit a malignant phenotype, and it is highly likely that the subject would have cancer recurrence.

In one embodiment of any assay described, the subject has undergone reduction mammoplasty, biopsy, breast lumpectomy, partial mastectomy or total mastectomy.

In one embodiment of any assay described, the subject has bone marrow cell mobilization therapy, bone marrow transplantation, immune-suppression therapy, non-steroidal anti-inflammatory therapy, anti-oxidant therapy, radiation therapy, chemotherapy, hormone therapy and/or targeted therapy or treated with placebo.

In one embodiment of any assay described, the assay further comprises selecting a subject who has been diagnosed with breast cancer.

In one embodiment of any assay described, the assay further comprises providing a sample of bone marrow, a sample of bone marrow derived cells, a blood sample, a healthy breast tissue sample, and/or a breast cancer tissue from the subject.

In one embodiment, provided herein is an in vitro method for surveillance of breast cancer recurrence in a subject comprising providing a biological sample at a first time point and a second time point, the biological samples are from a subject who has previously been diagnosed with breast cancer, wherein the second time point is after the first time point and both time points are after the subject has been diagnosed with breast cancer; conducting an assay comprising a co-culture described herein; and comparing the measurement of the malignant phenotype of the responder breast cancer cells in the co-culture assay described in the second time point with that of the first time point. In one embodiment of this assay, the cancer responder cells used in the assay is a standard positive responder cells and the non-tumor cells are obtained from the subject at the first and second time point.

In one embodiment, when the breast cancer responder cells of the two time points do not exhibit a malignant phenotype indicate that there is unlikely cancer recurrence and the cancer is in remission.

In one embodiment, when the breast cancer responder cells of the first time point do not exhibit a malignant phenotype but the breast cancer responder cells of the second time point do exhibit a malignant phenotype indicate that there is likely cancer recurrence in the subject.

In one embodiment, the method further comprises treating the subject when it is observed that the breast cancer responder cells at the second time point exhibit a malignant phenotype.

BRIEF DESCRIPTION OF THE DRAWINGS

FIG. 9 shows that an in vivo binary tumor xenograft model—mammary carcinoma.

FIGS. 10A-10C show that bone marrow-derived cells are incorporated into responding tumor stroma.

FIG. 18A. Scheme of bilateral human tumor xenograft implantation system used for data represented in figure.

FIG. 18B. Growth kinetics of responding tumor cells exposed to the systemic environments established by control MATRIGEL (n=6), triple-negative breast cancer (TNBC; n=4), or luminal breast cancer (LBC; n=3); data represented only for cases in which the contralateral instigating tumors grew.

FIG. 18C. Hematoxylin and eosin (H&E) stains of responding tumors resulting from exposure to indicated environments; arrows indicate mitotic tumor cells.

FIG. 18D. Quantification of the malignancy profile factors in responding tumor cells under indicated conditions. The number of cells stained positively for indicated factors is represented as a percentage of the total number of DAPI-positive cells per random field; 3 fields per tumor (n=6 Matrigel; n=12 TNBC; n=6 LBC). Cytokeratins (CK) 14 (basal) and 18 (luminal); factors that mediate maintenance of pluripotency (Oct4 and c-Myc), and features of the epithelial-mesenchymal transition (Zeb1).

FIG. 19A. Experimental scheme used for data represented in figure.

FIG. 19B. Final mass of responder tissues after 8 days of exposure to the Matrigel or TNBC environments. Differences were not significant (n.s.). Data to right of dashed line represent mass of TNBC instigators after 5 weeks of growth. Incidence of tumor formation is shown above data bars (n=33 mice per group).

FIG. 19C. Scheme of responding tumor subfractionation into GFP+ responding tumor cell and GFP-negative stromal cell constituents.

FIG. 19D. qPCR expression levels of indicated malignancy profile genes in GFP+ responder tumor cells that had grown in TNBC environments relative to those from control MATRIGEL environments. Average from 3 independent experiments; samples run in triplicate for each experiment.

FIG. 20A. Scheme of responding tumor transplantation system used for data represented in figure.

FIG. 20B. Mass of responding tumors 36 d following their surgical transplantation into secondary hosts bearing either Matrigel or TNBC systemic environments. Incidence of tumor formation is shown above data bars (n=3 mice per group); differences were not statistically significant (n.s.).

FIG. 20C. Graph represents number of Ki67+ cells as a percentage of the total number of cells per field; n=6 Matrigel images; n=9 TNBC images.

FIG. 20D. Hematoxylin and eosin (H&E) stains of responder tumors that had been transplanted into indicated secondary environments; scale bar=50 pm.

FIG. 20E. Quantification of transplanted responding tumors stained for the indicated malignancy profile factors (n=6 MATRIGEL images; n=9 TNBC images).

FIG. 21A. Scheme of tumor subfractionation into GFP+ responding tumor cell and GFP-negative stromal cell constituents after 8 days of exposure to either Mg or TNBC systemic environments.

FIG. 21B. Heat map representing expression levels of indicated genes in the GFP-negative sorted cells from the TNBC-induced stroma relative to the control stroma.

FIG. 21C. Photomicrograph of agarose gel to visualize indicated Q-PCR products; RNA prepared from GFP-negative stromal cell after 8 days of exposure to either Mg or TNBC systemic environment.

FIG. 21D. EGF and IGF-1 expression levels in BMC-TNBC relative to those BMC-C (n=6 per group).

FIG. 21E. Scheme of in vitro co-culture experiments with GFP-positive responder tumor cells and bone marrow cells from mice bearing: Matrigel control (BMC-C), or triple-negative breast cancers (BMC-TNBC).

FIG. 21F. Flow cytometric density plots for CD441CD24 expression on responder tumor cells following indicated co-culture conditions; numbers represent values for specific sample represented. Graph represents quantification of CD44+1CD24− expression on responding tumor cells under indicated co-culture conditions relative to that under control conditions.

FIG. 21G. Gene expression levels in GFP+ responder tumor cells that had grown in co-culture for 4 days with BMC-TNBC relative to those under identical co-culture conditions with BMC-C, as determine by qRT-PCR.

FIG. 21H. Experimental scheme for implantation of BMC/responding tumor cell admixtures.

FIG. 21I. Graph represents mass of responding tumors 12 weeks following injection of indicated BMC admixtures (n=10 tumors per group).

FIG. 21J. Quantification of malignancy profile factors in responding tumor cells under indicated conditions. The number of cells stained positively for each of the indicated factors is represented as a percentage of the total number of DAPI-positive tumor cells per random field (n=9 fields per group; 3 images quantified from each of 3 tumors per group).

FIG. 22A. Scheme of human breast cancer surgical tumor specimen instigation system. Samples from 2 different patients with TNBC (hBrCa TNBC-I and hBrCa TNBC-II) and patient with LBC (hBrCa LBC) were implanted in equal portions into 3 mice per cohort. HMLER-HR responder cells were injected contralateraly 20 days later and analyzed after 8 days of instigation.

FIG. 22B. Representative merged immunofluorescent images of responding tumors exposed to environments established by indicated human breast cancer surgical specimens. Tumors were stained for: indicated malignancy profile factors, LgT Antigen (expressed only by responder cells), and phosphorylated (activated) forms of the IGF (P-IGF/IR) and EGF (P-EGFR) receptors.

FIG. 22C. Expression of malignancy profile factors in responding tumor cells under indicated conditions. The number of cells stained positively for each of the indicated factors is represented as a percentage of the total number of DAPI-positive nuclei or LgT-positive (indicated) responder tumor cells per field. A minimum of 3 fields were quantified per tumor for each group; n=6 fields for Mg control environment (Env), n=9 fields TNBC-I Env, n=9 fields TNBC-11 Env, n=6 fields LBC Env.

FIG. 23A. Flow cytometric density plots representing CD441CD24 profiles of responding tumor cells after 4 days in complete medium, C.M, or in C.M. depleted of the indicated growth factors. Graph represents average responding tumor cell CD44/CD24 profiles under indicated conditions relative to that of C.M (samples run in triplicate).

FIG. 23B. Expression levels of indicated malignancy profile genes in responder tumor cells after 4 days in indicated culture conditions relative to those in C.M. n=6; each sample run in duplicate in 3 separate experiments.

FIG. 23C. Soft agar colonies formed by responder tumor cells in the presence of C.M. or the indicated depleted conditions. Data represent average of three independent experiments, where each condition was assessed in triplicate.

FIG. 23D. Flow cytometric density plots representing CD44/CD24 profiles of responding tumor cells after 4 days in depleted medium, D.M. (medium devoid of EGF and insulin), or D.M.+indicated supplements. Graph represents average responding tumor cell CD441CD24 profiles under indicated conditions relative to that of C.M (samples run in triplicate).

FIG. 23E. Expression levels of indicated malignancy profile genes in responder tumor cells after 4 days in indicated culture conditions relative to those maintained in C.M. Data represent average of three independent experiments, where each sample was run in triplicate.

FIG. 23F. Model representing interconversion of responsive tumor cells between malignant and indolent states in response to EGF and insulin signaling.

FIG. 23G. Expression levels of indicated malignancy profile genes in responder tumor cells (HMLER-HR and BT549) after 4 days in indicated culture conditions relative to those in depleted medium (D.M.).

FIG. 23H. Expression levels of indicated malignancy profile genes in responder tumor cells (HMLER-HR) after 4 days in indicated culture conditions relative to those maintained in completed media (C.M.). n=6; each sample run in duplicate in 3 separate experiments.

FIG. 23I. Experimental scheme for ligand bioavailability and depletion experiments.

FIG. 23J. Left graph: Number of soft agar colonies formed by responder HMLER-HR tumor cells in the presence of their standard medium (S.M.) or S.M. devoid of the indicated growth factors: insulin (Ins), epidermal growth factor (EGF), or hydrocortisone (Hydr). Data represent average of 2 independent experiments, where each condition was assessed in triplicate (n=6). Right graph: Number of colonies formed by responding BT549 tumor cells cultured in soft agar in either depleted medium (D.M.) or D.M. with epidermal growth factor (EGF) (n=3). Table indicates phosphorylation status of EGFR and IGF1R under each condition.

FIG. 24A. Scheme of pharmacological targeting of TNBC systemic instigation for data represented in figure. Mice were treated with vehicle DMSO or both the EGFR inhibitor (erlotinib; dose 100 mg/kg/day) and IGFR inhibitor (BMS-754807; dose 50 mg/kg/day) every day for eight days by oral gavage.

FIG. 24B) Mass of responder tumor/tissue plugs after 8 days of exposure to indicated environments, with indicated drug or control treatment. Incidence of tumor formation is shown above data bars (n=5 mice per group). Differences were not significant (n.s.).

FIG. 24C. Quantification of Ki67+ cells as a percentage of the total number of LgT+ responder cells per field (n=9; 3 random fields for each of 3 tumors per group).

FIG. 24D. Quantification of malignancy profile factors in responding tumor cells under indicated conditions. The number of cells stained positively for each of the indicated factors is represented as a percentage of the total number of DAPI-positive nuclei or LgT-positive (indicated) tumor cells (n=9; 3 random fields for each of 3 tumors per group).

FIG. 25A. Final mass of responder BT549 tissues after 8 days of exposure to the MATRIGEL or TNBC environments (short-term instigation described in FIG. 19A). Incidence of tumor formation is shown above data bars; differences were not significant.

FIG. 25B. Graph data obtained from BT549 responding tumors stained for the proliferation marker Ki67, and cell nuclei, the tumors were under control or TNBC environment conditions. Graph represents number of Ki67+ cells as a percentage of the total number of cells per field; n=9; 3 random fields from 3 tumors per group.

FIG. 25C. Graph represent the number of BT549 responding tumor cells stained positively for each of the indicated factors as a percentage of the total number of DAPI-positive nuclei or human-Mitochondria (hMit), as indicated; n=9; 3 random fields from 3 tumors per group of MATRIGEL (Mg) or TNBC environments (short-term instigation).

FIG. 25D. Growth kinetics of BT549 responding tumor cells during a 40 day time course of exposure to the systemic environments established by control MATRIGEL or triple-negative breast cancer (TNBC) (long-term instigation described in FIG. 18A). Data represented only for cases in which the contralateral instigating tumors grew. Incidence of tumor formation is shown next to data lines.

FIG. 25E. Representative flow cytometric density plots for CD44/CD24 (left) and IGFR/EGFR (right) expression on BT549 responder tumor cells in culture.

FIG. 25F. Expression of EGF, and IGF-1 in the responder BT549 cells relative to that of HMLER-HR responding tumor cells. Data are expressed as mean±SEM; samples tested in triplicate.

FIGS. 26A-26E. Paracrine Activation of EGF and IGF/Insulin Receptors, in pro-tumorigenic BMCs, is a consequence of TNBC instigation.

FIG. 26A. Combined heat map showing the most variable individual genes based on our criteria (see Methods) for analysis of responding HMLER-HR tumor microenvironmental components: cancer-associated fibroblasts isolated from human mammary tumor xenografts (CAF) and granulin-treated human mammary fibroblasts (PGRN) relative to PBS-treated human mammary fibroblast controls (CTRL) (GEO GSE25620); and pro-tumorigenic BMCs from mice bearing instigating TNBC-BPLER tumors (instigator) relative to matrigel controls (matrigel) (GEO GSE25619)). Genes are ranked by differential expression of CAF vs CTRL (See Methods).

FIG. 26B. Flow cytometry density plots representing the EGFR/IGFR profile of responding tumor cells and instigating TNBC-BPLER cells in culture.

FIG. 26C. Expression of EGF and IGF1 in the instigating TNBC cells (Inst) relative to that of responding tumor cells HMLER-HR (Resp). Data are expressed as mean±SEM. Results represent the average from three independent experiments. *, p<0.05, **, p<0.01. Inset represents ciPCR products run in 2% agarose gel.

FIG. 26D. Photomicrograph of agarose gel to visualize indicate Q-PCR products. mRNA prepared from BMC-TNBC and BMC-C.

FIG. 26E. Expression levels of c-myc in HMLER-HR responding tumor cells after 4 days in response to indicated doses of EGF. Data are represented relative to cells that had been maintained in depleted medium (D.M.; medium devoid of EGF and insulin). Data are expressed as mean±SEM; samples tested in triplicate.

FIG. 28A. Representative photomicrographs of responding tumor cell cultures in soft agar in the presence of complete medium or complete medium devoid of the indicated growth factors: insulin (Ins), epidermal growth factor (EGF). Depletion of hydrocortisone (Hydro) was also tested for its effects on tumorigenicity and was found to have no effect (see FIG. 23C). The TNBC instigator is shown as a positive control.

FIG. 28B. Gene expression profile of responder tumor cells growing in vivo in either control MATRIGEL (Mg) or TNBC environments, relative to responder cells from culture, prior to injection. Data are expressed as mean±SEM. p values on the top of data bars represent student's t-test when comparing cells from the tumor to those in culture. p values indicated as connectors represent the student's t-test when comparing responding tumor cells from tumors in the MATRIGEL environment to those in the TNBC environment.

FIG. 28C. Left graph: Number of soft agar colonies formed by responder HMLER-HR tumor cells in the presence of their standard medium (S.M.) or S.M. devoid of the indicated growth factors: insulin (Ins), epidermal growth factor (EGF), or hydrocortisone (Hydr). Data represent average of 2 independent experiments, where each condition was assessed in triplicate (n=6). Right graph: Number of colonies formed by responder BT549 tumor cells cultured in soft agar in either depleted medium (D.M.) or D.M. with epidermal growth factor (EGF) (n=3). Table indicates phosphorylation status of EGFR and IGF1R under each condition.

FIG. 28D. Responder HMLER cells were cultured in the presence of the indicated growth factors for 4 days. Cell viability was determined based on absorbance at 450 nm (Abs) in a standard MTT assay (n=5), and apoptosis was based on analysis of 10,000 total events by flow cytometry based on propidium iodide (PI) incorporation (n=2). Cells treated with detergent for 1 minute served as positive control.

FIG. 28E. Responder BT549 cells were cultured in the presence of the indicated growth factors for 4 days. Cell viability was determined based on absorbance at 450 nm (Abs) in a standard MTT assay (n=5). Data represent the mean±s.e.m.; p values were obtained by Student's t-test.

FIG. 30A shows the systemic instigation human tumor xenograft model. Aggressively growing "Instigating" human tumors or controls are injected into one site of host Nude mice; otherwise indolent "Responding" human tumor cells injected into distant anatomical locations.

FIG. 30B shows the mass of responding tumors that formed in the systemic environments established by control MATRIGEL, triple-negative breast cancer (TNBC), or luminal breast cancer (LBC). Incidence of responding tumor formation is indicated above each bar; n=4 mice per group.

FIG. 30C shows hematoxylin and eosin (H&E) stains of responding tumors after growth in indicated systemic environments; scale bar=200 μm; inset=100 μm.

FIG. 30D. Staining for the proliferation marker, Ki67 (darker staining) in responding tumors; nuclei counterstained with hematoxylin. Areas of necrosis ("N") and edema ("E") are indicated. Scale bar=100 μm.

FIG. 30E. Average number of vessels per area in indicated tumors and tissues. Vessels were counted under 40× magnification in 3 different areas from each of 3 different tumors per group (n=9 images per group). The two tissue plugs recovered opposite MATRIGEL that did not contain focal tumors were also counted.

FIG. 30F. Results from flow cytometric analysis of GFP+ bone marrow-derived cells recruited into responding tumors in Whole mount fluorescent images (4×) of GFP+BMCs recruited to responding tumors after 4 weeks of exposure to indicated systemic environments; n=4 per group.

FIG. 30G. Flow cytometric analysis of indicated cells in the marrow of mice bearing MATRIGEL control or instigating LBC. Graph represents average fold change in numbers of indicated cell types in bone marrow of mice bearing LBC relative to those bearing MATRIGEL control; n=4 mice per group.

FIG. 32A. Left: representative images of capillary tubes formed by human umbilical vein endothelial cells (HUVECs) after 6 hr exposure to platelet releasates prepared from indicated mice; 4× magnification. Right: Quantification of HUVEC branch points over a 4-7 hour time course (see Methods) induced by platelet releasates from indicated tumor-bearing mice. Mouse and platelet status indicated below graph; n=3 samples per group, tested in duplicate.

FIG. 32B. Left: representative 4× images of capillary tubes formed by HUVECs after 7 hr exposure to 48-hr conditioned medium (CM) from indicated cell lines. Right: Quantification of HUVEC branch points over a 4-7 hour time course (see Methods) induced by CM from indicated cell lines. Releasates from resting mouse or human platelets were used as controls. All samples analyzed in duplicate.

FIG. 32C. Assay to test ability of platelets to absorb pro-angiogenic factors from CM of indicated cell lines. 48-hour CM was collected from LBC instigator cells or responder cells and exposed to naïve platelets from cancer-free humans or mice for 10 min at 37° C. Various media (1A-2B) were tested for ability to induce angiogenesis in the HUVEC assay.

FIG. 32D. Relative number of capillary tube branch points induced by CM from (C). HUVECs were subjected in vitro to indicated CM and the number of branch points quantified during a 4-7 hour time course. Data represent relative number of branch points: 1B/1A for resting naïve mouse and human platelets and 2A/2B for resting naïve mouse platelets. All samples were tested in duplicate.

FIG. 32E. Relative levels of indicated cytokines in platelet lysates from mice bearing MATRIGEL or LBC tumors; n=3 mice per group. Significant values: GRO (p=0.012), IFNγ (p=0.050), IL6 (p=0.044), PDGF-BB (p=0.033), and PlGF (p=0.044).

FIG. 33A. In vivo test of BMC tumor promoting function. BMCs harvested from mice bearing indicated systemic environments were immediately mixed with responder cells and injected subcutaneously into secondary recipients.

FIG. 33B. Tumor mass 12 wk following injection of responder cells admixed with indicated BMCs. Numbers of mice and incidence of tumor formation indicated below graph for collective data from 2 separate experiments.

FIG. 33C. Vessel density in indicated responding tumors; differences were not significant (n.s.).

FIG. 33D. Representative flow cytometry histograms of CD24 expression on GFP+ responder cells after 4 d in vitro co-culture with BMCs harvested from indicated mice. Gate represents CD24+ populations. Graph represents percent change in responding tumor cell CD24 surface expression under indicated conditions relative to co-culture with BMCs from cancer-free mice; n=10 BMC samples per group.

FIG. 34A. Human luminal breast tumor (hBRCA-LBC) xenotransplantation model. Each of 4 surgical specimens (hBRCA-LBC1 through 4) was implanted into 3 mice per cohort.

FIG. 34B. Growth of responding tumors in environment established by hBRCA-LBC1 tumor specimens; n=3 mice. Inset: Ki67 (darker areas) of responding tumor formed in the hBRCA-LBC1 environment; nuclei counterstained with hematoxylin.

FIG. 34C. Microvessel density of responding tumors in indicated hBRCA-LBC tumor environments. Tumors were examined under 40× magnification and 3 representative areas per tumor were analyzed; n=3 tumors (9 images) for MATRIGEL, n=3 tumors (9 images) for hBRCA-LBC1, n=1 tumor (3 images) for hBRCA-LBC2, no tumors were recovered opposite hBRCA-LBC3 or hBRCA-LBC4.

FIG. 34D. Xenotransplantation model for responding human primary LBC (hBRCA-LBC 5); n=5 mice per group.

FIG. 34E. Growth kinetics of hBRCA-LBC5 implanted into either control MATRIGEL (blackline) or LBC (grey line) systemic environments.

FIG. 34F. hBRCA-LBC 5 vessel density in tumors recovered from indicated environments. Tumors were examined under 40× magnification and 5 representative areas per tumor were analyzed.

FIG. 34G. Human clear cell renal cell carcinoma (cRCC) xenotransplantation model. Each surgical specimen was implanted into 4 mice per cohort.

FIG. 34H. Growth kinetics of responding cRCC specimens in the MATRIGEL control or LBC systemic environments as measured by tumor volume at indicated time points.

FIG. 34I. Histopathologic features of human cRCC tissues recovered from mice bearing the LBC systemic environment (left) or in mice bearing MATRIGEL plugs (right). Top panels: hematoxylin and eosin (H&E) staining; Bottom panels: immunohistochemical labeling of CD34-positive endothelial cells; (200× magnification). Inset: tumors cells within grafts grown in LBC tumor bearing mice express the human cRCC marker CAIX (×600 magnification).

FIG. 35A. Experimental scheme to test effects of aspirin on LBC-mediated systemic instigation. All mice were injected with responders and LBC instigating tumors and treated with either 100 mg/kg aspirin or vehicle control; n=10 (5 mice per cohort for 2 independent experiments).

FIG. 35B. Average mass of responding tumors recovered from indicated mice; incidence of tumor formation is indicated below graph.

FIG. 35C. Numbers of VEGFR2+ cells in the bone marrow of experimental mice relative to those of cancer-free mice. Differences not statistically significant (n.s.).

Figure 35:
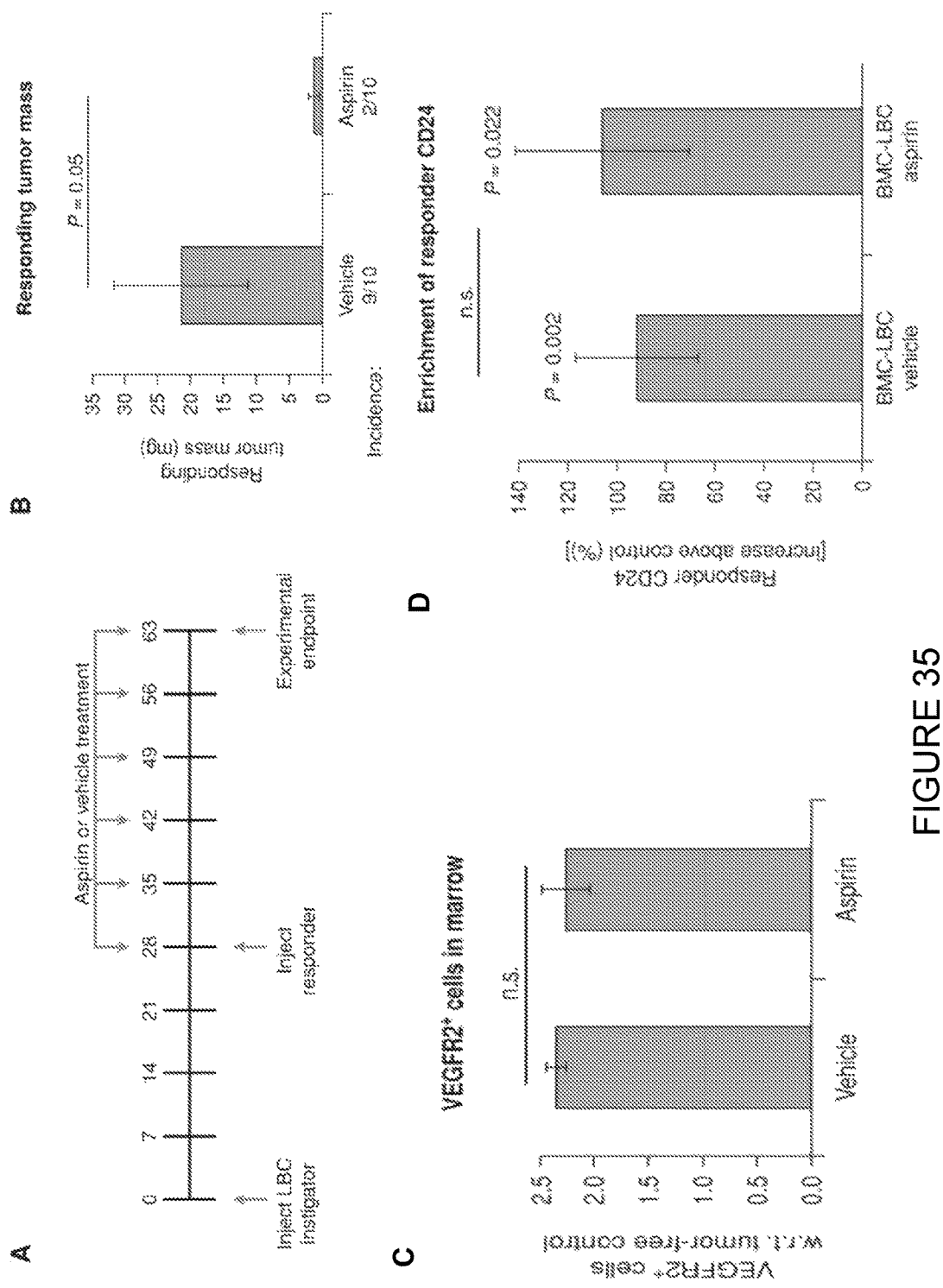
FIGS. 35A-35D. Aspirin treatment inhibits LBC-mediated systemic instigation.

FIG. 35D. Flow cytometric analysis of CD24 expression on GFP+ responder cells co-cultured with indicated BMCs. Values represent percent increase in tumor cell CD24 levels using BMCs from indicated experimental mice relative to those using BMCs from cancer-free mice; n=3 per group; p values represent differences between indicated cohorts and control; values between the different conditions (aspirin v. vehicle) were not significant (n.s.).

Figure 36:
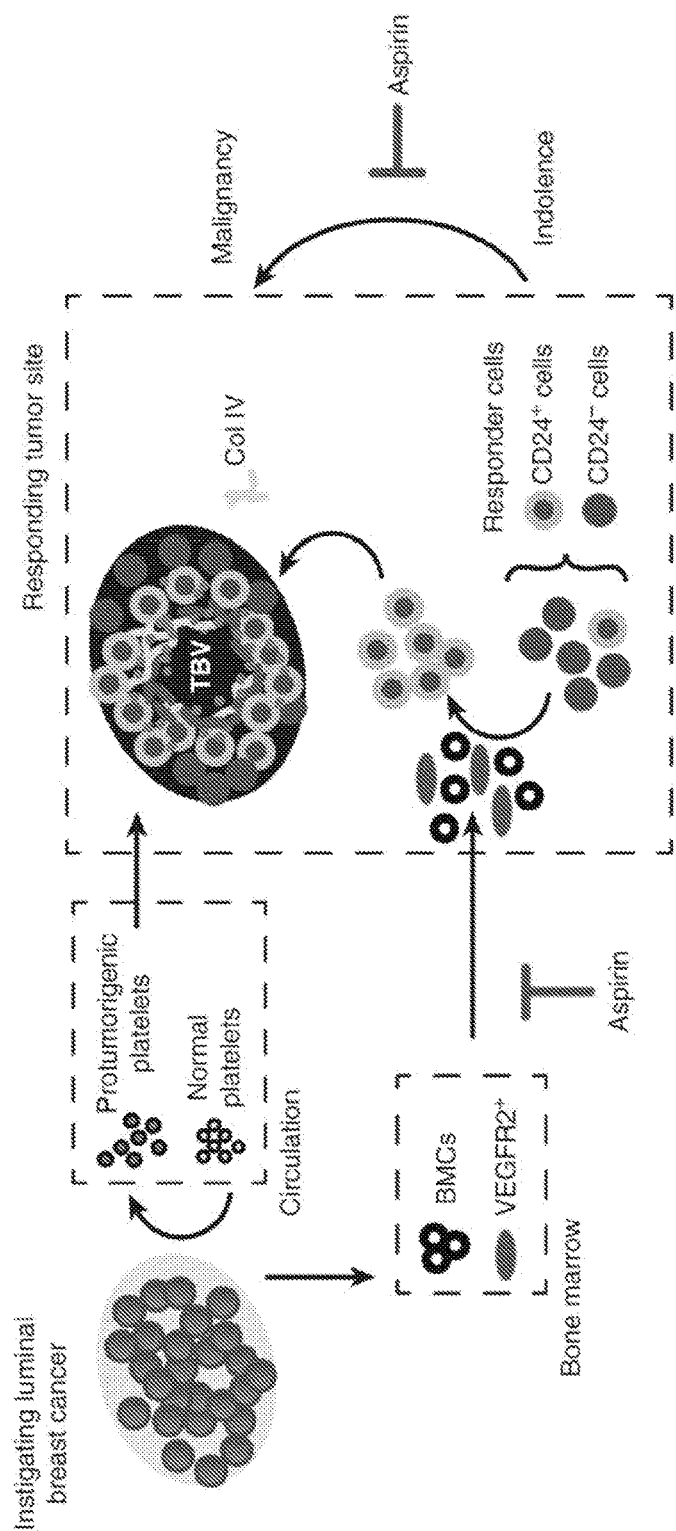

FIG. 36. Model of LBC-mediated systemic instigation. Instigating luminal breast cancers (LBC) establish a tumor-supportive host systemic macroenvironment by modulating circulating platelets and bone marrow cells. Circulating platelets are loaded with a repertoire of cytokines, derived at least in part from the LBC tumor, that render them pro-angiogenic. Platelets are recruited to sites where otherwise indolent tumors reside, ostensibly in response to exposed collagen IV as well as CD24 glycoprotein expression, where there is evidence that platelet-derived factors are released into the responding tumor microenvironment (e.g., activation of STAT3). Bone marrow cells, specifically VEGFR2+ cells, are present in elevated numbers in the marrow and are subsequently mobilized to responding tumor sites where they contribute to the tumor vasculature. At the tumor site, BMCs enrich tumor cell surface expression of CD24, which can serve as a ligand for p-selectin expressed on platelets. This cascade of events results in the growth of highly vascularized responding tumors, which would have otherwise remained indolent. At present, the exact chronological sequence of these events is unclear. Aspirin treatment prevents responding tumor formation and disrupts recruitment of VEGFR2+ cells and activation of STAT3 in the responding tumors, without altering the numbers or function of VEGFR2+ cells in the marrow.

DEFINITIONS

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs.

As used in this specification and the appended claims, the singular forms "a," "an," and "the" include plural references unless the context clearly dictates otherwise. Thus for example, references to "the assay" includes one or more assays, and/or steps of the type described herein and/or which will become apparent to those persons skilled in the art upon reading this disclosure and so forth. Similarly, the word "or" is intended to include "and" unless the context clearly indicates otherwise. Although methods, assays and materials similar or equivalent to those described herein can be used in the practice or testing of this disclosure, suitable methods, assays and materials are described below. The abbreviation, "e.g." is derived from the Latin exempli gratia, and is used herein to indicate a non-limiting example. Thus, the abbreviation "e.g." is synonymous with the term "for example."

Other than in the operating examples, or where otherwise indicated, all numbers expressing quantities of ingredients or reaction conditions used herein should be understood as modified in all instances by the term "about." The term "about" when used in connection with percentages can mean±1%.

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

As used herein, the term "tumor" means a mass of transformed cells that are characterized, at least in part, by containing angiogenic vasculature. The transformed cells are characterized by neoplastic uncontrolled cell multiplication which is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e. a metastatic tumor), a tumor also can be nonmalignant (i.e. non-metastatic tumor). Tumors are hallmarks of cancer, a neoplastic disease the natural course of which is fatal. Cancer cells exhibit the properties of invasion and metastasis and are highly anaplastic. Tumors are among the angiogenesis-mediated diseases encompassed by the therapeutic methods described herein.

As used herein, the term "tumor" is also used in reference to specific types of tumors, e.g., brain tumors including neuroblastoma, medulloblastoma, meningioma and glioblastoma; head and neck cancer, thyroid carcinoma, endocrine tumors, esophageal cancer, small cell and non-small cell lung cancer, colon cancer, rectal cancer, pancreatic cancer, gastric cancer, bladder cancer, hepatic cancer, malignant lymphoma, acute and chronic leukemia, Kaposi's sarcoma, glioma, hemangioma, osteosarcoma, soft tissue sarcoma, malignant melanoma, skin cancer, prostate cancer, breast carcinoma, choriocarcinoma, ovarian cancer, cervical cancer, uterine cancer and mesenchymal tumors, among others.

As used herein, the term "cancer" as described herein include, but are not limited to carcinomas and sarcomas found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus. The types of carcinomas include papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma and sinonasal undifferentiated carcinoma. The types of sarcomas include soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma.

As used herein, the term "metastases" or "metastatic tumor" refers to a secondary tumor that grows separately elsewhere in the body from the primary tumor and has arisen from detached, transported cells, wherein the primary tumor is a solid tumor. The primary tumor, as used herein, refers to a tumor that originated in the location or organ in which it is present and did not metastasize to that location from another location. As used herein, a "malignant tumor" is one having the properties of invasion and metastasis and generally showing a high degree of anaplasia. Anaplasia is the reversion of cells to an immature or a less differentiated form, and it occurs in most malignant tumors.

As used herein, the term "inhibit" or "inhibition" in the context of anti-cancer drug screening in the described assay means the reduction or prevention of conversion of defined cancer responder cells to the malignant state by way of a reduction in the number of malignant phenotypes acquired or no malignant phenotypes acquired or a reduced in the amount of expression of genes known to be overexpressed in malignant cancer cells. That is there is no increased or reduced amount of tumor markers detected by methods known in the art. In one embodiment, inhibition includes slowing the rate of tumor growth and metastasis in the in vitro and/or in vivo proliferation assays. In some embodiments, the reduction by about 20%, about 30%, about 40%, about 50%, about 60%, about 70%, about 80%, about 90%, about 100%, about 125%, about 150% or more compared to in the absence of a test drug in the assay.

The term "subject" and "patient" are used interchangeably herein, and refer to an animal, for example a human. The term "mammal" is intended to encompass a singular "mammal" and plural "mammals," and includes, but is not limited: to humans, primates such as apes, monkeys, orangutans, and chimpanzees; canids such as dogs and wolves; felids such as cats, lions, and tigers; equids such as horses, donkeys, and zebras, food animals such as cows, pigs, and sheep; ungulates such as deer and giraffes; rodents such as mice, rats, hamsters and guinea pigs; and bears. Preferably, the mammal is a human subject. In one embodiment, a "subject" refers to a mammal, preferably a human. The term "individual", "subject", and "patient" are used interchangeably. As used herein, the term "patient" refers to a mammal, including a human.

As used herein, the term "agent" refers to any compound or composition that can be tested as a potential modulator of the conversion of the cancer responder cells to a malignant state. In one embodiment, the agent inhibits or prevents the cancer responder cells from acquiring any of the malignant phenotypes described herein or those known in the art that are correlated with metastasis and malignancy. Examples of agents that can be used include, but are not limited to, small molecules, antibodies, antibody fragments, siRNAs, shRNAs, miRNAs, snpRNA, lncRNAs, nucleic acid molecules (RNAs, DNAs, or DNA/RNA hybrids), antisense oligonucleotides, ribozymes, peptides, peptide mimetics, carbohydrates, lipids, microorganisms, natural products, and the like. In some embodiments, an agent can be isolated or, in other embodiments, not isolated. As a non-limiting example, an agent can be a library of agents. If a mixture of agents is found to be a modulator, the pool can then be further purified into separate components to determine which components are in fact modulators of a target activity.

As used herein, the term "bone marrow derived-cells" (BMCs) refers to any cells isolated or fractionated or separated from a bone marrow aspirate, a bone marrow biopsy, a spleen biopsy, lymph node aspirate or biopsy, or a sample of peripherial circulating blood. In one embodiment, the BMCs are obtained from a subject who has been diagnosed with any cancer. In one embodiment, the BMCs are obtained from a subject who is being treated for cancer.

As used herein, the term "cancer responder cells" or "indolent cancer responder cells" refers to cells or tumors that maintain a balance between proliferation and apoptosis/necrosis such that there is no overall change in size or mass over time; transformed cells that maintain quiescence for a protracted period of time; cells or tumors that exhibit a long latency before exhibiting a growth phase; cells or tumors with slow growth kinetics; cells or tumors that would otherwise die or be cleared upon transplantation/injection into a host; cells or tumors that do not manifest as growing masses in a living animal (for example, in some transgenic mice, tumors are not apparent until a very late stage (e.g., the mouse is more than 10 months old), the mouse is moribund, or the mouse is euthanized and undergoes vivisection); tumors or cell lines that do not display a desmoplastic reaction (stromal desmoplasia); tumors that are not well vascularized; cells or tumors that are not capable of recruiting significant numbers of blood vessels, fibroblasts or myofibroblasts; cell lines or tumors that are not capable activating the bone marrow; cells or tumors that are not capable of instigating the growth of other cells or tumors; cells or tumors that are not capable of recruiting bone marrow-derived cells into their stroma; cells or tumors that do not display histopathology that is consistent with adenocarcinomas; cells or tumors that do not express osteopontin; cells or tumors that do not form growing metastatic colonies upon dissemination from the primary tumor, or after injection per current experimental models of metastasis. In some embodiments, the "cancer responder cells" or "indolent cancer responder cells" can be human tumor cell lines (e.g., breast cancer cell lines or prostate cancer cell lines), fresh or frozen human tumor surgical samples, fresh or frozen human biopsy samples, human tumor cells, premalignant and pre-neoplastic and/or dysplastic cells or tissues, surgical or biopsy samples that grew as xenografts in a host mouse and are passaged again into another host animal, single cell suspensions derived from human biopsy or surgical samples, any genetically modified cell types (not even necessarily tumor), mouse tumor cell lines, mouse tumors that are passaged into another host, spontaneously-arising tumors from transgenic mouse models of tumor initiation and progression.

In one embodiment, the term "cancer responder cells" or "indolent cancer responder cells" refers to cells that have not yet acquired any malignant phenotype described herein but are capable when provided with a malignant supportive environment.

As used herein, the term "standard positive responder cells" or "defined cancer responder cells or cell lines" refers to cancer responder cells that have been shown definitively to undergo indolent conversion to malignant state when provided with a malignant supportive environment.

As used herein, the term "standard positive non-tumor cells" or "defined non-tumor cells" refers to non-tumor cells that have been shown definitively to provide a tumor supportive environment for a defined cancer responder cells and induced the defined cancer responder cells to undergo a conversion from an indolent state to malignant state.

As used herein, the term "indolent state" when used in the context of cancer responder cells refers to the state of these cells where they maintain a balance between proliferation and apoptosis/necrosis such that there is no overall change in size or mass over time; these cells maintain quiescence for a protracted period of time. In other embodiments, they exhibit a variety of phenotypes consistant with the "indolent state," phenotypes such exhibiting a long latency before exhibiting a growth phase; has slow growth kinetics; these cells would otherwise die or be cleared upon transplantation/injection into a host; these cells that do not manifest as growing masses in a living animal; these cells do not display a desmoplastic reaction (stromal desmoplasia); tumors that are not well vascularized; these cells are not capable of recruiting significant numbers of blood vessels, fibroblasts or myofibroblasts; cell lines or tumors that are not capable activating the bone marrow; these cells are not capable of instigating the growth of other cells or tumors; these cells are not capable of recruiting bone marrow-derived cells into their stroma; these cells that do not display histopathology that is consistent with adenocarcinomas; these cells do not express osteopontin; these cells do not form growing metastatic colonies upon dissemination from the primary tumor, or after injection per current experimental models of metastasis.

As used herein, the phrase "indolent conversion to malignant state" or "conversion from an indolent state to a malignant state" when used in the context of cancer responder cells refers to these cells losing the various phenotypes consistant with the indolent state described herein and acquiring various malignant phenotypes described herein.

As used herein, the term "tumor supportive environment" or "malignant supportive environment" when used in the context of cancer responder cells refers to an environment that promotes the indolent conversion to malignant state of the of cancer responder cells. In one embodiment, a "tumor supportive environment" or "malignant supportive environment" comprises non-tumor cells described herein.

As used herein, the term "instigation" refers to a stimulation process by growing tumors, tumor-associated or tumorigenic cells, proteins or other factors secreted by tumors or tumor cells, or a physical process (e.g., surgical or other types of wounds). Typically, instigation refers to systemic instigation which is a stimulation process involving action-at-a-distance. In some embodiments, systemic instigation is mediated by host systemic environment. In some embodiments, instigation refers to systemic stimulation of growth of a distant, otherwise indolent tumor. In some embodiments, instigation includes activation of bone marrow cells (BMCs). In some embodiments, instigation includes mobilization and incorporation of BMCs or bone marrow-derived cells or circulating blood cells into the stroma of distant, otherwise-indolent tumors.

As used herein, the term "instigators" refers to any cells, tumors or processes that enhance, support or induce the growth and/or metastasis of another tumor or cell, in particular, in a systemic fashion. The "instigators" or "instigating" cells or tumors include any cells or tumors that proliferate in an animal host and the proliferation of such cells or tumors enhances, supports or induces the growth and/or metastasis of another tumor or cell, in particular, in a systemic fashion. In particular, the "instigators" or "instigating" cells or tumors can be human tumor cell lines, fresh or frozen human tumor surgical samples, fresh or frozen human biopsy samples, human tumor cells, surgical or biopsy samples that grew as xenografts in a host mouse and are passaged again into another host animal, single cell suspensions derived from human biopsy or surgical samples, any cell type (tumorigenic or non-tumorigenic) that are genetically modified to increase the propensity for tumor formation. In some embodiments, the instigating cells are human tumor cells or cell lines known in the art, such as, for example, BPLER cells, MDA-MB-231 breast cancer cells and MCF7Ras breast cancer cells. Without limitation, the instigating cells or tumors may arise from epithelium, endothelium, or mesothelium. The instigating cells or tumors may be an adenocarcinoma, a squamous cell carcinoma, a sarcoma, a melanoma, a neuroendocrine tumor, a hematopoietic tumor, a lymphoma, a leukemia or a premalignant, preneoplastic and/or dysplastic cell or tissue. Without limitation, the tissue of origin can be lung, liver, breast, prostate, kidney, colon, testis, ovary, stomach, pancreas, thyroid, skin, bone, uterus, or brain.

As used herein, the term "in vitro" refers to events that occur in an artificial environment, e.g., in a test tube or reaction vessel, in cell culture, etc., rather than within a multi-cellular organism.

As used herein, the term "in vivo" refers to events that occur within a multi-cellular organism such as a non-human animal.

In one embodiment, the plasma or platelets or exosomes are standard positive plasma or platelets or exosomes known to provide a tumor supportive environment. In one embodiment, the standard positive plasma or platelets or exosomes provides a tumor supportive environment together with standard positive non-tumor cells.

As used herein, the term "malignant state" as used in the context of the cancer responder cells refers to the cancer responder cells having acquired at least one or more of the malignant phenotypes known in the art. In some embodiments, the malignant phenotypes that characterize a "malignant state" include but are not limited to the following: the ability to the ability to proliferation on soft agar, the ability to proliferate and form tumor in vitro, the ability to proliferate and form tumor in vivo, the expression of malignancy markers, the expression of cancer stem cell markers, the ability to form colonies in soft agar, the ability to proliferate faster, to acquire the expression of genes associated with poor prognosis in cancer patients, the expression of malignancy markers, the acquisition of cancer stem cells markers and/or the ability to proliferate and form tumors in vivo.

As used herein, the malignant phenotypes that marks a malignant state of a cancer responder cell comprises at least one of the following: (1) a gene expression profile that correlates with poor prognosis in patients or animals with cancer, as known in the art for the specific cancer type; (2) a gene expression profile that correlates with proliferation, hyperplasia, neoplasia, tumorigenesis, metastasis, tumor initiation, cancer stem cell state, epithelial-to-mesenchymal transition, as known in the art; (3) gene sequences or mutations that correlate with hyperplasia, neoplasia, tumorigenesis, tumor progression, or metastasis, as known in the art; (4) proteins (including intracellular and secreted proteins) that are known to be expressed by hyperplastic cells, neoplastic cells, cancer cells, metastatic cells, tumor initiating cells, cancer stem cells, or cells that have undergone an epithelial-to-mesenchymal transition; (5) the ability to grow in soft agar, MATRIGEL, inert gels, bioactive gels, or any standard 3-dimensional culture conditions using standard assays; (6) proliferation in vitro or in vivo; (7) the ability to form spheres in any 3-dimensional culture or any standard in vitro tumor-initiation assay; and (8) an altered ability to form a tumor in vivo, including latency, incidence, growth kinetics, tumor mass, tumor volume, malignancy gene expression profile, and metastasis, when injected into experimental animals.

As used herein, the term "modulate" as used in the context of the cancer responder cells' conversion from an indolent state to a malignant state in the presence of non-tumor cells in the described assay refers to whether the non-tumor cells promotes or inhibit the conversion to a malignant state in the indolent cancer responder cells.

As used herein, the term "modulate" as used in the context of the cancer responder cells' conversion from an indolent state to a malignant state in the presence of non-tumor cells and a test candidate drug, agent or compound in the described assay refers to whether the test candidate drug, agent or compound promotes or inhibit the conversion to a malignant state in the indolent cancer responder cells.

As used herein, the term "comprising" means that other elements can also be present in addition to the defined elements presented. The use of "comprising" indicates inclusion rather than limitation.

The term "consisting of" exclusion of any element not recited in that description of the embodiment.

DETAILED DESCRIPTION OF THE INVENTION

Unless otherwise explained, all technical and scientific terms used herein have the same meaning as commonly understood by one of ordinary skill in the art to which this disclosure belongs. Definitions of common terms in molecular biology may be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Further, unless otherwise required by context, singular terms shall include pluralities and plural terms shall include the singular.

Unless otherwise stated, the present invention was performed using standard procedures known to one skilled in the art, for example, in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), which are all herein incorporated by reference in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

The technology described herein is based on the discovery of an in vitro co-culture assay comprising two populations of cells that enables one to determine whether there are circulating cells and/or factors in a cancer patient that would support the further development of malignant cancers from otherwise quiescent, indolent cancer cells. In other words, the in vitro co-culture assay allows one to determine the likelihood that a cancer patient possesses circulating cells and/or factors in vivo that can contribute to an in vivo environment that would support future development of more malignant cancers/tumors in the same patient. The two populations of cells are the circulating cells and/or factors e.g., platelets and plasma, derived from the cancer patient, and indolent cancer responder cells, cells that have not acquire a malignant phenotype yet but are capable thereof when provided with a malignant supportive environment. The circulating cells derived from the cancer patient provide the malignant supportive environment for the indolent cancer cells convert to the malignant state. When the indolent cancer cells convert to the malignant state, the indolent cancer cells manifest a number of malignant phenotypes such as the ability to the ability to proliferation on soft agar, the ability to proliferate and form tumor in vitro, the ability to proliferate and form tumor in vivo, the ability to form colonies in soft agar, the ability to proliferate faster, to acquire the expression of genes associated with poor prognosis in cancer patients, the acquisition of cancer stem cells markers and/or the ability to proliferate and form tumors in vivo, and the expression of malignancy markers (e.g. neutrophilin-1, neutrophilin-2, osteopontin, VEGFR2+, EGFR, IGF-1R and CD24, an increased in the population of $CD44h^{i+}/CD24^{low-}$ cells), and the expression of cancer stem cell markers (e.g. Oct4, Oct4A, c-Myc, Zeb1).

Such an in vitro cell culture assay can be useful for diagnosing the likelihood that a cancer patient would further development of malignant cancer, for determining whether a cancer patient has quiescent, indolent cancer cells that can convert to malignant cancer cells when provided with a malignant supportive environment, for determining whether there are fibroblast cells that contribute to a malignant supportive environment in a cancer patient, for screening of drugs/agents/compounds that can inhibit the "indolent conversion to malignant" process, and for surveillance for resistance to cancer drug therapy. Furthermore, the assay can be adapted for use in determining and identifying factors that enhance malignancy in a cancer patient. For example, factors that enhance the malignancy of cells that are weaky tumorigenic or growing slowly. Additionally, the assay can be adapted for identifying cancer patients who have a tumor-suppressive systemic environment such that these patients could be spared over-treatment.

For example, the in vitro cell culture assay can be adapted to be a diagnostic and/or prognostic test for the presence of tumor-supportive or suppressive bone marrow cells, bone marrow-derived cells, or circulating cells in the blood of cancer patients. Such a test would predict the likelihood that these patients harbor tumor-modulating cells and the likelihood that these patients would have malignant cancer in the future. Such a test can lead to accurate selection of patients who would benefit from preemptive therapy. The tumor-modulating cells can support cancer responder cells conversion to a malignant state, support increase cell proliferation of the cancer responder cells than they would otherwise grow, suppress cancer responder cells conversion to a malignant state, or suppress increase cell proliferation of the cancer responder cells.

For example, the in vitro cell culture assay can be adapted to be a diagnostic and/or prognostic test for the presence of tumor-supportive or suppressive factors in the blood of cancer patients.

For example, the in vitro cell culture assay can be adapted to be a diagnostic and/or prognostic test for tumor-modulatory effects of fibroblasts derived from normal or tumor tissue from a cancer patient or cancer-free subject.

For example, the in vitro cell culture assay can be adapted to be a test to determine the response of a cancer patient to therapy, as measured by altered levels or function of tumor-modulating cells in the circulation of cancer patients For example, the in vitro cell culture assay can be adapted for therapeutic approaches to target cancer responder cells in the presence of a tumor/malignant supportive or suppressive environment and/or circulating factors as potential anti-cancer agents. For example, the assay allows the assessment of the effectiveness of therapeutic agents that specifically target the cancer responder cells, non-tumor cells and circulating factors that are tumor/malignant supportive. For example, the assay allows the assessment of any synergism of therapeutic agents that specifically target the cancer responder cells, non-tumor cells and circulating factors that are tumor/malignant suppressive.

For example, the in vitro cell culture assay can be adapted to be a therapeutic development tool to identify drugs, compounds, chemicals, or antibodies that inhibit or modulate the anti- or pro-tumoirgenic effects of the above cell types and/or blood fluid samples, i.e., a test to screen for cancer therapeutic agents or compounds.

Breast cancer recurrence rates vary following treatment, indicating that tumor cells disseminate early from primary sites but remain indolent indefinitely before progressing to symptomatic disease. The reasons why some indolent disseminated tumors erupt into overt disease are unknown. The inventors discovered a novel process by which certain luminal breast cancer cells and patient tumor specimens (LBC "instigators") establish a systemic macroenvironment that supports outgrowth of otherwise-indolent disseminated tumors ("responders"). Instigating LBCs secrete cytokines that are absorbed by platelets, which are recruited to responding tumor sites where they aid vessel formation. Instigator-activated bone marrow cells (BMCs) enrich responding tumor cell expression of CD24, an adhesion molecule for platelets, and provide a source of VEGFR2+ tumor vessel cells. This cascade results in growth of responder adenocarcinomas and is abolished when platelet activation is inhibited by aspirin. These findings highlight the macroenvironment as an important component of disease progression that can be exploited therapeutically.

Accordingly, embodiments herein provides an in vitro co-culture system comprising a population of cancer responder cells and a population of non-tumor cells wherein the cancer responder cells can convert to a malignant state and exhibit hallmark malignant phenotypes when the cells are placed in a tumor supportive environment. The system is useful for prognosis evaluation of cancer recurrence, malignancy development, cancer drug screening and surveillance for resistance to cancer drug therapy.

In one embodiment, provided herein is an assay comprising in vitro co-culturing a population of cancer responder cells with a population of non-tumor cells; and measuring for at least one malignant phenotype exhibited by the cancer responder cells. Depending on the source and types of cancer responder cells and of non-tumor cells used, whether the cancer responder cells or the non-tumor cells are the test sample, this assay can be adapted for prognosis evaluation of cancer recurrence, malignancy development, cancer drug screening and surveillance for resistance to cancer drug therapy. In one embodiment, in any one assay, only one population of cells is the test sample is used; either the cancer responder cells or the non-tumor cells but not both. In one embodiment, in any one assay, when one population of cells, either the cancer responder cells or the non-tumor cells, is the test sample, the other population of cells is one that have been previously defined and known to either exhibit specific phenotypes under tumor-supportive conditions or tumor-suppressive conditions (cancer responder cells) for or known to be tumor-supportive or tumor-suppressive (for non-tumor cells). For example, when the cancer responder cells are the test samples, then the non-tumor cells are defined non-tumor cells that have been shown previously to be tumor-supportive and are capable of inducing other cancer responder cells to exhibit malignant phenotype in the presence of the defined non-tumor cells. Alternatively, when the non-tumor cells are the test samples, then the cancer responder cells are defined cells that have been shown to convert to a malignant state in the presence of a tumor-supportive environment.

In one embodiment of any assay described, the in vitro co-culture system encompass any tissue culture methods known in the art including but not limited to 2D cultures, 3D cultures, soft agar cultures, MATRIGEL cultures, organoid cultures, sphere-forming cultures, and colony-forming unit cultures.

In one embodiment, provided herein is an assay comprising in vitro co-culturing a population of cancer responder cells with a population of non-tumor cells, wherein the non-tumor cells are obtained from a subject who has been diagnosed with cancer; and measuring a malignant phenotype exhibited by the cancer responder cells. The cancer responder cells are standard positive responder cells. In one embodiment, this assay is useful for prognosis evaluation of cancer recurrence.

For example, co-culturing a defined cancer responder cell line with a non-tumor host test sample in order to determine whether the non-tumor host test sample modulates cancer responder cell malignancy. When the defined cancer responder cell line in such an assay exhibit at least one malignant phenotype or profile described herein, the non-tumor host test sample is determined to positively modulate cancer responder cell malignancy. In order words, the non-tumor host test sample positively induces cancer responder cell to convert from an indolent state to malignancy. Said in a different way, the non-tumor host test sample provides a tumor supportive environment for the cancer responder cell to convert to malignancy or the non-tumor host test sample is tumor-supportive of cancer responder cell malignancy. Such a patient from which the test sample was derived is deemed likely at risk of developing future cancer/tumors. Conversely, when the defined cancer responder cell line in such an assay does not exhibit any malignant phenotype or profile described herein, the non-tumor host test sample is determined to negatively modulate cancer responder cell malignancy. In order words, the non-tumor host test sample does not induce cancer responder cell to convert from an indolent state to malignancy. Said in a different way, the non-tumor host test sample provides a tumor suppressive environment for the cancer responder cell to convert to malignancy or the non-tumor host test sample is tumor-suppressive of cancer responder cell malignancy. Such a patient from which the test sample was derived is deemed unlikely at risk of developing future cancer/tumors.

In one embodiment, the defined cancer responder cell line is a responder cell line that has already been tested with a known, desired behavior. In one embodiment, a known, desired behavior of the defined cancer responder cell line is the conversion from an indolent state to a malignant state and the exhibition of at least one malignant phenotype. In one embodiment, the non-tumor host test sample comprises bone marrow cells, blood components, and/or fibroblasts derived from the patient having been diagnosed with cancer.

In one embodiment of any assay described, the cancer responder cells are responders that are pre-determined to be weakly malignant. These type of responder cells can be tested in any of the assay described herein with non-tumor cells (e.g., bone marrow derived cells) for factors that enhance their malignancy.

In one embodiment, provided herein is an assay comprising in vitro co-culturing (i) a population of cancer responder cells obtained from a subject who has been diagnosed with cancer with (ii) a population of non-tumor cells, the non-tumor cells having been defined with a capability to induce indolent cancer responder cells to convert to a malignant state when the non-tumor cells are co-cultured with indolent cancer responder cells; and measuring a malignant phenotype exhibited by the cancer responder cells. The non-tumor cells are standard positive non-tumor cells known to provide a tumor supportive environment, ie. defined non-tumor cells. In one embodiment, this assay is useful for determining whether a cancer patient has quiescent, indolent cancer cells that can convert to malignant cancer cells when provided with a malignant supportive environment.

For example, co-culturing a defined population of non-tumor cells with a test population of cancer responder cells in order to determine whether the cancer responders from the patient are capable of being modulated by the host cells. In one embodiment, the non-tumor host cells comprise bone marrow cells, blood cells and/or fibroblasts with known behavior, e.g., tumor-promoting or tumor inhibitory. When the test sample of cancer responder cells in such an assay exhibit at least one malignant phenotype or profile described herein in the presence of tumor-promoting non-tumor cells, the patient is determined to positively harbor cancer responder cell capable of conversion from an indolent state to malignancy. Such a patient is likely at risk of developing future cancer/tumors.

In one embodiment, provided herein is an assay comprising in vitro co-culturing a population of cancer responder cells with a population of non-tumor cells; contacting the co-culture with at least one agent or compound; and measuring for at least one malignant phenotype exhibited by the cancer responder cells. In one embodiment, this assay is useful for screening of drugs/agents/compounds that can inhibit the "indolent conversion to malignant" process.

For example, co-culturing defined cancer responder cells with non-tumor host cells and treating the co-culture with a drug, compound, or antibody, to identify drugs that will inhibit promotion of malignancy. When the defined cancer responder cell line in such an assay does not exhibit any malignant phenotype or profile described herein, the test drug, compound, or antibody is determined to negatively modulate cancer responder cell malignancy. Such a drug, compound, or antibody would likely be candidate therapeutics against cancer.

In one embodiment of any assay described, the cancer responder cells are selected from a group consisting of defined cancer responder cell lines, primary cancer/tumor cells, or circulating cancer cells. In one embodiment, the defined cancer responder cell lines are standard positive responder cells.

In one embodiment, the cancer responder cells are normal or cancer cell lines, cells derived from a subject's tumor or a healthy subject donor's normal tissue, or a tumor or tissue specimen.

In some embodiments, the cancer responder cells are transformed cells or tissue specimens from experimental animals or humans that include but are not limited to a) established tumor cell lines, b) experimentally transformed cells obtained or derived from any non-cancerous tissue, c) circulating tumor cells, d) disseminated tumor cells, e) tumor biopsy samples derived from any patient or experimental animal with any kind of cancer, f) tumor surgical specimens from any patient or experimental animal with any kind of cancer.

In some embodiments, cancer responder cells have pre-defined non-malignant behavior including dormancy, indolence, non-proliferation, slow proliferation, cell cycle arrest, non-malignant gene signature, non-malignant genomic sequences, non-malignant protein expression, non-cancer stem cells, differentiated epithelial characteristics, such that their malignant properties as defined herein are increased when subjected to an in vitro co-culture assay described.

In some embodiments, cancer responder cells have pre-defined malignant behaviors defined herein such that their malignant properties are reduced when subjected to an in vitro co-culture assay described.

In some embodiments, cancer responder cells have unknown behaviors and would thus serve as experimental populations to be tested in an in vitro co-culture assay described.

In one embodiment of any assay described, the non-tumor cells are selected from the group consisting of bone marrow-derived circulating cells, buffy coat cells, peripheral circulating cells, and immune cells. In one embodiment, the non-tumor cells are standard positive non-tumor cells known to provide a tumor supportive environment.

In another embodiment of any assay described, the non-tumor cells are populations or sub-fractions of cells that are obtained from a healthy subject (human or experimental animal) or a subject who has been diagnosed with cancer (human or experimental animal). These cells can be obtained from a bone marrow aspirate, a bone marrow biopsy, a spleen biopsy, a blood sample (blood draw or finger prick or any method of obtaining a blood sample), or from the non-tumor portion of any cancer. Techniques used for isolating these cells are known in the art, for examples, standard protocols such as differential centrifugation, buffy coat preps, FACs sorting or magnetic bead sorting. For example, the bone marrow cells comprises cells collected from a cancer subject's or healthy subject donor's bone marrow. Alternatively, the bone marrow-derived cells comprise cells collected from a cancer subject's or healthy subject donor's blood after the subject has been treated with an agent to mobilize bone marrow cells into the circulation. In one embodiment, the circulating cells comprise cells collected from a cancer subject's or healthy subject donor's blood.

In one embodiment of any assay described, the at least one malignant phenotype measured is selected from the group consisting of the ability to proliferation on soft agar, the ability to proliferate and form tumor in vitro, the ability to proliferate and form tumor in vivo, the expression of malignancy hallmark markers, and the expression of cancer stem cell markers.

Some of malignancy hallmark are include but are not limited (1) the ability to stimulate their own growth; (2) the ability to resist inhibitory signals that might otherwise stop their growth; (3) the ability to resist their own programmed cell death (apoptosis); (4) the ability to stimulate the growth of blood vessels to supply nutrients to tumors (angiogenesis); (5) the ability to multiply forever; and (6) the ability to invade local tissue and spread to distant sites (metastasis). Methods of assessing these malignancy hallmark are known in the art, for example, in vitro proliferation assays by way of 2D cultures, 3D cultures, soft agar cultures, MATRIGEL cultures, organoid cultures, sphere-forming cultures, and colony-forming unit cultures; in vivo proliferation assays and metastasis by way of xenograph implants in Nude mice as described herein; angiogenesis assay by way of of xenograph implants in Nude mice as described herein.

Another malignancy hallmark is self-sufficiency in growth signals. Cancer cells can grow and divide without external growth signals. Some cancer cells can generate their own growth signals. For example, glioblastomas can produce their own platelet-derived growth factor (PDGF), and sarcomas can produce their own tumor growth factor $\alpha$ (TGF-$\alpha$).

Often, receptors themselves can be overexpressed in cancer responder cells upon acquiring the malignant state. For example, the epidermal growth factor receptor (EGF- R/erbB) is overexpressed in stomach, brain and breast cancers, while the HER2/neu receptor is overexpressed in stomach and breast cancer. Or, mutated receptors can send signals without any growth factors at all.

In some embodiments, the malignant phenotype encompassed in the assay include but is not limited the following: (1) a gene expression profile that correlates with poor prognosis in patients or animals with cancer, as known in the art for the specific cancer type; (2) a gene expression profile that correlates with proliferation, hyperplasia, neoplasia, tumorigenesis, metastasis, tumor initiation, cancer stem cell state, epithelial-to-mesenchymal transition, as known in the art; (3) gene sequences or mutations that correlate with hyperplasia, neoplasia, tumorigenesis, tumor progression, or metastasis, as known in the art; (4) proteins (including intracellular and secreted proteins) that are known to be expressed by hyperplastic cells, neoplastic cells, cancer cells, metastatic cells, tumor initiating cells, cancer stem cells, or cells that have undergone an epithelial-to-mesenchymal transition; (5) the ability to grow in soft agar, MATRIGEL, inert gels, bioactive gels, or any standard 3-dimensional culture conditions using standard assays; (6) proliferation in vitro or in vivo; (7) the ability to form spheres in any 3-dimensional culture or any standard in vitro tumor-initiation assay; and (8) an altered ability to form a tumor in vivo, including latency, incidence, growth kinetics, tumor mass, tumor volume, malignancy gene expression profile, and metastasis, when injected into experimental animals.

In some embodiments, the malignant phenotype encompassed in the assay include an increase expression of gene or proteins but is not limited the following: neutrophilin-1, neutrophilin-2, osteopontin, IL6, IL1 beta, NANOG, SOX2, mTOR, LIF, Twist, Vimentin, E-cadherin, TGFbeta, Snail, Slug, MMP9, B-catenin, Wnt3A, CD44, CD133, ALDH1, HER2/neu, ERBB-2, VEGFR2+, EGFR, IGF-1R, BRCA1, BRCA2, Ki-67, PCNA, Oct4, Oct4A, c-Myc, Zeb1, and CD24, and an increased in the population of CD44hi+/CD24low– cells.

In some embodiments, the malignant phenotype encompassed in the assay includes an analysis of the gene and/or proteins but is not limited to those listed in Tables 3 and 4.

In some embodiments of any assay described, an analysis of the gene and/or proteins comprises analyzing for an increased in gene expression (ie., genes that are upregulated); analyzing for gene that has been active (ie., activation); analyzing for a decrease in gene expression (ie., genes that are downregulated), and analyzing for mutations in the genes (ie., genes that are mutated).

In some embodiments of any assay described, a gene expression and/or protein expression profile that correlates with proliferation, hyperplasia, neoplasia, tumorigenesis, metastasis, tumor initiation, cancer stem cell state, epithelial-to-mesenchymal transition comprises more than one gene but not limited to those described herein and listed in Tables 3 and 4. Such gene expression and/or protein expression profiles are well known in the art, for example, see Perou C. M., et al. (Nature, 2000, 406: 747-752), van't Veer, L. J., et al. (Nature, 2002, 451: 530-535), Sorlie T., et al. (PNAS, 2001, 19:10869-10874), and Ramaswamy S. et al., (Nature Genetics, 2003, 33: 49-54, See Table 4). The gene profile/signature published by Van't Veer et al. (supra) identified a gene expression signature strongly predictive of a short interval to distant metastases (poor prognosis signature) in patients with breast cancer and negative lymph node. This signature consists of 70 genes regulating cell cycle, invasion, metastasis and angiogenesis and is shown in Table 5. Ramaswamy et al., (supra), described a gene-expression signature from 279 primary solid tumors of diverse types, associated with metastasis and poor clinical outcome. The 17-gene signature associated with metastasis is shown in Table 4.

In some embodiments of any assay described, a gene expression and/or protein expression profile that correlates with proliferation, hyperplasia, neoplasia, tumorigenesis, metastasis, tumor initiation, cancer stem cell state, epithelial-to-mesenchymal transition comprises any combinations of the following genes: IL6, IL1 TNFalpha, EGFR, IGF1R, OCT4, cMyc NANOG, SOX2, LIF, PI3K, mTOR, P-AKT, NFKBeta, ZEB1, Twist, Vimentin, E-cadherin, TGFbeta, slug, sox9, snail, PTEN, p53, K-Ras, CDH1, MMP9, Beta-catenin, wnt proteins, CD44, CD24, CD133, ALDH1, Nestin, Tenascin C, Osteopontin, hepatocyte growth factor, fibroblast growth factor (FGF), epidermal growth factor (EGF), insulin-like growth factor (IGF-1), phosphor-MAPK, activation of PI3K, PIK3CA, claudin, cytokines involved in the mobilization and recruitment of bone marrow derived cells, and miRNAs.

In some embodiments of any assay described, a gene expression and/or protein expression profile that correlates with proliferation, hyperplasia, neoplasia, tumorigenesis, metastasis, tumor initiation, cancer stem cell state, epithelial-to-mesenchymal transition comprises any gene signature that predicts poor cancer prognosis deposited into the Gene Expression Omnibus (GEO) database at the National Institute of Health. In other words, any combination of genes that correlated negatively or positively with poor cancer prognoses that are known in the art.

In one embodiment of any assay described, the assay further comprises co-culturing the populations of cancer responder cells and non-tumor cells in the presence of plasma or platelets or exosomes. In one embodiment, the plasma or platelets or exosomes are obtained from the subject diagnose with cancer. In one embodiment, the plasma or platelets or exosomes are standard positive plasma or platelets or exosomes known to provide a tumor supportive environment. In one embodiment, the standard positive plasma or platelets or exosomes provides a tumor supportive environment together with standard positive non-tumor cells.

Encompassed in all embodiments of any one assay described herein are various components of interest derived from blood from either a healthy subject or a subject who has been diagnosed with cancer or a subject who is currently being treated for cancer. In some embodiments, the components of interest that are derived from blood include but are not limited to bone marrow-derived circulating cells, buffy coat cells, circulating cells, immune cells, plasma, serum, platelets, exosomes, or circulating tumor cells.

Encompassed in all embodiments of any one assay described herein are secretion products cancer responder cells or non-tumor cell types in in vitro cell cultures or in vivo. In one embodiment, the secretion products comprise any and all secreted proteins or extracellular factors secreted by the cancer responder cells or non-tumor cell types into their surrounding medium or proximal fluid.

In one embodiment, the serum or plasma comprises preparations of blood fluids from a bone marrow aspirate, a bone marrow biopsy, a spleen biopsy, a lymph node biopsy or resection, a blood sample, or from the non-tumor portion of any cancer.

In one embodiment of any assay described, the assay further comprises co-culturing the populations of responder cells and non-tumor cells with a population of fibroblast cells. In one embodiment, this assay is useful for determining whether there are fibroblast cells that contribute to a malignant supportive environment in a cancer patient.

Fibroblasts are mesenchymal cells that will be isolated from any tissue from healthy donors or cancer-bearing subjects (human or experimental animal) after dissociation of non-malignant, tumors and other tissues using standard protocols known in the art.

In some embodiments of any assay described, the fibroblasts are normal or immortalized cell lines or cells collected from a tumor or tissue specimen.

In one embodiment of any assay described, the population of fibroblast cells is obtained from a healthy, cancer-free tissue from a subject.

In another embodiment of any assay described, the population of fibroblast cells is obtained from a cancer tumor tissue excised from a subject.

In one embodiment of any assay described, the population of fibroblast cells is separated by a membrane from the population of cancer responder cells and the population of non-tumor cells in the co-culture.

In one embodiment of any assay described, the assay further comprises contacting the co-culture with at least a test agent or compound. For example, a test agent or compound that can inhibit the conversion of the cancer responder cells to the malignant state.

In one embodiment of any assay described, the population of cancer responder cells is selected from HME, HMLE, HMLER hygro-H-rasV12 (HMLER-HR), HMLER-puro-H rasV12, BPE, BPLER, BT-549, and MCF7, MCF7-Ras human breast tumor cells. These are examples are defined cancer responder cell lines and are also examples of standard positive responder cells.

In one embodiment of any assay described, the cancer responder cells are in an indolent state.

In one embodiment of any assay described, when the cancer responder cells exhibit an increase expression of any one of the following: Oct4, Oct4A, c-Myc, Zeb1, osteopontin, EGFR and IGF-1R, or there is an increased in CD44hi+/CD24low− cells indicates that the cancer responder cells exhibit a malignant phenotype.

In one embodiment of any assay described, when the cancer responder cells exhibit an increase expression of any one of the following: CD24, or there is an increased in CD44hi+/CD24low− cells indicates that the responder cells exhibit a malignant phenotype.

In one embodiment of any assay described, the non-tumor cells are obtained from a bone marrow aspirate, a bone marrow biopsy, a spleen biopsy, a blood sample, a sample of lymph node aspirate, biopsy or resection, and a non-tumor portion of a cancer from a subject.

In one embodiment of any assay described, the non-tumor cells are selected from the group consisting of bone marrow-derived circulating cells, spleen-derived cells, lymph node-derived cells, buffy coat cells, peripheral blood circulating cells, and immune cells.

In one embodiment of any assay described, the subject has been diagnosed with triple-negative breast cancer (TNBC) or luminal breast cancer (LBC) or Her2+ breast cancer.

In one embodiment of any assay described, the subject has undergone reduction mammoplasty, breast biopsy, breast lumpectomy, partial mastectomy or total mastectomy.

In one embodiment of any assay described, the subject has undergone bone marrow cell mobilization therapy, bone marrow transplantation, immune-suppression therapy, non-steroidal anti-inflammatory therapy, anti-oxidant therapy, radiation therapy, chemotherapy, hormone therapy and/or targeted therapy or treated with placebo.

In one embodiment of any assay described, the assay further comprises selecting a subject who has been diagnosed with cancer.

In one embodiment of any assay described, the assay further comprises providing a sample of bone marrow, a sample of bone marrows-derived cells, a blood sample, a sample of spleen-derived cells, a sample of lymph node-derived cells, a healthy breast tissue sample, and/or a cancer tissue from the subject.

In one embodiment of any assay described, the assay further comprises diagnosing that the subject likely has malignant tumor supportive cells and/or factors and/or fibroblast when the cancer responder cells exhibition of at least one malignant phenotype when the assay uses non-tumor cells that are derived from the subject diagnosed with cancer.

In one embodiment of any assay described, the assay further comprises diagnosing that the subject is likely to developed malignant cancer when the cancer responder cells exhibit of at least one malignant phenotype when the assay uses non-tumor cells that are derived from the subject diagnosed with cancer.

In one embodiment of any assay described, the assay further comprises diagnosing that the subject likely has indolent cancer responder cells capable of converting to malignant tumor when the cancer responder cells exhibit of at least one malignant phenotype when the assay uses cancer responder cells that are derived from the subject diagnosed with cancer.

In one embodiment of any assay described, the non-tumor cells have a capability to induce indolent cancer responder cells to convert to a malignant state when the non-tumor cells are co-cultured with indolent cancer responder cells.

In one embodiment of any assay described, the cancer responder cells are indolent but will convert to a malignant state when the non-tumor cells that have a capability to induce indolent cancer responder cells to convert to a malignant state are present.

In one embodiment of any assay described, the assay further comprises determining that the at least one agent or compound added to the co-culture likely has a capability of inhibiting or blocking the conversion of cancer responder cells to a malignant state when the cancer responder cells in the co-culture exhibit at least one less malignant phenotype or at least a reduced or decreased malignant phenotype compared to in the absence of the at least one agent or compound.

In one embodiment, provided herein is an assay comprising performing a first co-culture comprising in vitro co-culturing a population of cancer responder cells with a population of non-tumor cells obtained from a subject at a first time point, wherein the cancer responder cells are indolent but capable of converting to a malignant, and wherein the subject has been diagnosed with cancer; contacting the co-culture with at least one anti-cancer therapeutic agent or compound that is currently being used to treat the cancer in the subject; and measuring for at least one malignant phenotype exhibited by the cancer responder cells; performing a second co-culture comprising in vitro co-culturing a population of cancer responder cells with a population of non-tumor cells obtained from a subject at a second time point, wherein the cancer responder cells are the same cells as used in the first co-culture; contacting the second co-culture with the at least one anti-cancer therapeutic agent or compound used in the first co-culture; and measuring for at least one malignant phenotype exhibited by the cancer responder cells; and comparing the malignant phenotype exhibited by the cancer responder cells of the first and second co-cultures. This assay is useful for surveillance for resistance to cancer drug therapy.

In one embodiment, the assay further comprising determining that the subject has developed resistance to the at least one anti-cancer therapeutic agent or compound currently being used to treat the cancer when the cancer responder cells in the co-culture exhibit at least one additional malignant phenotype or at least an increased malignant phenotype in the second co-culture compared to the first co-culture.

In one embodiment, the assay further comprises determining that the at least one agent or compound currently being used to treat the cancer is still effective against the cancer when the cancer responder cells in the second co-culture exhibit no additional malignant phenotype or at least an increased malignant phenotype compared to the first co-culture.

For example, co-culturing defined cancer responder cells with non-tumor host cells. Then treat defined cancer respond cells with an anti-cancer drug, compound, or antibody in the presence of test populations of host cells to determine whether there are host cells that mediate drug resistance. When cancer responder cells in such an assay exhibit at least one additional malignant phenotype or profile described herein in the presence of current cancer drug therapy, the patient form which the test populations of host cells were derived is determined to have positively developed resistance to that cancer drug therapy.

In one embodiment, provided herein is an in vitro method for surveillance of cancer recurrence in a subject comprising: (a) providing a biological sample at a first time point and a second time point, the biological samples are from a subject who has previously been diagnosed with cancer, wherein the second time point is after the first time point and both time points are after the subject has been diagnosed with cancer; conducting the in vitro co-culture assay described herein; and comparing the measurement of the malignant phenotype of the cancer responder cells in the assay of step b for the second time point with that of the first time point. In one embodiment of this assay, the cancer responder cells used in the assay is a standard positive responder cells and the non-tumor cells are obtained from the subject at the first and second time point.

In one embodiment of the method, the cancer responder cells of the two time points do not exhibit a malignant phenotype indicate that there is unlikely cancer recurrence and the cancer is in remission.

In one embodiment of the method, when the cancer responder cells of the first time point do not exhibit a malignant phenotype but the cancer responder cells of the second time point do exhibit a malignant phenotype indicate that there is likely cancer recurrence in the subject.

In one embodiment of any method described, the method further comprises treating the subject when it is observed that the cancer responder cells at the second time point exhibit a malignant phenotype.

In one embodiment, provided herein is a kit comprising a cell culture of a population of cancer responder cells for diagnosing the likelihood of cancer recurrence in a subject or for determining the likelihood of development of cancer drug resistance in a subject. In one embodiment of the kit, the cancer responder cells are standard positive responder cells.

In one embodiment of the kit, the cancer responder cells are selected from HME, HMLE, HMLER hygro-H-rasV12 (HMLER-HR), HMLER-puro-H rasV12, BPE, BPLER, BT-549, and MCF7, MCF7-Ras human breast tumor cells.

In one embodiment of the kit, the kit further comprises a population of positive control non-tumor cells capable of inducing the cancer responder cells to exhibit a malignant phenotype in an assay of described herein.

In one embodiment, provided herein is an assay comprising co-culturing a population of breast cancer responder cells with a population of bone marrow derived-cells (BMCs) obtained from a subject who has been diagnosed with breast cancer; and measuring for at least a malignant phenotype exhibited by the breast cancer responder cells. In other embodiments, any other non-tumor cells obtained from a subject who has been diagnosed with breast cancer can be used for the assay.

In one embodiment, the assay further comprises co-culturing the populations of breast cancer responder cells and BMCs in the presence of plasma or platelets or exosomes derived from the subject.

In one embodiment, the assay further comprises comprising co-culturing the populations of responder cells and BMCs with a population of fibroblast cells derived from the subject. In one embodiment, the population of fibroblast cells is obtained from a healthy, cancer-free breast tissue from the subject. In another embodiment, the population of fibroblast cells is obtained from a breast cancer tumor tissue excised from the subject.

In one embodiment, the population of fibroblast cells is separated by a membrane from the population of breast cancer responder cells and the population of BMCs in the co-culture. In one embodiment, the membrane is semi-pemeable and cell-impeameable.

In one embodiment, the population of breast cancer responder cells are selected from HME, HMLE, HMLER hygro-H-rasV12 (HMLER-HR), HMLER-puro-H rasV12, BPE, BPLER, BT-549, and MCF7, MCF7-Ras human breast tumor cells.

In one embodiment, the population of breast cancer responder cells is in an indolent state.

In one embodiment, the subject has been diagnosed with triple-negative breast cancer (TNBC) or luminal breast cancer (LBC) or Her2+ breast cancer.

In one embodiment, when the diagnosed breast cancer is TNBC and the population of breast cancer responder cells exhibit an increase expression of any one of the following: Oct4, Oct4A, c-Myc, Zeb1, osteopontin, EGFR and IGF-1R, or there is an increased in CD44hi+/CD24low− cells indicates that the breast cancer responder cells exhibit a malignant phenotype, and it is highly likely that the subject would have cancer recurrence.

In one embodiment, when the diagnosed breast cancer is LBC and the population of breast cancer responder cells exhibit an increase expression of any one of the following: CD24, or there is an increased in CD44hi+/CD24low− cells indicates that the breast cancer responder cells exhibit a malignant phenotype, and it is highly likely that the subject would have cancer recurrence.

In one embodiment of any assay described, the subject has undergone reduction mammoplasty, breast biopsy, breast lumpectomy, partial mastectomy or total mastectomy.

In one embodiment of any assay described, the subject has undergone bone marrow cell mobilization therapy, bone marrow transplantation, immune-suppression therapy, non-steroidal anti-inflammatory therapy, anti-oxidant therapy, radiation therapy, chemotherapy, hormone therapy and/or targeted therapy or treated with placebo.

In one embodiment of any assay described, the assay further comprises selecting a subject who has been diagnosed with breast cancer.

In one embodiment of any assay described, the assay further comprises providing a sample of bone marrow, a sample of bone marrow derived cells, a blood sample, a healthy breast tissue sample, and/or a breast cancer tissue from the subject.

In one embodiment, provided herein is an in vitro method for surveillance of breast cancer recurrence in a subject comprising providing a biological sample at a first time point and a second time point, the biological samples are from a subject who has previously been diagnosed with breast cancer, wherein the second time point is after the first time point and both time points are after the subject has been diagnosed with breast cancer; conducting an assay comprising a co-culture described herein; and comparing the measurement of the malignant phenotype of the responder breast cancer cells in the co-culture assay described in the second time point with that of the first time point. In one embodiment of this assay, the cancer responder cells used in the assay is a standard positive responder cells and the non-tumor cells are obtained from the subject at the first and second time point.

In one embodiment, when the breast cancer responder cells of the two time points do not exhibit a malignant phenotype indicate that there is unlikely cancer recurrence and the cancer is in remission.

In one embodiment, when the breast cancer responder cells of the first time point do not exhibit a malignant phenotype but the breast cancer responder cells of the second time point do exhibit a malignant phenotype indicate that there is likely cancer recurrence in the subject.

In one embodiment, the method further comprises treating the subject when it is observed that the breast cancer responder cells at the second time point exhibit a malignant phenotype.

The present invention can be defined in any of the following numbered paragraphs:

[1] An assay comprising in vitro co-culturing a population of cancer responder cells with a population of non-tumor cells; and measuring for at least one malignant phenotype exhibited by the cancer responder cells.

[2] The assay of claim 1, wherein the cancer responder cells are selected from a group consisting of defined cancer responder cell lines, primary cancer/tumor cells, or circulating cancer cells.

[3] The assay of claim 1 or 2, wherein the non-tumor cells are selected from the group consisting of bone marrow-derived circulating cells, buffy coat cells, peripheral circulating cells, and immune cells.

[4] The assay of any one of claims 1-3, wherein the at least one malignant phenotype measured is selected from the group consisting of the ability to proliferation on soft agar, the ability to proliferate and form tumor in vitro, the ability to proliferate and form tumor in vivo, the expression of malignancy markers, and the expression of cancer stem cell markers.

[5] The assay of any one of claims 1-4, further comprising co-culturing the populations of cancer responder cells and non-tumor cells in the presence of plasma or platelets or exosomes.

[6] The assay of any one of claims 1-5, further comprising co-culturing the populations of responder cells and non-tumor cells with a population of fibroblast cells.

[7] The assay of claim 6, wherein the population of fibroblast cells is obtained from a healthy, cancer-free tissue from a subject.

[8] The assay of claim 6, wherein the population of fibroblast cells is obtained from a cancer tumor tissue excised from a subject.

[9] The assay of any one of claims 6-8, wherein the population of fibroblast cells is separated by a membrane from the population of cancer responder cells and the population of non-tumor cells in the co-culture.

[10] The assay of any one of claims 1-9, further comprising contacting the co-culture with at least a test agent or compound.

[11] The assay of any one of claims 1-10, wherein the population of cancer responder cells are selected from HME, HMLE, HMLER hygro-H-rasV12 (HMLER-HR), HMLER-puro-H rasV12, BPE, BPLER, BT-549, and MCF7, MCF7-Ras human breast tumor cells.

[12] The assay of any one of claims 1-11, wherein the cancer responder cells are in an indolent state.

[13] The assay of any one of claims 1-12, wherein when the cancer responder cells exhibit an increase expression of any one of the following: Oct4, Oct4A, c-Myc, Zeb1, osteopontin, EGFR and IGF-1R, or there is an increased in CD44hi+/CD24low− cells indicates that the cancer responder cells exhibit a malignant phenotype.

[14] The assay of any one of claims 1-13, wherein when the cancer responder cells exhibit an increase expression of any one of the following: CD24, or there is an increased in CD44hi+/CD24low− cells indicates that the responder cells exhibit a malignant phenotype.

[15] The assay of any one of claims 1-13, wherein the non-tumor cells are obtained from a bone marrow aspirate, a bone marrow biopsy, a spleen biopsy, a blood sample, a sample of lymph node aspirate or biopsy, the non-tumor portion of a cancer from a subject.

[16] An assay comprising in vitro co-culturing a population of cancer responder cells with a population of no tumor cells obtained from a subject who has been diagnosed with cancer; and measuring a malignant phenotype exhibited by the cancer responder cells.

[17] The assay of claim 16, further comprising co-culturing the populations of cancer responder cells and non-tumor cells in the presence of plasma or platelets or exosomes derived from the subject.

[18] The assay of claim 16 or 17, further comprising co-culturing the populations of cancer responder cells and non-tumor cells with a population of fibroblast cells.

[19] The assay of claim 18, wherein the population of fibroblast cells is obtained from a healthy, cancer-free breast tissue from the subject.

[20] The assay of claim 18, wherein the fibroblast cells are obtained from a tumor tissue excised from the subject.

[21] The assay of any one of claims 17-20, wherein the population of fibroblast cells is separated by a membrane from the population of cancer responder cells and the population of non-tumor cells in the co-culture.

[22] The assay of any one of claims 16-21, wherein the population of cancer responder cells are selected from HME, HMLE, HMLER hygro-H-rasV12 (HMLER-HR), HMLER-puro-H rasV12, BPE, BPLER, BT-549, and MCF7, MCF7-Ras human breast tumor cells.

[23] The assay of any one of claims 16-22, wherein the cancer responder cells are in an indolent state.

[24] The assay of any one of claims 16-23, wherein the non-tumor cells are selected from the group consisting of bone marrow-derived circulating cells, spleen-derived cells, lymph node-derived cells, buffy coat cells, peripheral blood circulating cells, and immune cells.

[25] The assay of any one of claims 16-24, wherein the subject has been diagnosed with triple-negative breast cancer (TNBC) or luminal breast cancer (LBC) or Her2+ breast cancer.

[26] The assay of claim 25, wherein the subject has undergone reduction mammoplasty, breast biopsy, breast lumpectomy, partial mastectomy or total mastectomy.

[27] The assay of any one of claims 16-26, wherein the subject has undergone radiation therapy, chemotherapy, hormone therapy and/or targeted therapy.

[28] The assay of any one of claims 16-27, further comprising selecting a subject who has been diagnosed with cancer.

[29] The assay of any one of claims 16-28, further comprising providing a sample of bone marrow, a sample of bone marrows-derived cells, a blood sample, a sample of spleen-derived cells, a sample of lymph derived cells, a healthy breast tissue sample, and/or a cancer tissue from the subject.

[30] The assay of any one of claims 16-29, further diagnosing that the subject likely have malignant tumor supportive cells and/or factors and/or fibroblast when the cancer responder cells exhibition of at least one malignant phenotype.

[31] The assay of any one of claims 16-30, further diagnosing that the subject likely to developed malignant cancer when the cancer responder cells exhibit of at least one malignant phenotype.

[32] An assay comprising in vitro co-culturing (i) a population of cancer responder cells obtained from a subject who has been diagnosed with cancer with (ii) a population of non-tumor cells, the non-tumor cells having a capability to induce indolent cancer responder cells to convert to a malignant state when the non-tumor cells are co-cultured with indolent cancer responder cells; and measuring a malignant phenotype exhibited by the cancer responder cells.

[33] The assay of claim 32, further comprising co-culturing the populations of cancer responder cells and non-tumor cells in the presence of plasma or platelets or exosomes derived from the subject.

[34] The assay of claim 32 or 33, further comprising co-culturing the populations of cancer responder cells and non-tumor cells with a population of fibroblast cells.

[35] The assay of claim 34, wherein the population of fibroblast cells is obtained from a healthy, cancer-free breast tissue from the subject.

[36] The assay of claim 34, wherein the fibroblast cells are obtained from a tumor tissue excised from the subject.

[37] The assay of any one of claims 34-36, wherein the population of fibroblast cells is separated by a membrane from the population of cancer responder cells and the population of non-tumor cells in the co-culture.

[38] The assay of any one of claims 34-37, wherein the cancer responder cells are in an indolent state.

[39] The assay of claim 38, wherein the cancer responder cells are obtained from a sample of bone marrow, a blood sample, a sample of spleen, a sample of lymph node aspirate or biopsy or resection, a healthy tissue sample, and/or a cancer tissue from the subject.

[40] The assay of any one of claims 34-39, wherein the non-tumor cells are selected from the group consisting of bone marrow-derived circulating cells, buffy coat cells, peripheral circulating cells, and immune cells.

[41] The assay of any one of claims 34-40, wherein the subject has undergone bone marrow cell mobilization therapy, bone marrow transplantation, immune-suppression therapy, non-steroidal anti-inflammatory therapy, anti-oxidant therapy, radiation therapy, chemotherapy, hormone therapy and/or targeted therapy or treated with placebo.

[42] The assay of any one of claims 34-41, further comprising selecting a subject who has been diagnosed with cancer.

[43] The assay of any one of claims 34-42, further comprising providing a sample of bone marrow, a sample of bone marrows-derived cells, a blood sample, a sample of spleen-derived cells, a sample of lymph node-derived cells, a healthy breast tissue sample, and/or a cancer tissue from the subject.

[44] The assay of any one of claims 34-43, further diagnosing that the subject likely have indolent cancer responder cells capable of converting to malignant tumor when the cancer responder cells exhibit of at least one malignant phenotype.

[45] An assay comprising in vitro co-culturing a population of cancer responder cells with a population of non-tumor cells; contacting the co-culture with at least one agent or compound; and measuring for at least one malignant phenotype exhibited by the cancer responder cells.

[46] The assay of claim 45, wherein the non-tumor cells have a capability to induce indolent cancer responder cells to convert to a malignant state when the non-tumor cells are co-cultured with indolent cancer responder cells.

[47] The assay of claim 46, wherein the cancer responder cells are indolent but will convert to a malignant state when the non-tumor cells that have a capability to induce indolent cancer responder cells to convert to a malignant state are present.

[48] The assay of claim 47, further determining that the at least one agent or compound added to the co-culture likely has a capability of inhibiting or blocking the conversion of cancer responder cells to a malignant state when the cancer responder cells in the co-culture exhibit at least one less malignant phenotype or at least a reduced or decreased malignant phenotype compared to in the absence of the at least one agent or compound.

[49] An assay comprising performing a first co-culture comprising in vitro co-culturing a population of cancer responder cells with a population of non-tumor cells obtained from a subject at a first time point, wherein the cancer responder cells are indolent but capable of converting to a malignant, and wherein the subject has been diagnosed with cancer; contacting the co-culture with at least one anti-cancer therapeutic agent or compound that is currently being used to treat the cancer in the subject; and measuring for at least one malignant phenotype exhibited by the cancer responder cells; performing a second co-culture comprising in vitro co-culturing a population of cancer responder cells with a population of non-tumor cells obtained from a subject at a second time point, wherein the cancer responder cells are the same cells as used in the first co-culture; contacting the second co-culture with the at least one anti-cancer therapeutic agent or compound used in the first co-culture; and measuring for at least one malignant phenotype exhibited by the cancer responder cells; and comparing the malignant phenotype exhibited by the cancer responder cells of the first and second co-cultures.

[50] The assay of claim 50, further comprising determining that the subject has developed resistance to the at least one anti-cancer therapeutic agent or compound currently being used to treat the cancer when the cancer responder cells in the co-culture exhibit at least one additional malignant phenotype or at least an increased malignant phenotype in the second co-culture compared to the first co-culture.

[51] The assay of claim 50, further comprising determining that the at least one agent or compound currently being used to treat the cancer is still effective against the cancer when the cancer responder cells in the second co-culture exhibit no additional malignant phenotype or at least an increased malignant phenotype compared to the first co-culture.

[52] An in vitro method for surveillance of cancer recurrence in a subject comprising providing a biological sample at a first time point and a second time point, the biological samples are from a subject who has previously been diagnosed with cancer, wherein the second time point is after the first time point and both time points are after the subject has been diagnosed with cancer; conducting the assay of any one of claims 16-31; and comparing the measurement of the malignant phenotype of the cancer responder cells in the assay of step b for the second time point with that of the first time point.

[53] The method of claim 52, when the cancer responder cells of the two time points do not exhibit a malignant phenotype indicate that there is unlikely cancer recurrence and the cancer is in remission.

[54] The method of claim 52, when the cancer responder cells of the first time point do not exhibit a malignant phenotype but the cancer responder cells of the second time point do exhibit a malignant phenotype indicate that there is likely cancer recurrence in the subject.

[55] The method of claim 54, further comprising treating the subject when it is observed that the cancer responder cells at the second time point exhibit a malignant phenotype.

[56] A kit comprising a cell culture of a population of cancer responder cells for diagnosing the likelihood of cancer recurrence in a subject or for determining the likelihood of development of cancer drug resistance in a subject.

[57] The kit of claim 56, wherein the cancer responder cells are selected from HME, HMLE, HMLER hygro-H-rasV12 (HMLER-HR), HMLER-puro-H rasV12, BPE, BPLER, BT-549, and MCF7, MCF7-Ras human breast tumor cells.

[58] The kit of claim 56 or 57, further comprising a population of positive control non-tumor cells capable of inducing the cancer responder cells to exhibit a malignant phenotype in an assay of any one of claims 16-31.

This invention is further illustrated by the following example which should not be construed as limiting. The contents of all references cited throughout this application, as well as the figures and table are incorporated herein by reference.

Those skilled in the art will recognize, or be able to ascertain using not more than routine experimentation, many equivalents to the specific embodiments of the invention described herein. Such equivalents are intended to be encompassed by the following claims.

EXAMPLE

Example 1—An In Vitro Functional Assay to Predict Breast Cancer Recurrence

The main goal here is to generation of an in vitro test of the tumor-promoting capability of the host systemic environment. The inventors have shown previously that tumor-supportive host systemic environment is defined by elevated plasma levels of osteopontin and circulating pro-tumorigenic bone marrow-derived cells. It is known that the pro-tumorigenic BMCs can be unique to hosts bearing certain instigating tumors. The inventors set out to define the properties of instigating tumors that operate in this fashion. In other words, these BMCs are not found in cancer-free hosts or hosts bearing non-instigating tumors (defined as tumors that grow aggressively, but do not have systemic instigating capability).

It has also been shown that once recruited to the sites where indolent tumors reside, the pro-tumorigenic bone marrow-derived cells activate tissue fibroblasts to confer upon them a tumor-promoting molecular profile. They do so, in part, by secreting the cytokine, granulin. The pro-tumorigenic bone marrow-derived cells also cause otherwise indolent tumor cells to adopt a phenotype and molecular profile consistent with malignant cancers. At this point, the malignant profile is defined by expression of Oct-4, Zeb-1, and c-myc transcription factors.

It has also been shown that EGF and IGF-1 secreted by cells in the tumor microenvironment (BMCs and fibroblasts) cause the tumor cells to increase expression of Oct-4, Zeb-1, and c-myc genes. Therefore, elevated expression of these genes serves as a readout for malignant conversion.

Therefore, by testing the effects of circulating bone marrow-derived cells (for example, peripheral blood cells or bone marrow aspirates obtained from donor hosts) and/or tissue fibroblasts (derived from normal breast tissue or tumor tissue) on otherwise indolent tumor cells (either cell lines or patient tumor samples) in the described in vitro cell culture assay, the result behavior and/or phenotype of the indolent cells can be used to predict whether the donor host bears a tumor-promoting systemic environment that is likely to support disease recurrence.

Figure 1:
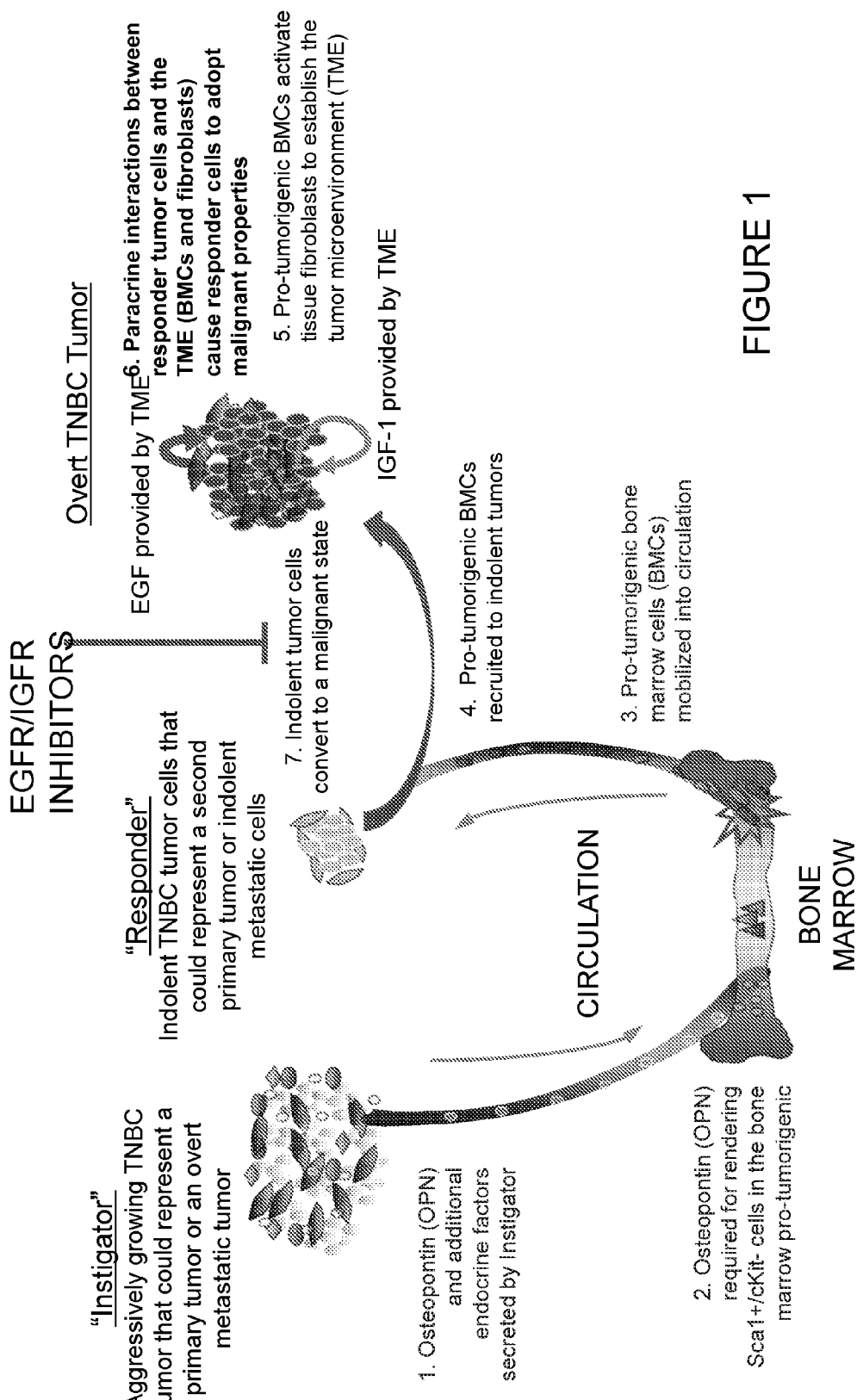
FIG. 1 shows the schematic hallmarks of the triple negative breast cancer (TNBC) systemic instigation cascade in vivo.
Figure 2:
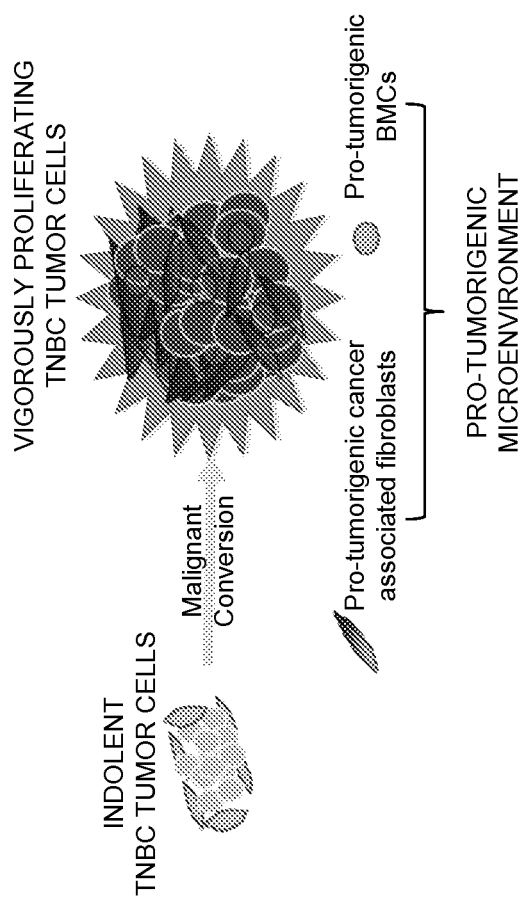
FIG. 2 shows the effects of pro-tumorgenic microenvironment in transforming indolent triple negative breast cancer cells to aggressive malignant breast cancer cells.
Figure 3:
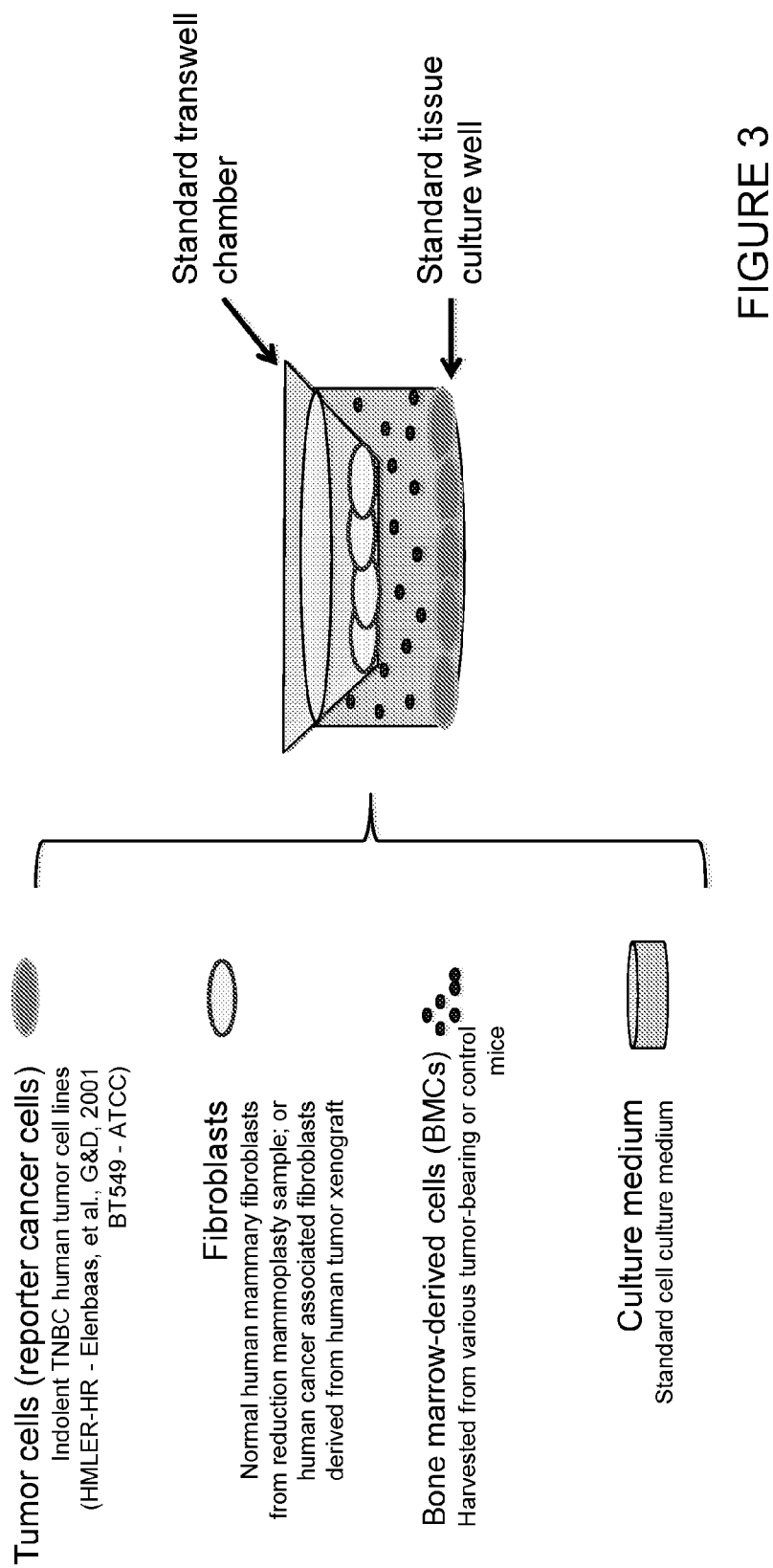
FIG. 3 is an embodiment of the in vitro cell culture system for testing the presences and also the effects of a pro-tumorgenic microenvironment showing the various components in the cell culture system.
Figure 4:
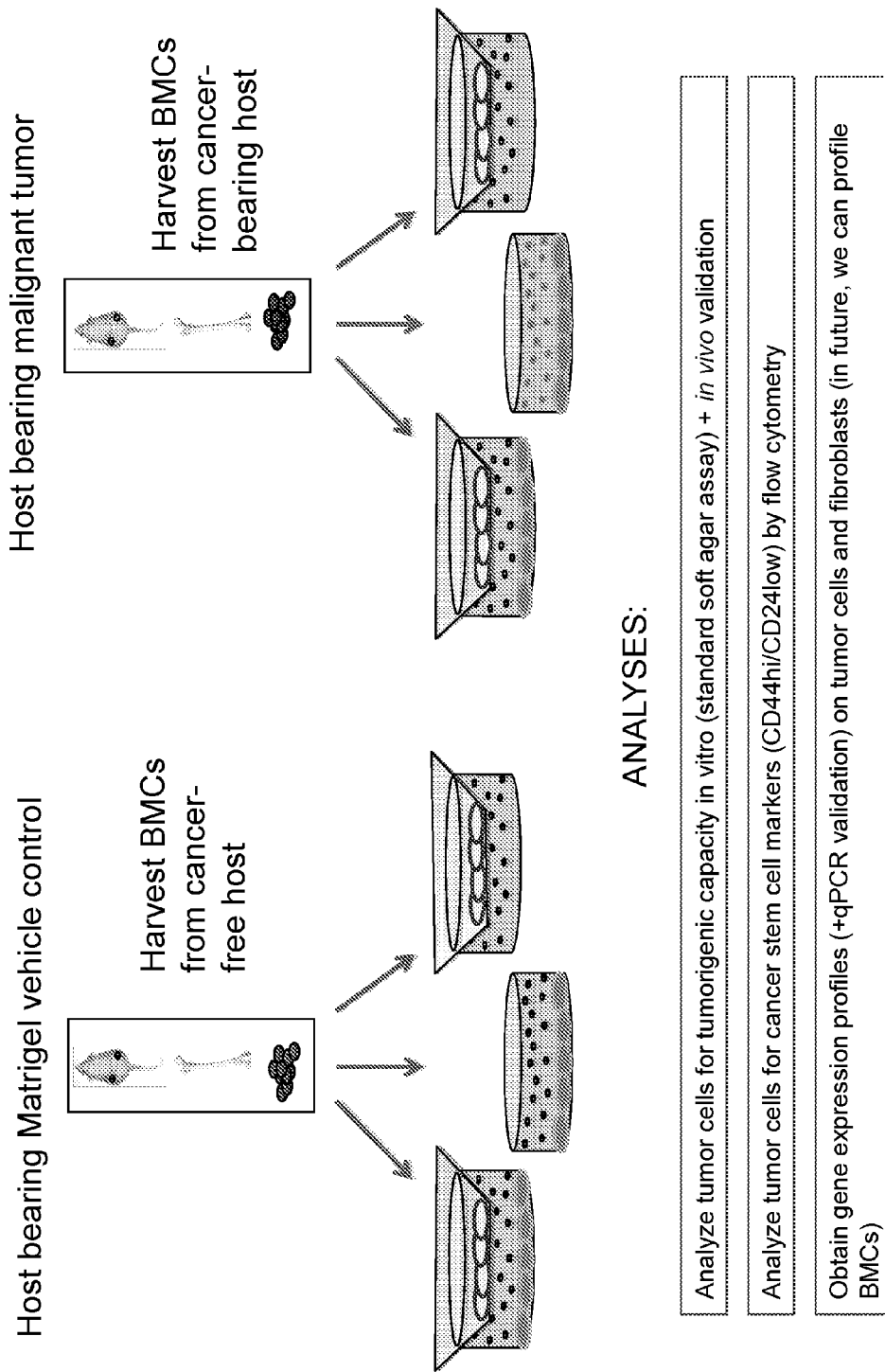
FIG. 4 shows an experimental design for using the embodiment of the in vitro cell culture system of FIG. 3.

FIG. 3 shows an embodiment of in vitro cancer cell culture test. Here, the test uses mouse derived tumor-promoting BMC and defined tumor cell lines as the reporter cancer cells for reporting the transformation from indolent to malignant states of the cancer cells. For example, HMLER-HR and BT-549. The inventors obtained a gene expression profile of these two independent tumor cell lines (HMLER-HR and BT-549) subjected to the in vitro cancer cell culture test assay (FIG. 4). In addition, a tumor-promoting BMC gene signature can be similarly generated that can then be used to predict the malignant transformation/conversion from indolent to malignant states of the cancer cells. Similarly, a tumor-promoting BMC-responsive fibroblast gene signature can be generated that can be used to define the response to tumor-promoting BMCs.

Figure 5:
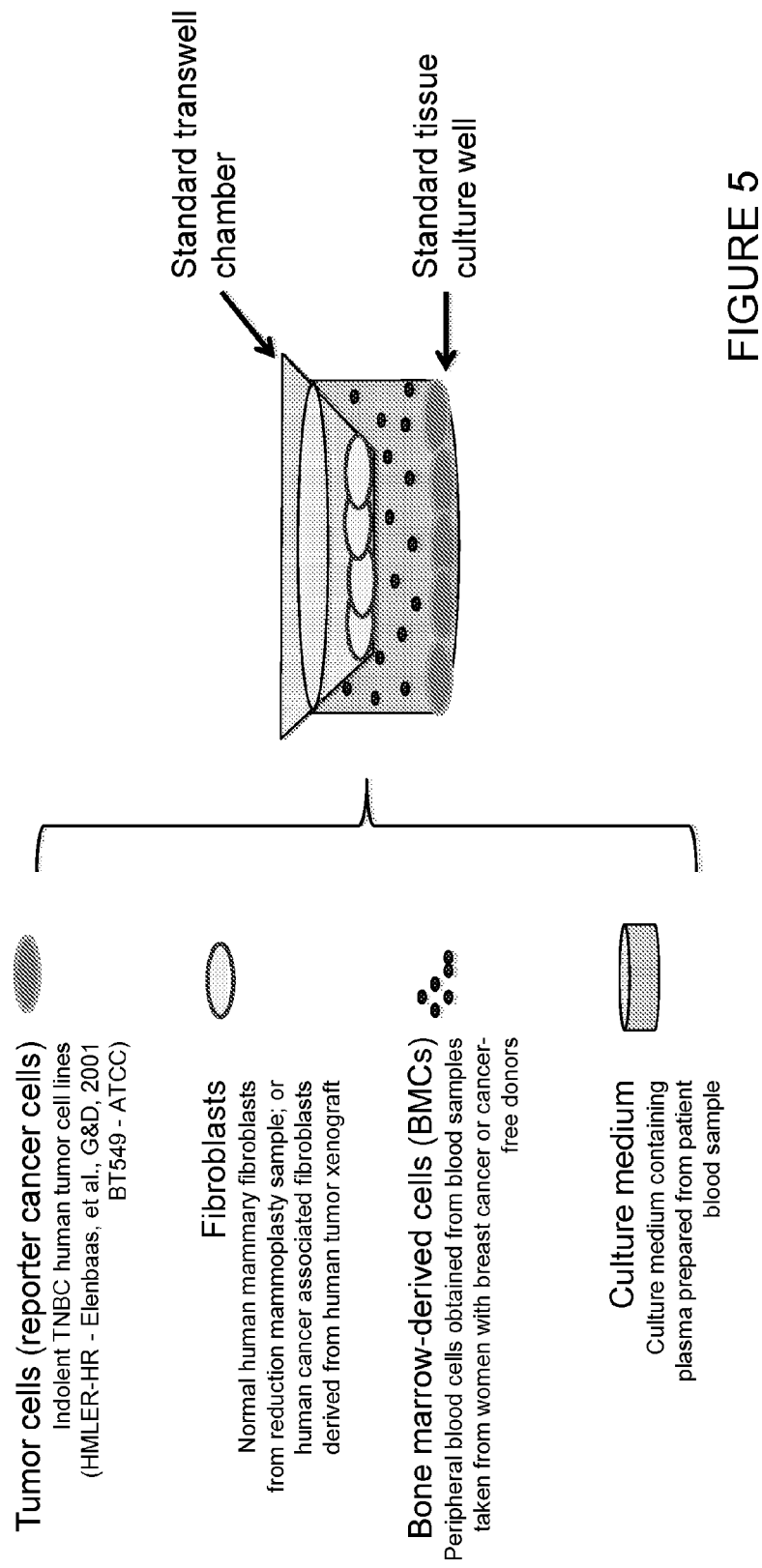
FIG. 5 is another embodiment of the in vitro cell culture system for testing the presences and also the effects of a pro-tumorigenic microenvironment showing the various components in the cell culture system. This test assay uses human-derived BMCs as the reporter cancer cell for reporting the conversion/transformation to a malignant state.

FIG. 5 shows another embodiment of in vitro cancer cell culture test. Here, the test uses human derived tumor-promoting BMC and defined tumor cell lines as the reporter cancer cells for reporting the transformation from indolent to malignant states of the cancer cells. The human-derived tumor-promoting BMC can be obtained from blood samples of healthy cancer free women and from women having been diagnosed with breast cancer.

Figure 6:
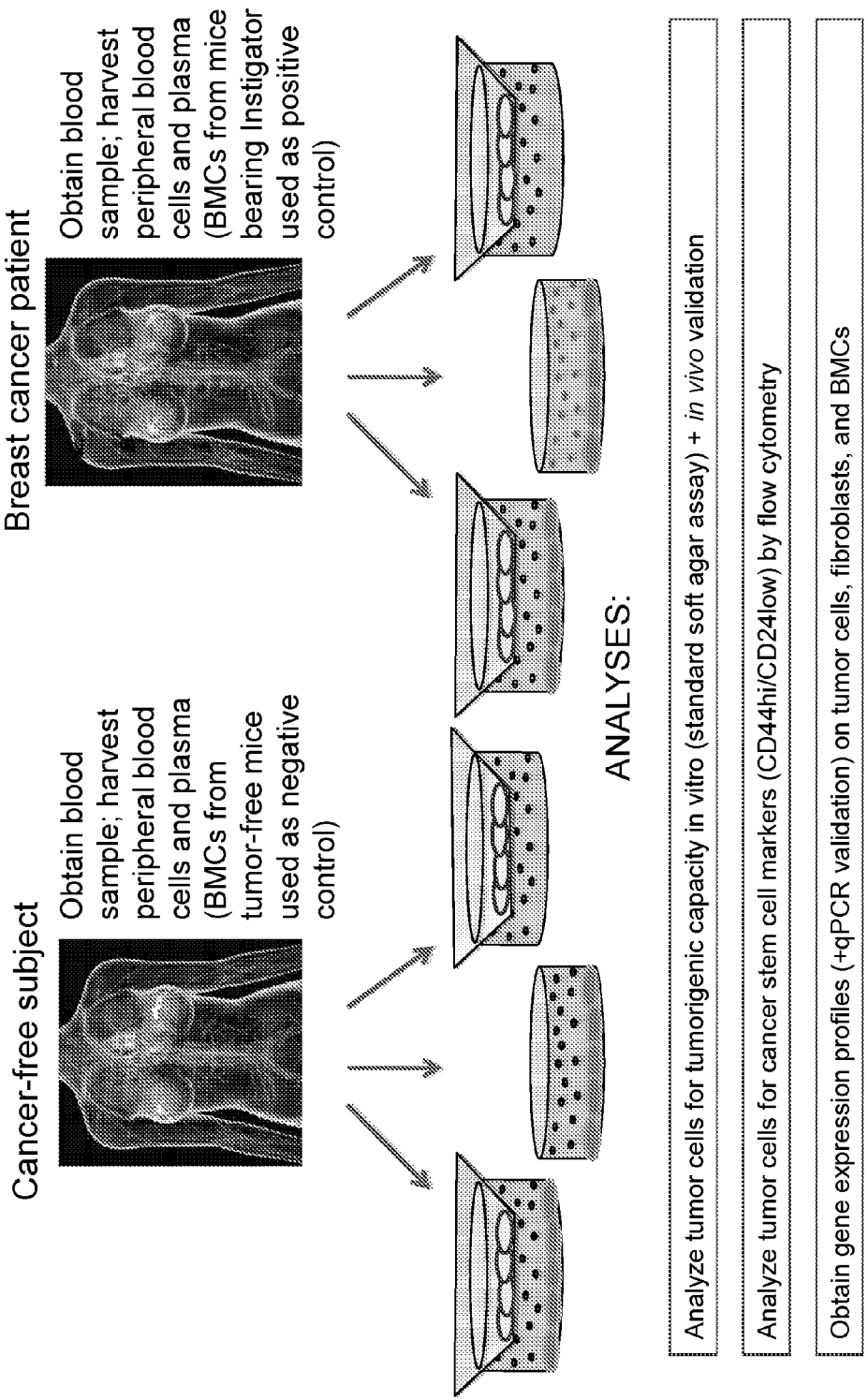
FIG. 6 shows an experimental design for using the embodiment of the in vitro cell culture system of FIG. 5.

Gene expression profiles of the reporter cancer cell lines, the human-derived tumor-promoting BMC and human-derived fibroblast cells can be generated for the uses of predicting the malignant transformation/conversion from indolent to malignant states of the cancer cells and for use in defining the response to tumor-promoting BMCs (FIG. 6).

Figure 7:
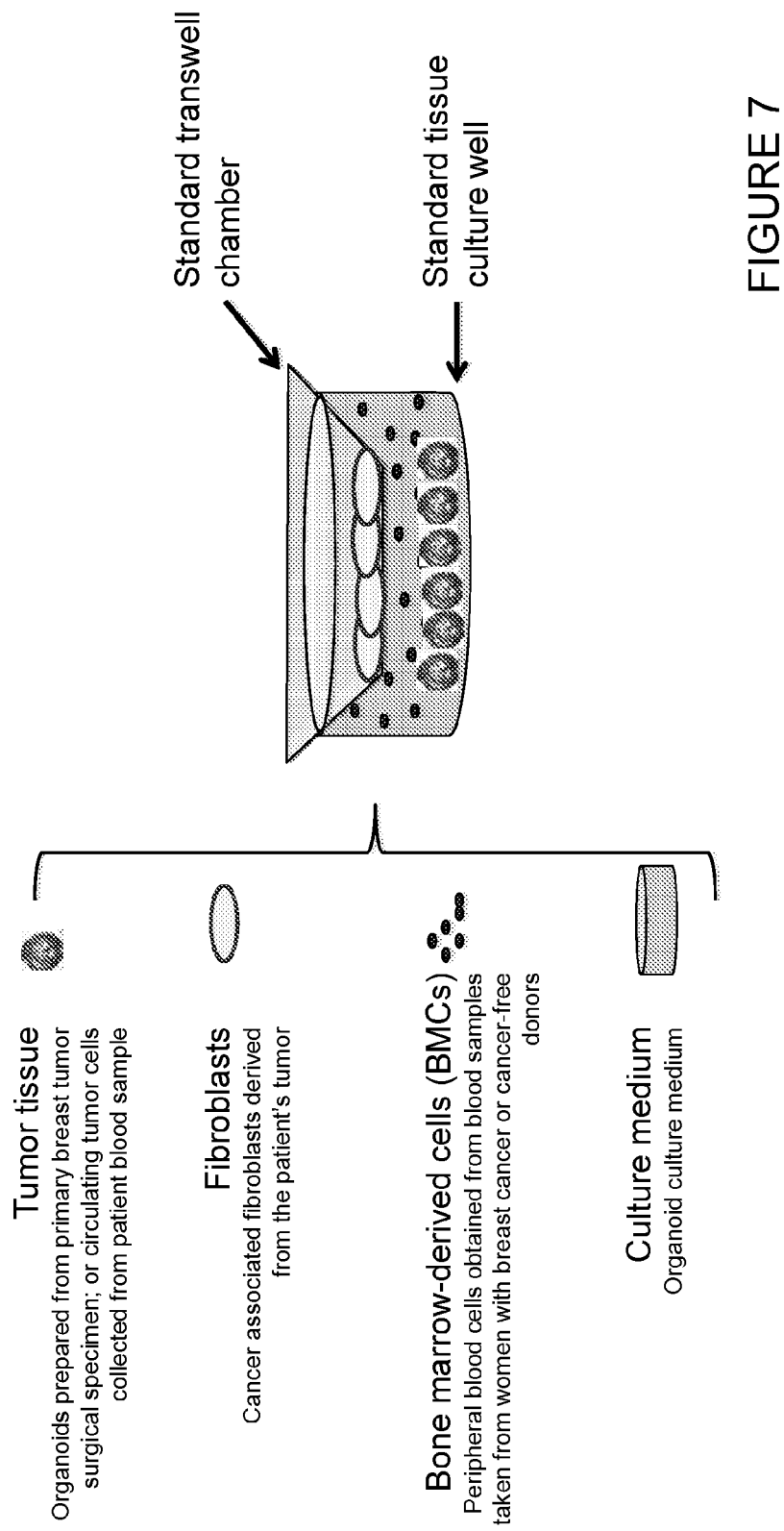
FIG. 7 is another embodiment of the in vitro cell culture system for testing the presences and also the effects of a pro-tumorgenic microenvironment showing the various components in the cell culture system. This test assay uses human-derived organoids as the reporter cancer cell for reporting the conversion/transformation to a malignant state.

FIG. 7 shows another embodiment of in vitro cancer cell culture test. Here, the test uses human derived tumor-promoting BMC and tumor-derived organoids as the reporter cancer cells for reporting the transformation from indolent to malignant states of the cancer cells. The organoids can be derived from the breast cancer patient, from the excised primary breast tumor. Methods of preparing organoids are described in Kondo, et al., (PNAS, 2011, 12; 108:6235-40). The human-derived tumor-promoting BMC can be obtained from blood samples of healthy cancer free women and from women having been diagnosed with breast cancer.

Figure 8:
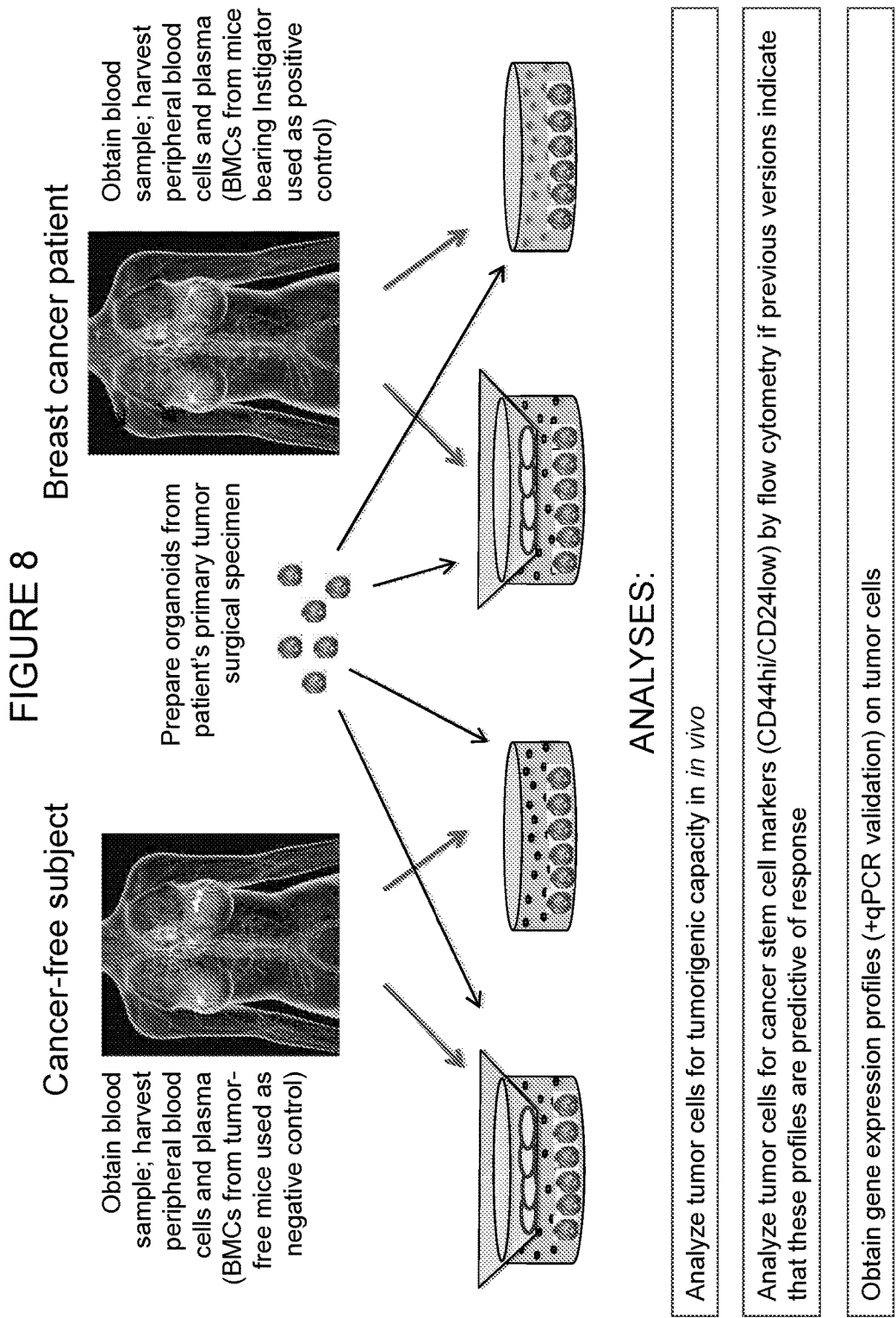
FIG. 8 shows an experimental design for using the embodiment of the in vitro cell culture system of FIG. 7.

Gene expression profiles of the tumor-derived organoids, the human-derived tumor-promoting BMC and human-derived fibroblast cells can be generated for the uses of predicting the malignant transformation/conversion from indolent to malignant states of the cancer cells and for use in defining the response to tumor-promoting BMCs (FIG. 8).

The in vitro test assay described here can be used to accurately predict whether a patient harbors a systemic environment that is amenable to the malignant conversion of indolent, clinically undetected disseminated tumor cells. For example, if a patient tests positive prior to surgery, would this patient be a good candidate for adjuvant therapy? Alternatively, if a patient tests negative in follow-up visits, but then tests positive at any subsequent time, does this indicate that the patient harbors an instigating tumor that was otherwise undetected?

Example 2—Understanding how Tumor Microenvironment Governs Breast Cancer Plasticity and Malignancy In Vitro Breast tumors are classified based on molecular and hormone receptor status. Two of these categories include triple negative (TNBC, ER−/PR−/HER2−) and luminal breast cancer (LBC, HER2+/PR+/ER+). Breast cancer recurrence rates are variable, suggesting that tumor cells disseminate from primary sites at an early stage but remain indolent for extended periods of time before progressing to symptomatic disease. It is thought that conventional therapies might select for highly malignant cells, called cancer stem cells (CSC), that are resistant to treatment and fuel tumor initiation, giving rise to secondary tumors. However, little is known about the mechanisms that cause these indolent tumors to grow into malignant disease. The inventors have previously reported that certain human carcinomas ("instigators") facilitate the growth of otherwise indolent tumor cells ("responders") located at distant anatomical sites, through the mobilization of bone marrow cells (BMCs) that will create a permissive pro-tumorigenic microenvironment, in a process called "Systemic Instigation". Based on the xenograft model the inventors here show the generation of an in vitro model that approximates in vivo instigation processes and also show that the determination of the tumorigenic ability, gene expression, and phenotypic plasticity of responder tumor populations after TNBC or LBC systemic instigation.

The inventors thus tested whether the cellular composition and plasticity of a tumor are not only dictated by the neoplasic cells that form the heart of the tumor, but also can be strongly influenced by the tumor microenvironment.

Figure 11:
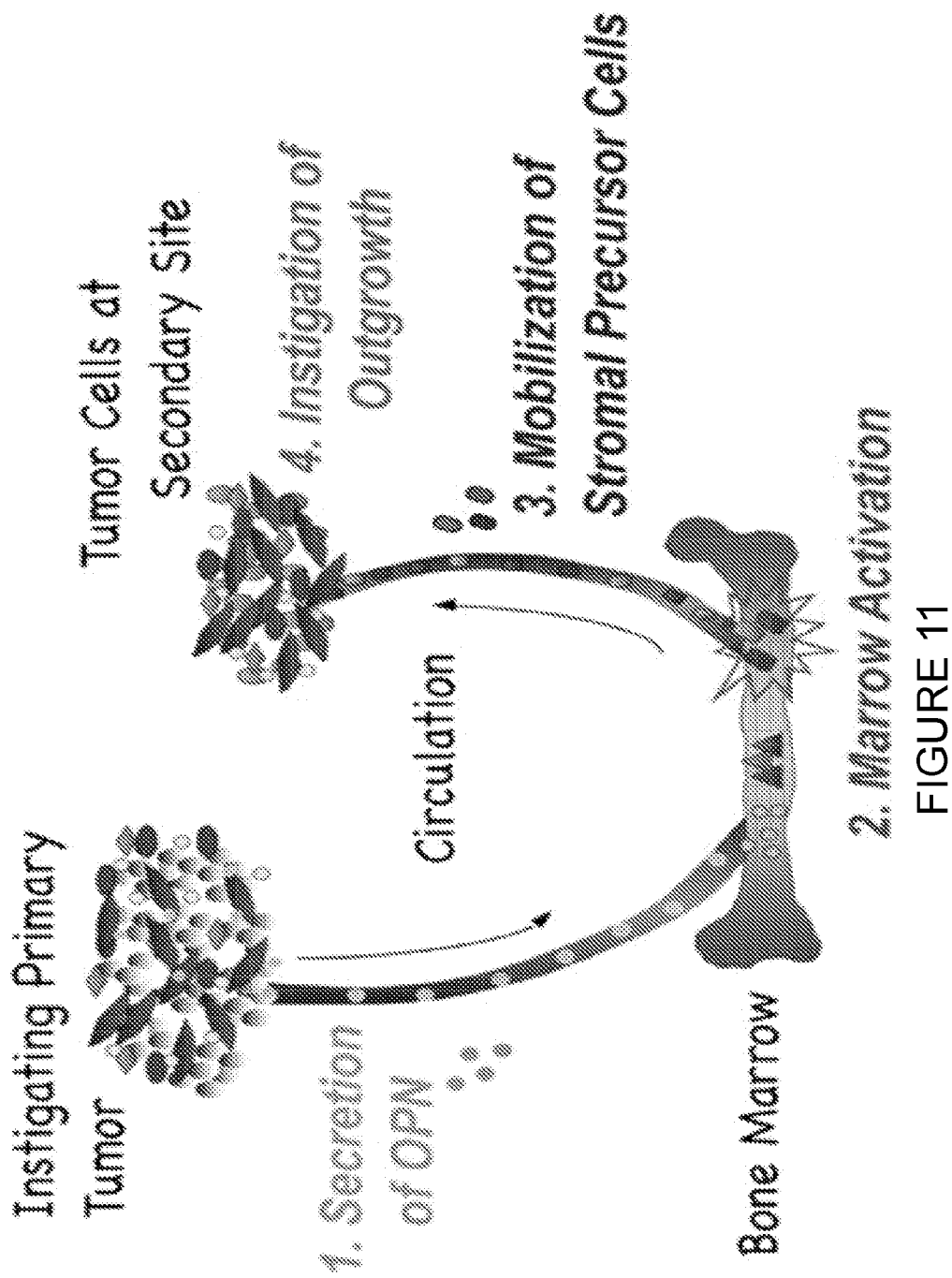
FIG. 11 shows that tumor microenvironment components are crucial regulators of cancer cell growth and homeostasis, and influence the course of tumor progression.

To isolate heterogeneous responder tumoral cells population based on single cell clones properties, fluorescence-activated cell sorting (FACs) was used to sortCD44+/CD24− population and CD44+/CD24+ population of cells. See FIG. 11.

Figure 12:
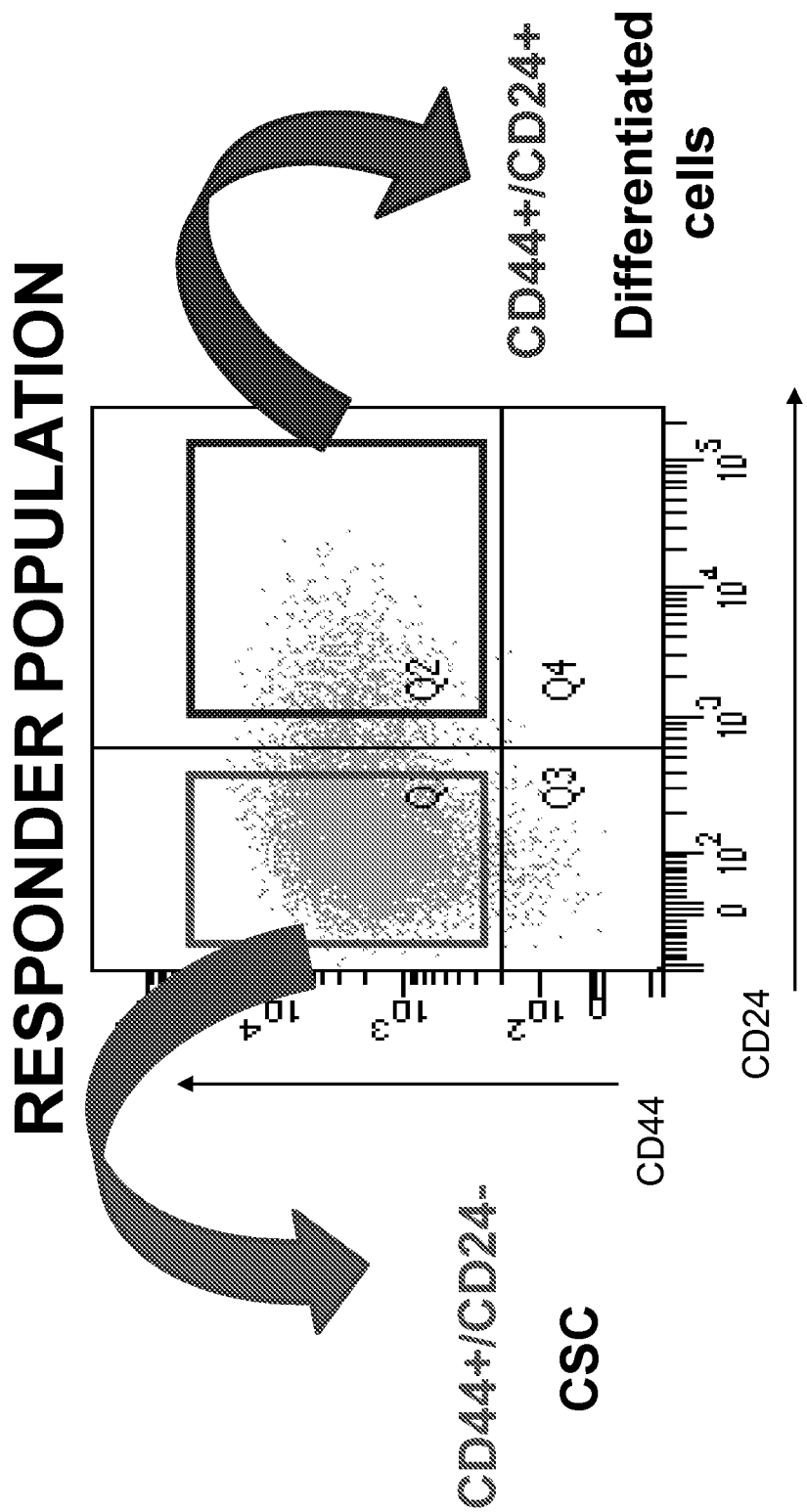
FIG. 12 shows the isolation of single cell clones (SCC): FACs sorted responder CSCs (CD44+/CD24−) and a differentiated subpopulation (CD44+/CD24+).
Figure 13:
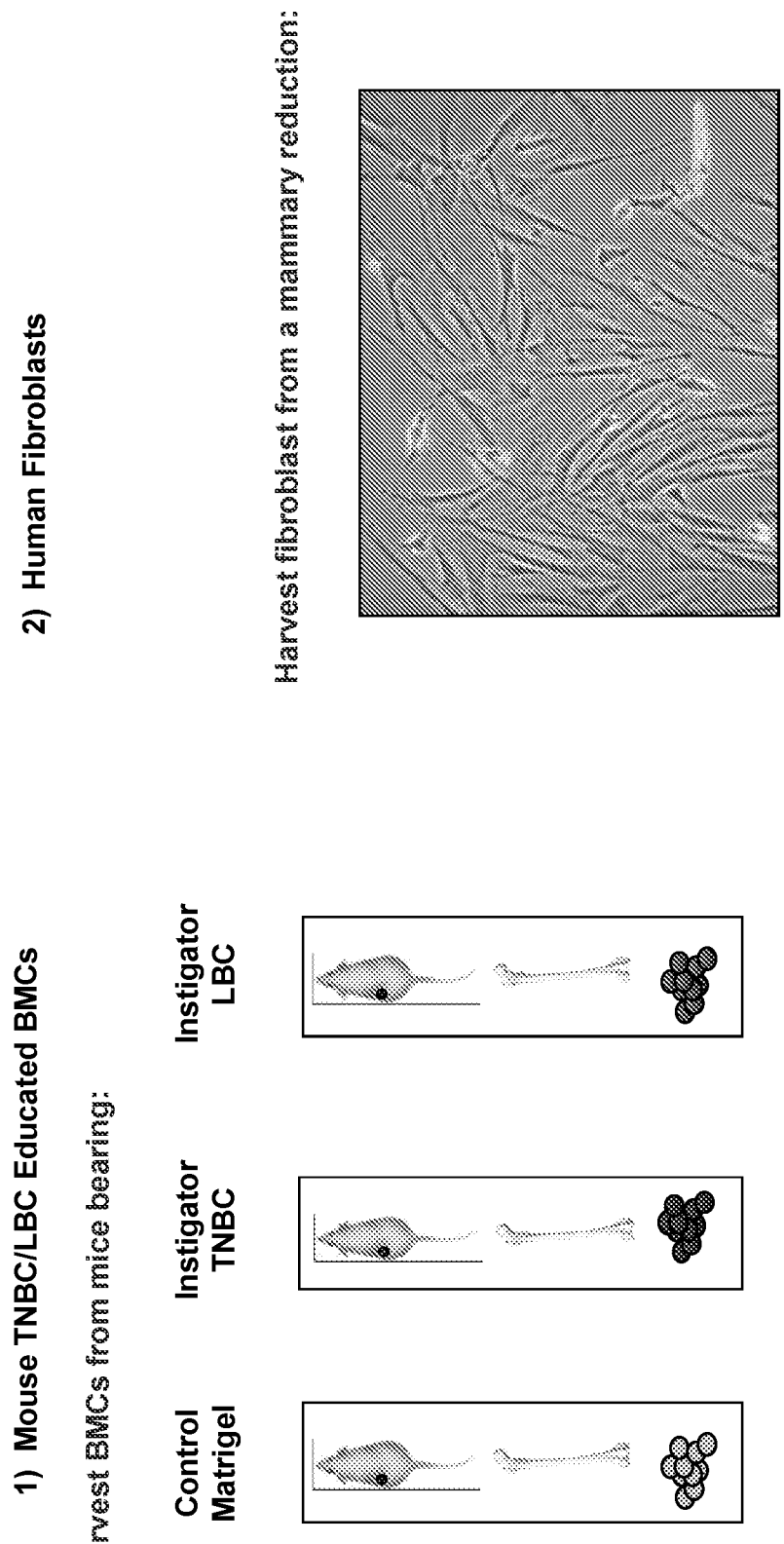
FIG. 13 shows the isolation of heterogeneous tumor microenvironment components.
Figure 14:
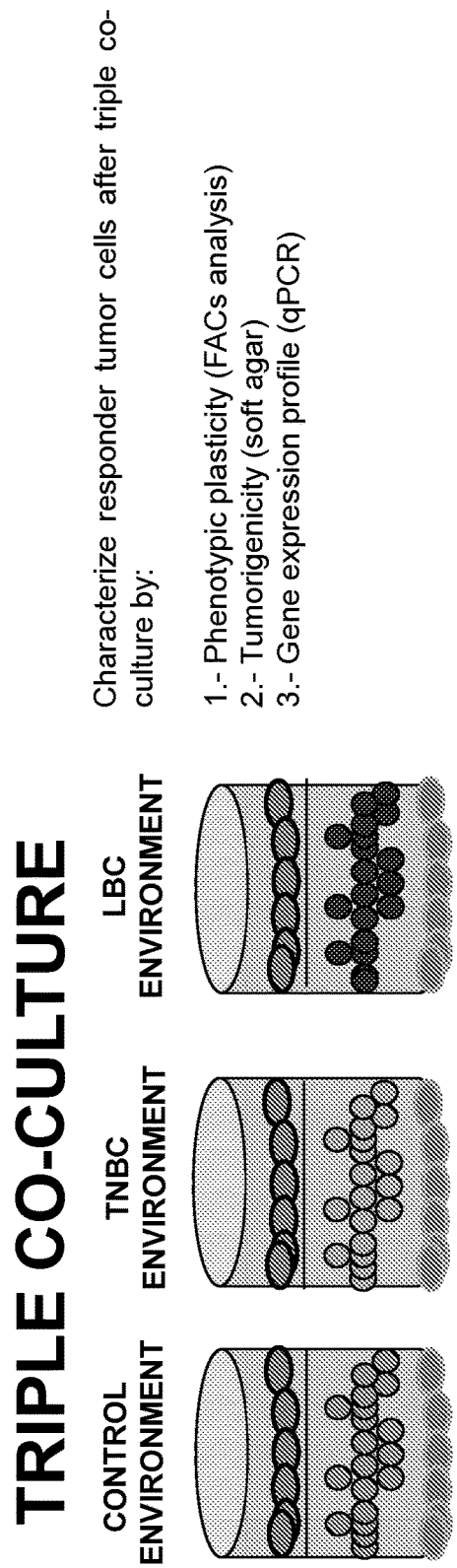
FIG. 14 shows the in vitro triple co-culture model for studying the influence of tumor microenvironment components on the conversion/transformation of indolent cancer cells.

To isolate heterogeneous tumor microenvironment components, bone-marrow derived cells (BMCs) were obtained from mice carrying either triple negative breast cancer (TNBC) xenographs, luminal breast cancer (LBC) xenographs, or just MATRIGEL® as control; and human fibroblast are harvested from human mammary reduction. (FIG. 12). Triple co-cultures of responder cancer cells, BMCs and fibroblast are assembled in a cell culture as illustrated in FIG. 13. Circulating tumoral cells isolated from peripheral blood of breast cancer patients can also be used in an embodiment of the cell culture system described here.

Figure 15:
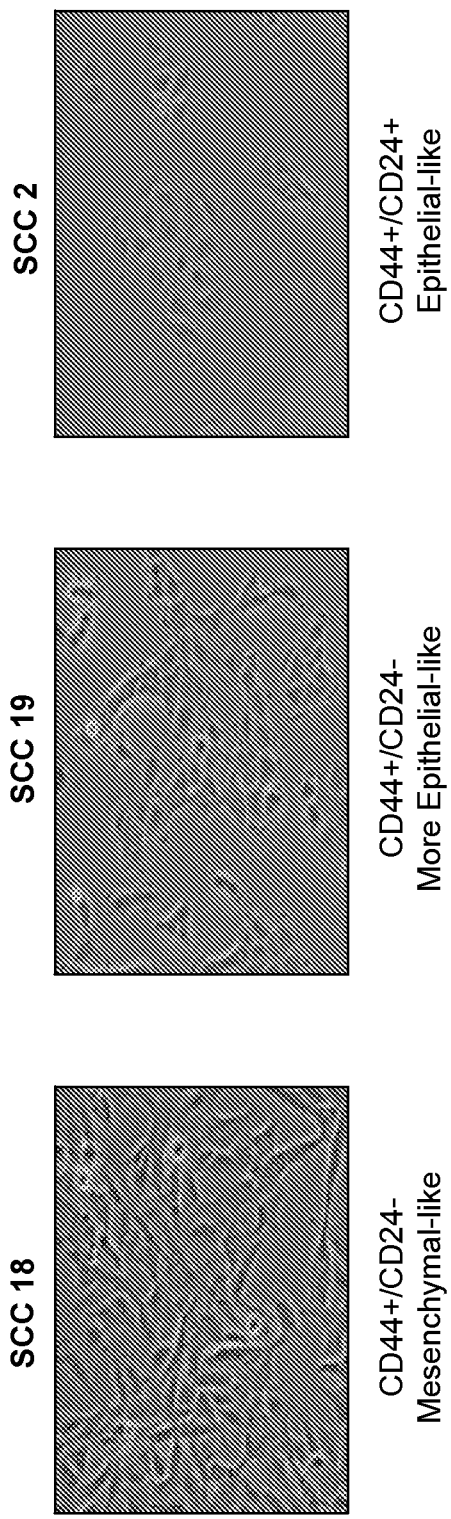
FIG. 15 shows the single cell clone morphologies of isolated responder tumoral cells.
Figure 16:
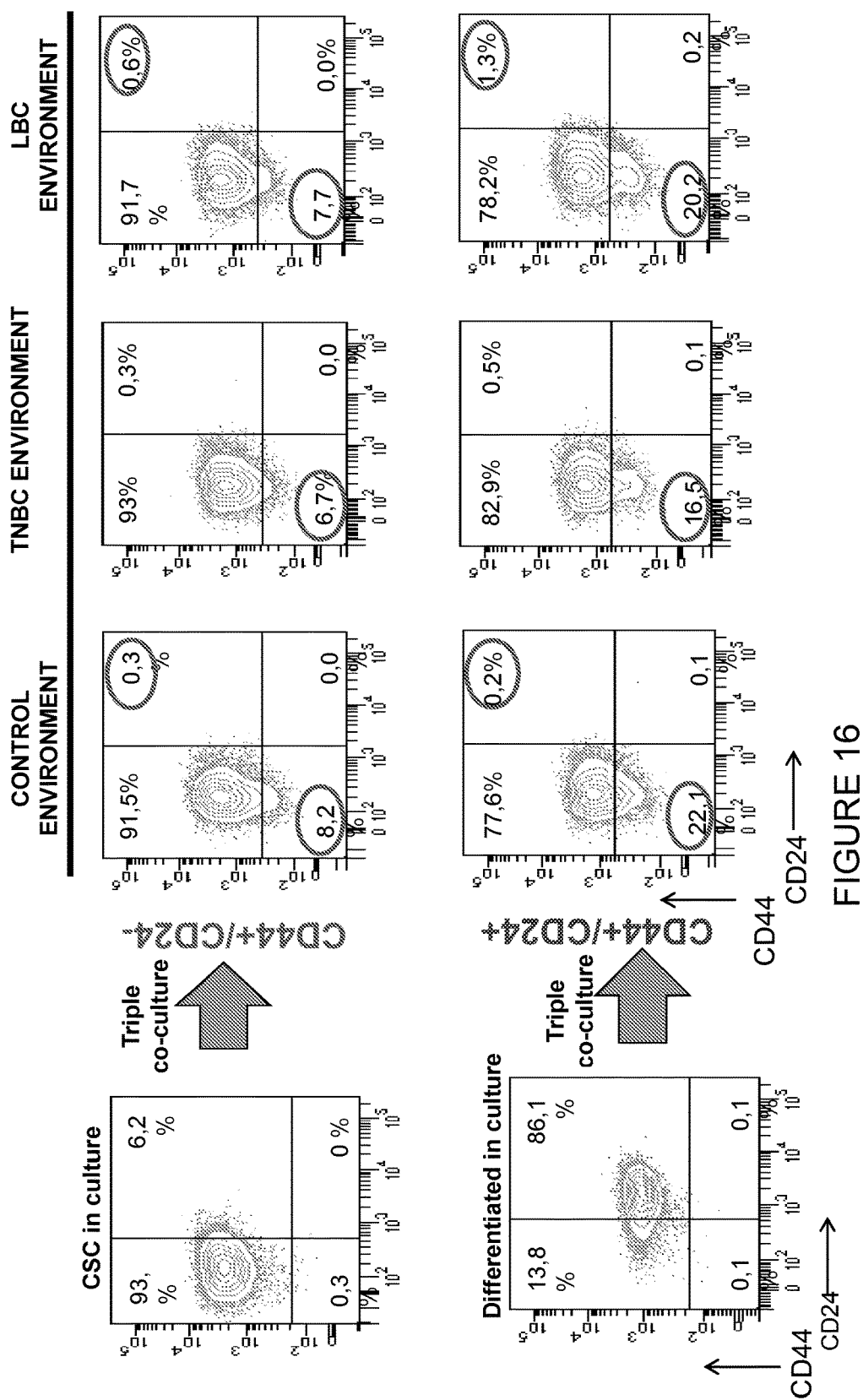
FIG. 16 shows the effects of tumor microenvironment on responder cancer stem cell (CSC) plasticity.
Figure 17:
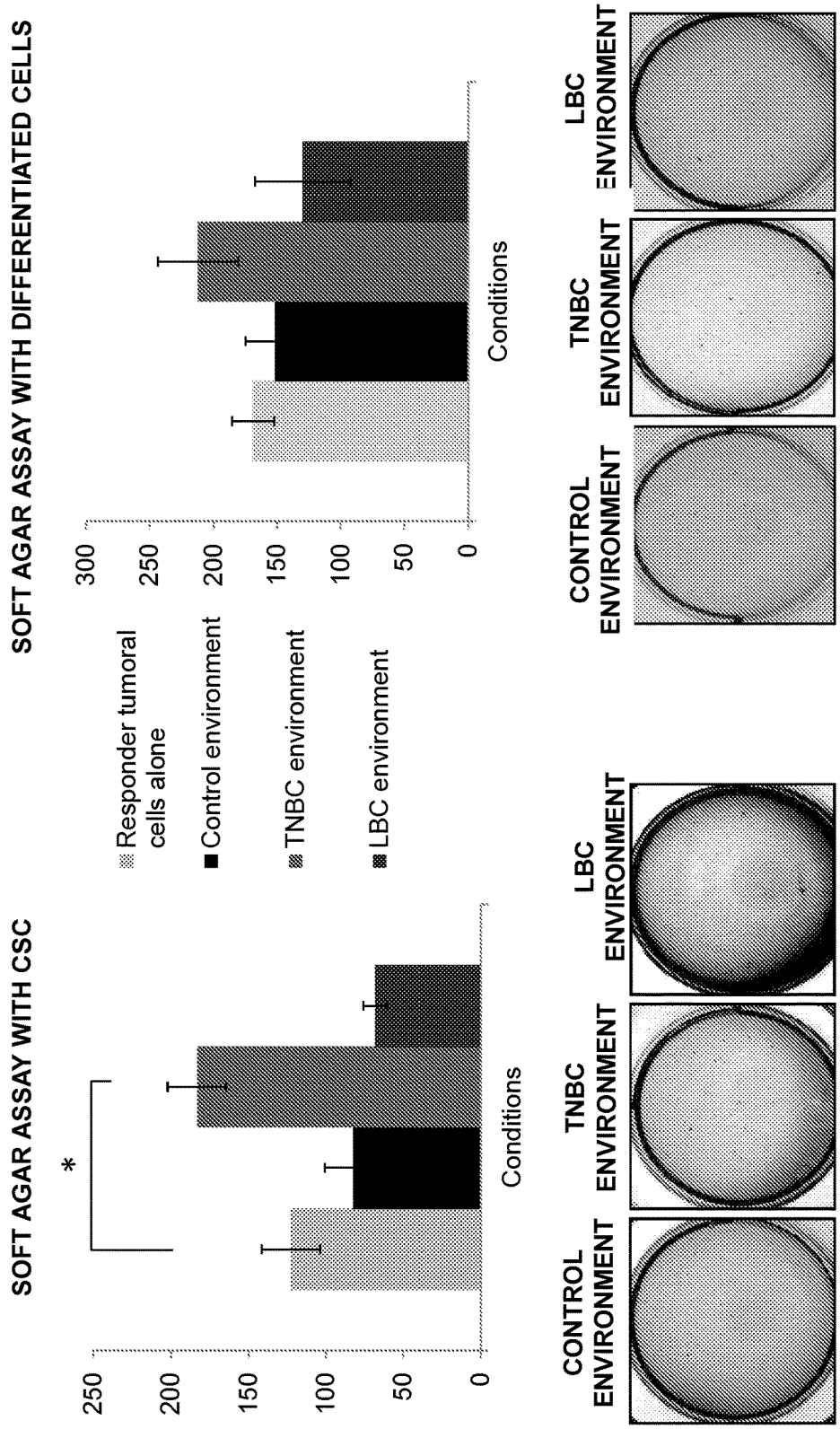
FIG. 17 shows the effects of tumor microenvironment on responder cancer stem cell (CSC) tumorigenicity.

These results here indicated that it is possible to mimic in vitro the in vivo systemic instigation model between indolent cancer cells and the tumor-promoting environment. Moreover, TNBC and LBC tumors govern the composition of the tumor microenvironment and they influence the differentiation status of responding tumors. The TNBC pro-tumorigenic microenvironment significantly increases the tumorigenicity of CSC (CD44+/CD24−), and there is a trend towards increased tumorigenicity in the differentiated population (CD44+/CD24+). See FIGS. 15 and 16. Increased tumorigenicity is also demonstrated by the standard soft agar assay (FIG. 17).

Example 3—Triple-Negative Breast Cancers Establish a Systemic Environment that Programs Malignancy Via EGF and IGF-1

Materials and Methods
Cell Lines

HMLER hygro-H-rasV12 (HMLER-HR), BPLER, and MCF7-Ras human mammary epithelial tumor cells have been previously described (Elenbaas et al., 2001; Hahn et al., 1999; ince et al., 2007; Orimo et al., 2005).

Cell Culture Conditions

HMLER-HR cells were maintained in DMEM-F12 (1:1) medium, supplemented with 5% calf serum, 10 ng/ml human recombinant EGF (Sigma E9644), 10 µg/ml insulin (Sigma 19278), 1 µg/ml hydrocortisone (Sigma 110888) and 1% penicillin-streptomycin. BPLER cells were maintained in WIT Medium (STEMGENT), and MCF7-Ras cells in DMEM media (Thermo Scientific) supplemented with 10% heat inactivated FBS (GIBCO), and 1% penicillin-streptomycin. BT549 cells were maintained in RPMI medium supplemented with 10% FBS.

Animals and Tumor Xenografts

Female Nude mice were purchased from Taconic (Hudson, N.Y.). All experiments were performed in accordance with the regulations of Harvard Medical School on Animal Care (protocol #09-12-1566). Tumor cells were injected subcutaneously into nonirradiated mice ($5 \times 10^4$ cells/mouse BPLER and $2 \times 10^6$ cells/mouse HMLER-HR or BT549). Tumor diameter was measured on the flanks of live Nude mice using digital calipers; volume was calculated as ½(length(width$^2$)).

Bone Marrow Cells and Assays

BMCs were harvested and tested for functional activity as previously described (McAllister et al., 2008). In vitro instigation assays were conducted by co-culturing 1×10$^4$ GFP-positive responder tumor cells with 1×10$^6$ BMCs harvested from mice bearing MATRIGEL, TNBC or LBC Instigators. Co-cultured cells were maintained for 4 days in BMDC medium (DMEM, 5% FBS, 5% horse serum, 10$^{-6}$ M hydrocortisone), adding fresh medium on day 2.

Immunohistochemistry and Image Analysis

Dissected tissues were fixed in 4% (wt/vol) paraformaldehyde for 24 hr, stored in 70% ethanol for 24 hr, embedded in paraffin, and sectioned onto PROBEON Plus slides (Fisher Scientific, Pittsburgh, Pa.) for immunohistochemistry using Vectastain Elite ABC kits (Vector Laboratories, Burlingame, Calif.) as previously described (McAllister et al., 2008). See Table 2 for antibodies and dilutions. Images were captured under indicated magnification with identical exposure and gain for any given experiment, using a Nikon Eclipse 901 microscope. Staining was quantified using IMAGEJ software, freely available from the National Institute of Health website.

Flow Cytometric Analysis

Freshly harvested tissues were digested in DMEM:F12 (1:1) with 1 mg/ml collagenase A (ROCHE), 1 mg/ml Hyaluronidase (ROCHE) for 30 min at 37° C. with continuous rotation. Resulting cell suspensions were dispersed with a 21 g needle, washed with resuspension buffer (2% heat-inactivated fetal calf serum in sterile HBBS), and filtered through 70 urn nylon mesh. Tissue cells and BMCs were prepared for flow cytometry by suspension in PBS containing 2% FCS, labeled with appropriate antibodies for 30 min at 4° C., and analyzed on a FACSCanto 11 (FACSDIva software 5.02; BD Bioscience). Dead cells were excluded using Live/Dead Fixable Aqua cell stain (LNVITROGEN). See Table 2 for antibodies and dilutions.

Real Time PCR

RNA was extracted from cells or snap-frozen tissues using Trizol reagent following manufacturer's instructions (INVITROGEN). RNA was retrotranscribed with ProtoScript AMV First Strand cDNA Synthesis Kit (New England BioLabs). PCR amplification was performed on a ABI Prism 7900 sequence detector using SYBR-Green (Applied Biosystems). Analysis was done using delta-delta Ct method, normalizing first to GAPDH. See Table 1 for primer sequences.

Human Breast Tumor Specimens

Primary breast tumors were collected in compliance with a protocol approved by the Brigham and Women's Hospital (IRB 93-085). Each tumor was analyzed for hormone receptor (ER/PR/HER2) status and used for these studies without any patient identifiers. Shortly after resection, tumor specimens were cut into 3-4 mm pieces, washed in RPMI, and frozen in RPM!+10% DMSO. For xenografts, tumor specimens were quickly thawed at 37° C., washed 3 times in RPMI, and minced finely into <1 mm organoids to ensure homogeneity of viable tumor tissue or non-tumor areas. Organoids were divided into equal portions, transferred to individual wells of a 96-well plate, covered with 50% MATRIGEL in RPMI media, and incubated for 10 minutes at 37° C. Organoids were surgically implanted beneath the skin of Nude mice following sterile surgical procedure.

EGFR/IGFR Inhibitors

For each administration, the EGFR inhibitor, erlotinib (LC Laboratories, 100 mg/kg) and IGFR inhibitor, BMS-754807 (ACTIVEBIOCHEM, 50 mg/kg), were freshly dissolved in 80% DMSO in PBS. Drugs or DMSO/PBS vehicle control were administered by oral gavage once daily for a period of 7 days.

Tissue Microarray

A breast carcinoma tissue microarray was purchased (BR953 Tissue Microarray, US BIOMAX, Inc.) which comprised of 30 cancer patient samples spotted as duplicated cores, 9 cases included matched samples of lymph node metastases, of which 8 cases were included in the analysis, due to the fact that one of these cases was from a male patient. Array formatting and limited clinicopathological information is available online at BIOMAX website under arrays of breast tissue #BR953. The protocol followed for immunofluorescence has been previously described (McAllister et al., 2008). In order to unmask antigen, sections were boiled twice in Citrate Buffer 10 mM pH6 for 3 min. See Table 2 for antibodies and dilutions. Images were captured under indicated magnification with identical exposure and gain for any given experiment, using a Nikon Eclipse 90i microscope.

Soft Agar Tumorigenesis Assays

1×10$^4$ Responder HMLER-HRgfp tumor cells were plated in a 6-well plate and incubated DMEM/F12 Media (1:1) supplemented with 5% heat inactivated calf serum±20 ng/ml EGF for 4 days. Positive controls were generated using 1×10$^4$ HMLER-HRgfp tumor cells, or BPLER cells in their complete media. After four days, cells were tripsinized and dispersed with a 21 g needle. 1×10$^3$ dispersed cells were embebed in 0.4% soft agar dissolved in DMEM/F12 Media with 5% heat inactivated calf serum±20 ng/ml EGF, and ±10 pg/ml of Insulin. 0.4% soft agar containing cells was deposited onto a basement of 0.6% soft agar, dissolved in the same medium. Cells were incubated for two weeks at 37° C. To analyze number of colonies, MTT 1 mg/ml dissolved in acetone/PBS (1:1), was added into each well, incubated for 4 hours and stopped the reaction with DMSO. Colonies were photographed on day 14 and counted using IMAGEJ software.

Gene Expression Array and Computational Analysis

Gene expression array analyses were previously performed on cell types known to comprise or represent stromal components of responding tumors exposed to the TNBC instigating systemic environment. These data were previously published (Elkabets et al., 2011) and deposited into GEO, and heatmaps were generated from these data. The first data set includes expression analysis of cancer-associated fibroblasts isolated from human mammary tumor xenografts (CAF), gran ulin-treated human mammary fibroblasts (PRGRN) analyzed relative to PBS-treated human mammary fibroblast controls (CTRL) (GEO GSE25620). The second data set includes gene expression analysis of Sca1+ cKit− BMCs from mice bearing instigating TNBC tumors (instigator) relative to MATRIGE1 control (MATRIGEL) (GEO GSE25619). Smyth's moderated t-test had been used to identify differentially expressed genes; to test for enrichments of higher- or lower-expressed genes in data sets, we had used RenderCat program, which implements a threeshold-free technique with high statistical power based on Zhang C statistic (Elkabets et al., 2011). Our current analyses were motivated by interrogation of these data sets for genes that met the following criteria: 1. secreted protein products, 2. cytokines known to regulate malignancy profile factors, 3. factors involved in recruitment of BMCs.

Statistical Analysis

Data are expressed as mean±SEM. Data were analyzed by Student's t test and were considered statistically significant if $p \leq 0.05$.

Results

Figure 18:
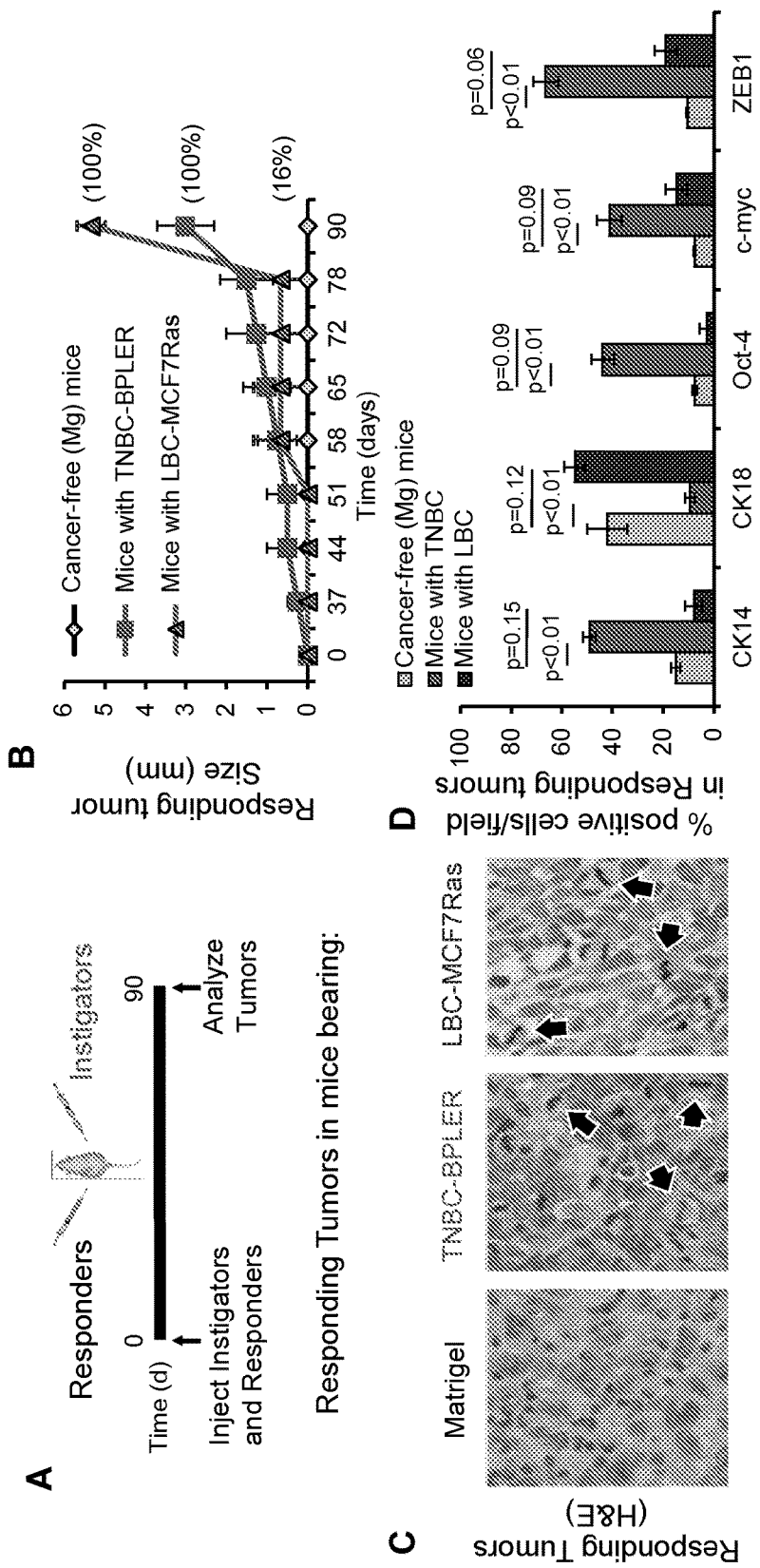
FIG. 18A-18D. The systemic environment determines histopathological and malignant properties of otherwise indolent tumors.

Breast Cancer Subtype-Specific Systemic Environments Program Distant Tumor Malignancy It was previously determined that certain aggressively growing breast cancers ("instigators") facilitate the growth of otherwise indolent disseminated tumors ("responders") through a processes termed "systemic instigation" (McAllister et al., 2008). Instigating tumors establish a pro-tumorigenic systemic environment by activating and mobilizing bone marrow cells that instruct formation of a tumor-supportive desmoplastic microenvironment in sites where the indolent disseminated tumors reside (Elkabets et al., 2011). In order to understand how systemic processes directly impact malignancy, responding human breast cancer cells were injected contralaterally to instigating breast tumors or MATRIGEL vehicle control into nude mice, thereby representing situations in which a patient either has co-existing primary and distant metastases, contralateral breast cancer, or more than one disseminated metastatic foci (FIG. 18A). For these experiments, triple-negative HMLER hygro-H-rasV12 (HMLER-HR) tumor cells (Elenbaas et al., 2001) were used as responders and either oncotype-matched BPLER triple-negative tumor cells (Ince et al., 2007) or MCF7Ras luminal breast cancer cells (Orimo et al., 2005) as instigators.

Responding cells exposed to the TNBC-induced systemic environment formed tumors in 100% of the mice following a latency period of ~35 days, after which they maintained a constant rate of growth (FIG. 18B). At the experimental end point, these responding tumors were 3-fold larger than those that had been injected opposite MATRIGEL, which formed a necrotic tumor in only 1 of the 6 mice (FIG. 18B, 18C). Likewise, responding cells formed tumors in 100% of the mice bearing a systemic environment established by LBC; these tumors demonstrated a latency of ~50 days and mirrored the growth pattern of the instigating LBC tumors for ~80 days, at which point they demonstrated a marked acceleration in their growth rate. At the experimental end point, the LBC-induced tumors were 5.3-fold larger than the control responding tumor tissues (FIG. 18B).

The responding tumors that had grown in the TNBC systemic environment displayed a wide spectrum of pathological grades from atypical/high grade to differentiated/low grade, were moderately mitotic, and in all instances, there was no observable necrosis (FIG. 18C). As it was observed previously (Elkabets et al., 2011), these responder tumors were infiltrated with alpha-smooth muscle actin (aSMA)-positive myofibroblasts (data not shown). In striking contrast, responding tumors that had formed in the LBC environment were highly mitotic and had areas of observable edema and necrosis (FIG. 18C). These responding tumors were extensively vascularized, without forming aSMA-rich desmoplastic stroma (data not shown), and these pro-angiogenic mechanism have been extensively characterized (unpublished observations). In both cases, responding tumor histopathology was consistent with breast adenocarcinomas observed in the clinic (Foulkes et al., 2010). Importantly, responding tumors did not incorporate cells from the distant instigating tumors, which are non-metastatic at this time point, as the "self-seeding" process appears to rely on the use of highly metastatic xenografted cell lines (Kim et al., 2009). Instigating tumors facilitate responder grew in the absence of "self-seeding". Tumor sections stained for GFP and SV-40 LgT confirmed that GFP-positive instigator cells had not metastasized to the contralateral sites of GFP-negative responder cell injection (data not shown), and were not present in the bone marrow cell (BMC) preparations used in admixture experiments (data not shown). Cell nuclei were counterstained with DAPI.

Due to their enhanced tumorigenicity when injected into instigating environments, responding tumors were examined for expression of CD44 and CD24 cell-surface antigens, which typically distinguish tumor-initiating cells ($CD44^{hi/+}$/$CD24^{lo/-}$) from the bulk population of non-stem, differentiated progeny ($CD44^{lo/-}$/$CD24^{+/hi}$) within human breast tumor populations (Al-Hajj et al., 2003). Following their injection in vivo, ~24% of the responding cells in the control, non-instigating MATRIGEL environment, displayed differentiated profiles (CD44−/CD24+), while ~20% of the population had a phenotype consistent with tumor-initiating cells (CD44+/CD24−) (data not shown). Tumor cells that had grown in the TNBC environment were significantly enriched for the tumor-initiating phenotype (~72%) (data not shown). However, despite their enhanced tumorigenicity in the LBC environment, only ~12% of tumor cells exposed to the LBC systemic environment displayed the tumor-initiating phenotype (data not shown). Interestingly, in culture, CD44+/CD24− cells comprised ~99% of the responding breast tumor cell population, while the remaining ~1% were CD44+/CD24+ differentiated progeny (data not shown). Flow cytometric analysis of responder tumor cells for the breast cancer stem cell markers CD44 and CD24 were conducted to confirm this. Therefore, despite being highly enriched for the tumor-initiating phenotype in culture, the responding cell population remained in a state of indolence in vivo and relied on systemic signals to form tumors. As a consequence of these results, we wished to know what other malignant features were underlying the response of otherwise indolent tumors to their systemic environments.

Tumor forming capacity has been associated with cells that undergo an epithelial-mesenchymal transition (EMT) (Mani et al., 2008) and together these features are predominantly observed in basal-like breast cancer subtypes (Polyak and Weinberg, 2009; Visvader, 2009). Moreover, overexpression of genes that maintain pluripotency has been correlated with high-grade basaklike breast tumors and with poor clinical' outcome (Ben-Porath et al., 2008; Wong et al., 2008). Therefore, responding tumors were interrogated for their expression of factors associated with EMT and pluripotency.

Responding breast cancer cells that had grown in the TNBC environment expressed significantly higher levels of the transcription factors Oct4 (~47%) and c-myc (~42%) than the counterpart cells in the control MATRIGEL environment, in which Oct4 and c-myc were each expressed in ~8% of the population (FIG. 18D). It was observed that the majority of c-Myc in these tumors was localized to the cytoplasm, in agreement with clinical studies of myc-amplified breast tumors, in which ~95% show cytoplasmic localization and ~12% show both nuclear and cytoplasmic localization of c-Myc (Liao and Dickson, 2000). Oct4, specifically the nuclear Oct4A isoform, plays a critical role in maintaining pluripotency and self-renewal (Nichols et al., 1998), while c-myc regulates the transcription of genes required for a range of cellular processes, including proliferation, differentiation, apoptosis, and self-renewal (van Riggelen et al., 2010). The transcription factor Zeb1 was expressed in the nucleus of ~67% of TNBC-responsive tumor cells, as opposed to only ~10% of responder cells in the control environment (FIG. 18D). Zeb1 induces EMT, inhibits luminal differentiation, and is expressed predominantly in triple-negative human breast cancers (Moreno-Bueno et al., 2008; Sarrio et al., 2012; Scheel et al., 2011).

Analysis of the same responding breast tumor cell population, when implanted into the LBC systemic environment, revealed that only 2% of the responding tumor cells expressed Oct4, ~17% expressed c-myc, and ~19% showed detectable levels of nuclear Zeb1 (FIG. 18D). These expression levels were significantly lower than those of responding tumors in the TNBC environment and not significantly different from those in the control environment (FIG. 18D).

In the absence of systemic stimuli, the responding tumor cell population expressed both the luminal cytokeratin, CK18, (~42%) and the basal cytokeratin, CK14 (~15%) (FIG. 18D). Responding tumors that had grown in the TNBC systemic environment were enriched for the basal phenotype, whereby 50% of the cells expressed CK14 and ~10% were CK18 positive (FIG. 18D). Conversely, the epithelial responder cells that formed tumors in the LBC systemic environment were enriched for cytokeratin CK18 (~55%), with a lesser contribution of CK14-positive cells (~8%) (FIG. 18D).

Hence, the same starting population of otherwise indolent tumor cells exhibited a significant degree of plasticity in response to breast cancer subtype-specific systemic signals. Specifically, the TNBC systemic environment programmed responder cells to adopt a malignancy profile defined collectively by expression of basal cytokeratins, tumor-initiating cell features (CD44+/CD24−) and factors regulating maintenance of pluripotency (Oct-4 and c-Myc), and epithelial-mesenchymal transition (Zeb1). LBC instigation on the other hand, gave rise to highly proliferative responding tumors that were enriched for cells expressing luminal cytokeratins and CD24.

Acquisition of the Malignancy Profile is an Early Event in TNBC-Induced Systemic Instigation The results indicated that instigating TNBC and LBC tumors established different systemic environments, each of which impinged upon distant tumor histopathology and malignancy in different ways. For TNBC-mediated systemic instigation, it was noted that patients with metastatic TNBC tend to experience early recurrence and there are currently no effective treatment options for them other than harsh cytotoxic chemotherapy.

When otherwise indolent tumor cells are injected into mice in which TNBC tumors have been growing for 30 days, responding tumors initiate growth immediately, without requiring a long latency period (McAllister et al., 2008). This protocol with GFP+ responding tumor cells was therefore used to test responding tissues after 8 days, when all tissue plugs recovered opposite MATRIGEL were of comparable size to those recovered opposite TNBC (FIG. 19A, B). αSMA-positive myofibroblasts were already evident in the responding tumors that had been exposed to the TNBC systemic environment for 8 days (data not shown), thus confirming that a hallmark of systemic instigation—stromal desmoplasia—had been initiated. Responding tumor cells expressed both luminal and basal cytokeratins under both MATRIGEL and TNBC conditions (data not shown), indicating that enrichment for CK14 was not an early event in the TNBC-mediated response.

By histopathological analysis, enrichment of the malignancy profile factors (Oct4, c-myc, Zeb1) was apparent in the responding tumors after 8 days of exposure to the TNBC-induced systemic environment compared with MATRIGEL controls (data not shown). Likewise, ~52% of the responder cells retained CD44+/CD24− status in the TNBC environment while—83% had acquired the differentiated phenotype CD44+/CD24+ in the MATRIGEL environment (data not shown).

Figure 19:
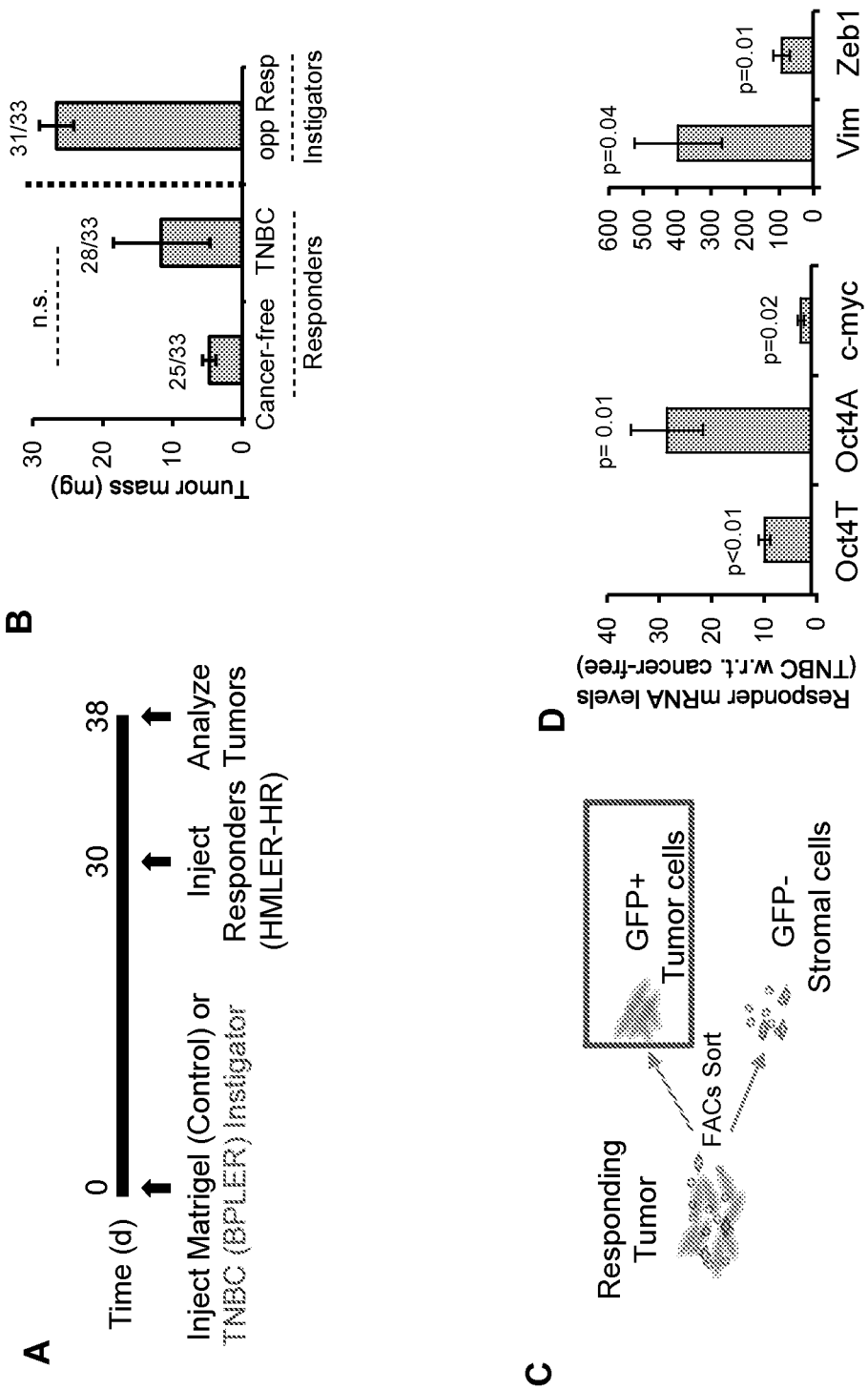
FIGS. 19A-19D. Systemic Modulation of Malignancy Profile Genes Occurs Early in Responding Tumor Instigation.

The gene expression levels of the malignancy factors were also analyzed in FACS sorted GFP+ responding tumor cells prepared from the resulting tumors (FIG. 19C). Relative to MATRIGEL environment controls, GFP+ responding tumor cells that had grown in the TNBC instigating environment had significantly higher expression levels of Oct-4A ~29-fold), c-myc ~3-fold), and Zeb1 (~93-fold) (FIG. 19D). Expression of the mesenchymal marker, vimentin (VIM), was also significantly elevated ~397-fold) in the TNBC-instigated tumors, than in the control responding tumor cells (FIG. 19D). These data thus confirmed the conclusions from the histopathological analyses.

Like the responding HMLER-HR TNBC cells, which are driven by oncogenic Ras, BT-549, a poorly growing TNBC cell line (Basal B subtype) that carries mutations in p53 and Rb1 (Kenny et al., 2007), acquired a proliferation advantaged and displayed the malignant profile following 8 days of exposure to the TNBC environment, which were not apparent in the MATRIGEL environment (FIG. 25A-25C). Consequently, the BT549 tumors maintained long-term growth in the TNBC instigating environment but not in the MATRIGEL environment (FIG. 25D).

Collectively, these results demonstrated that response to the TNBC-induced systemic environment was not oncotype dependent and that programming of responding tumor cell malignant features was an early event during systemic instigation.

Figure 20:
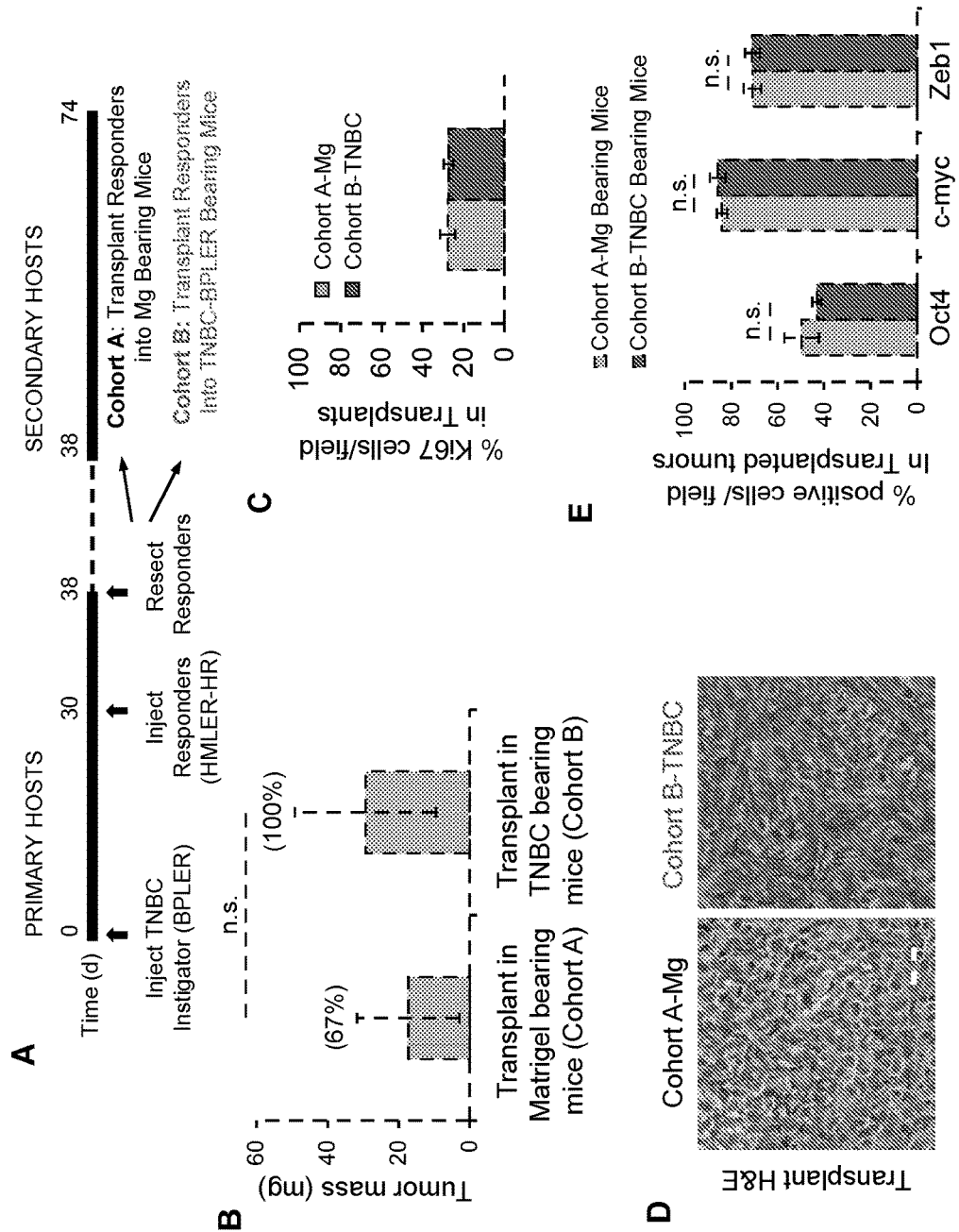
FIGS. 20A-20E. Responding Tumors Retain Malignancy after Short Term Exposure to the Instigating TNBC Environment.

Early Activation of the Malignancy Profile is Consequential for Disease Progression While the malignancy profile was apparent during the course of responding tumor growth under TNBC instigating conditions, it is not known if its sustained manifestation was due to the continuous presence of the instigating TNBC tumor. For this reason, the ability of responding tumors to progress independently of the TNBC instigating tumors were tested. To do so, responder were surgically removed plugs after 8 days of exposure to the TNBC environment, immediately transplanted them into secondary hosts bearing either MATRIGEL or a TNBC tumor, and allowed them to progress for 5 weeks (FIG. 20A). It was chose to The responders were selected for transplantation instead of the instigators in order to avoid minimal residual disease.

After 5 weeks, the percentage of Ki67+ proliferative cells and the average mass of responding tumors was the same in both cohorts of secondary hosts (FIG. 20B, C). Responding tumors from both cohorts were also nearly identical on the histopathological level (FIG. 20D) and maintained an activated stroma, characterized by the presence of aSMA+ myofibroblasts (data not shown). Likewise, transplanted responding tumors in both cohorts maintained the CD44+/CD24− phenotype and displayed equivalent expression of Oct4, cmyc, and Zeb1 malignancy profile factors (FIG. 20E).

These results demonstrated that systemic events that occurred during the initial phases of instigation by TNBC were sufficient for responding tumors to maintain the malignancy profile, perhaps due to the maintenance of reactive stroma, continued recruitment of tumor-supportive BMCs, or both. To explore one of these possibilities, responding tumors were analyzed for the expression of osteopontin (OPN), a tumor-derived cytokine necessary for rendering BMCs pro-tumorigenic (McAllister et al., 2008) and a target of the Oct4 transcription factor (Botquin et al., 1998; Guo et al., 2002). It was observed that OPN levels in responding tumors exposed to the control, non-instigating environment were virtually undectable (data not shown). However, the responding tumors that were exposed to the TNBC environment for 8 days and transplanted into secondary host bearing MATRIGEL or TNBC instigators alike, expressed readily detectable, elevated levels of OPN protein, that were comparable to that of the instigating tumors upon visual examination (data not shown). These results suggested that once programmed by the TNBC-dependent macroenvironment, responding tumors might be capable of supporting their own growth by activating pro-tumorigenic BMCs.

Identification of TNBC-Induced Stromel Factors

Figures 26A, 26B, 26C:
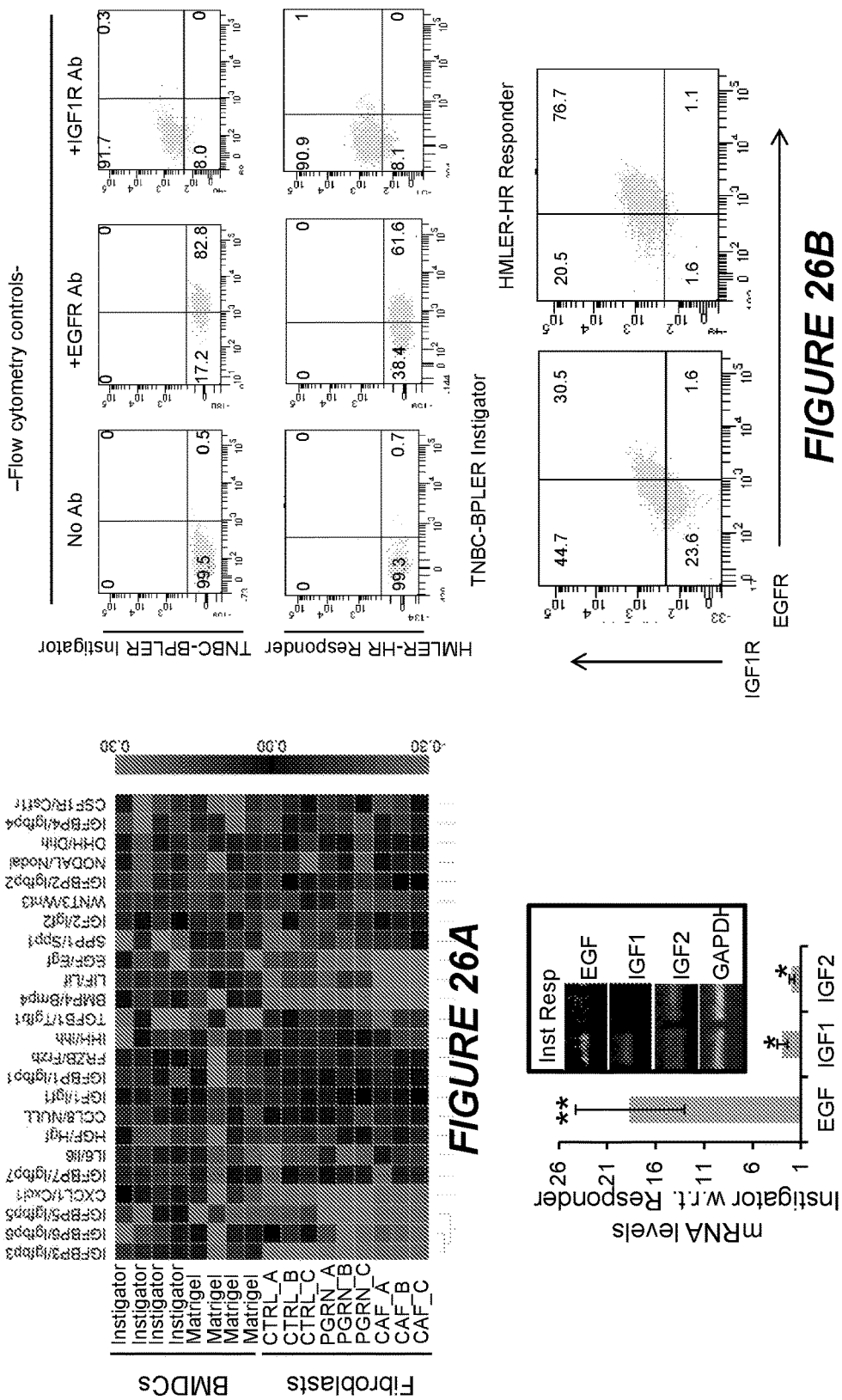

The results indicated that exogenous factors provided by the responding tumor cell microenvironment, as mandated by the host systemic macroenvironment, were responsible for responding tumor malignancy in vivo. Due to limited material from control, non-instigated tissue, comparative gene expression profiling of responding tumor stroma was not possible. Therefore, in order to identify candidates, we analyzed gene expression profiles of components that we previously determined comprise and/or define responding tumor stroma (Elkabets et al., 2011). These include: 1) pro-tumorigenic bone marrow derived cells from mice bearing TNBC tumors (GEO GSE25620); 2) cancer-associated fibroblasts derived from human tumor xenografts; and 3) granulin-treated human mammary cancer-associated fibroblasts (GEO GSE25619). From these data sets, we selected genes that met the following criteria: 1) protein products that are secreted; 2) cytokines known to regulate self-renewal, transdifferentiation, and EMT (i.e., malignancy profile features); and 3) factors that are involved in recruitment of pro-tumorigenic BMCs. This process generated lists of genes (FIG. 26A) from which we selected the most differentially expressed genes from each of the 3 different stromal components relative to their respective controls, resulting in a combined list of genes that motivated subsequent analysis.

Figure 21:
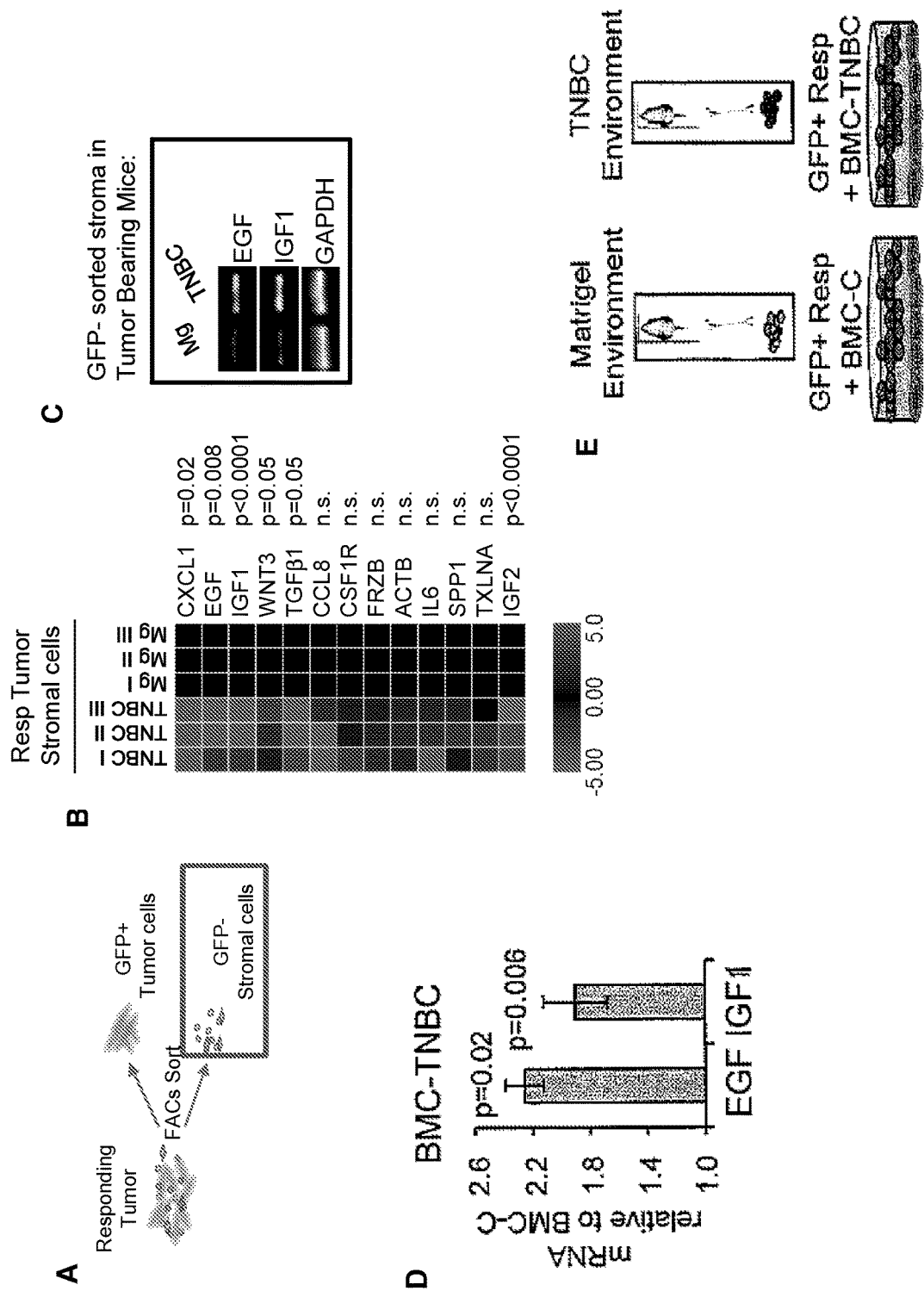
FIGS. 21A-21J. TNBC-Induced Tumor Microenvironment Express EGF and IGF-1 and Drives the Malignancy Profile.
Figure 21:
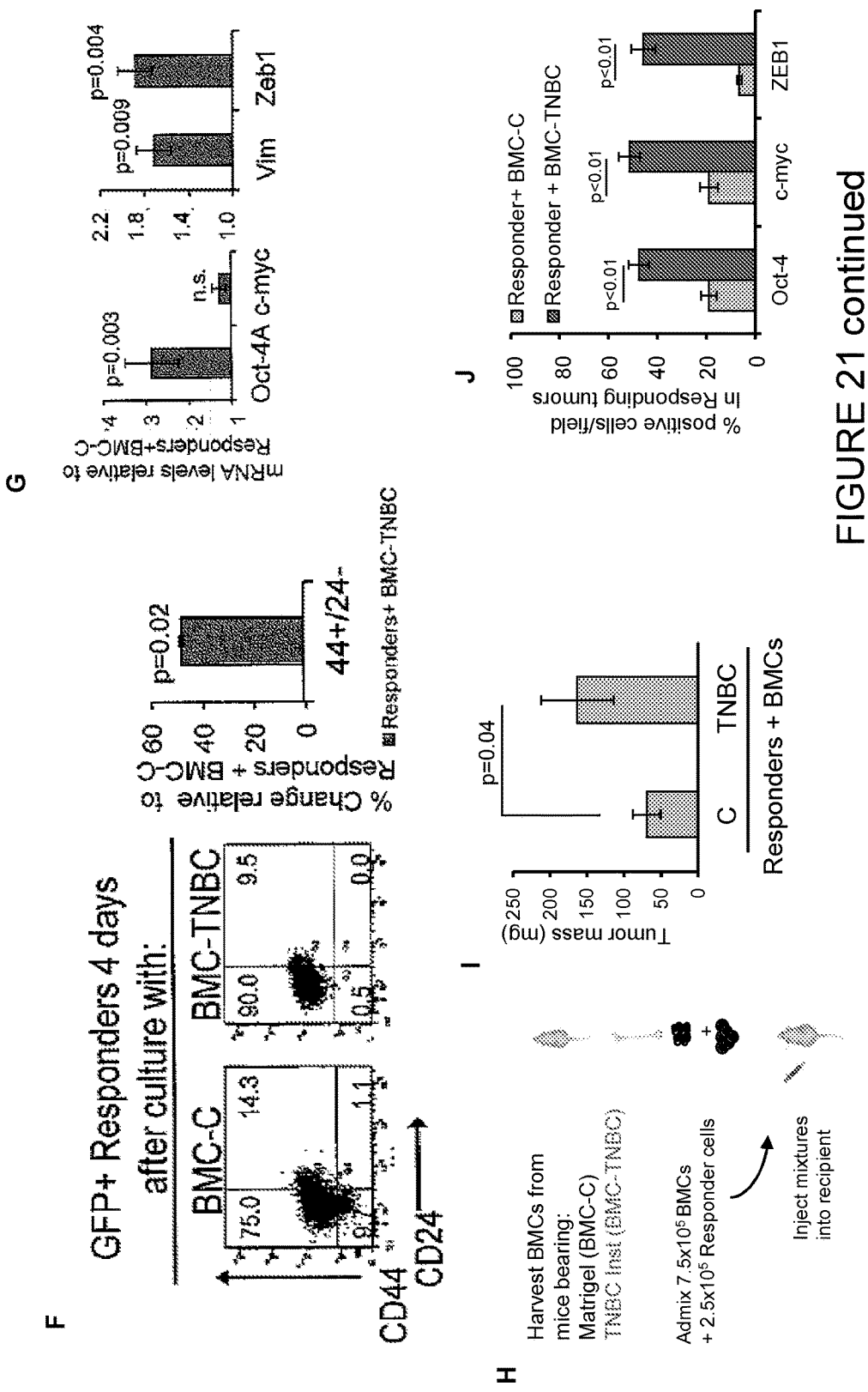

Thirteen of the most differentially expressed genes by RT-QPCR in the GFP-negative stromal cell populations sorted from responding tumors that had formed under the TNBC or control systemic environments were then analyzed (FIG. 21A). TNBC-mediated systemic instigation resulted in formation of a responding tumor microenvironment in which CXCL1, EGF, IGF-1, Wnt3, and TGFI31 were significantly up-regulated relative to the control microenvironment (FIG. 21B). Expression levels of CCL8, CSF1R, FRZB, ACTB ((3-actin), IL6, SPP1, and TXLNA (IL14) were not significantly different and IGF-2 expression was significantly down-regulated in TNBC-induced microenvironment relative to controls (FIG. 21B).

Two growth factors that were highly up-regulated in the TNBC-induced microenvironment, EGF and IGF-1 (FIG. 21B, C) were of interest. EGF ligands are found in 50-90% of primary carcinomas from patients with poor prognosis and the majority of TNBC express the EGF receptor (Dent et al., 2007; Pal et al., 2011; Saeki et al., 1995). In certain contexts, EGF induces c-myc expression to reduce breast tumor latency (Sinn et al., 1987), and has recently been shown to enhance Zeb1 expression in breast tumor cells (Vergara et al., 2011). High levels of phosphorylated IGF1R/insulin receptor and its ligands are present in malignant human breast tissues and are associated with poor patient prognosis (Chitnis et al., 2008; Pollak, 2008; Resnik et al., 1998). IGF-1, which signals through the insulinfIGF-1 receptor, has recently been shown to induce pluripotency factors, including Oct4, during cellular reprogramming (Li and Geng, 2010).

It was confirmed that responding HMLER-HR tumor cells indeed expressed both the EGF and IGF receptors (EGFR and IGF1R/InsR) in vitro (FIG. 26B), and did not express EGF or IGF-1 ligands (FIG. 26C), indicating that these cells would depend on paracrine sources of these ligands to activate the cognate receptors. In responding BT-549 cells, which also express both receptors (data not shown), expression of the EGF Nand was similar to that of the responding HMLER-HR cells; however, IGF-1 levels were 3000-fold higher in BT-549 relative to HMLER-HR (data not shown). Therefore, BT-549 cells might activate IGFR in an autocrine manner but would rely on exogenous sources of EGF to activate the EGF receptor.

Upon activation, EGFR is phosphorylated at residue Tyr1068 and IGF1R/InsR is phosphorylated at residues Tyr1161fTyr1185 (Hynes and Lane, 2005; Litzenburger et al., 2011). Using phospho-specific antibodies to these residues, we found that at both early (8 days) and late (60 days) time points in responding tumor growth in the TNBC instigating environment, HMLER-HR responders, as well as some stromal cells, expressed the active forms of EGFR and IGF1R/IR (data not shown). Receptor activation was not observed to any significant extent in the indolent HMLER-HR responding tumor cells exposed to the MATRIGEL control environment (data not shown). Strikingly, in addition to maintaining their malignancy profile, the early stage HMLER-HR responding tumors that had been transplanted into secondary recipient hosts (FIG. 20) also displayed EGF and IGF receptor activation (data not shown). Although the majority of the BT-549 responder cells displayed activated 1GF1R in the control MATRIGEL environment, ostensibly in an autocrine fashion, it was not sufficient to drive their aggressive growth; only when EGFR was concomitantly activated in the TNBC environment did these cells form aggressively growing tumors (FIG. 25B-D).

Pro-Tumorigenic Bone Marrow Cells are a Source of Bloavailable EGF and IGF-1 and Modulate the Responder Malignancy Profile The precisely the stromal source of bioavailable EGF and IGF-1 ligands were determinei. Bone marrow cells (BMCs) and bone marrow derived cells play an important role in breast tumor progression and resistence to chemotherapy (Denardo et al., 2011). It is known from previous work that in the presence of instigating TNBC tumors, BMCs are rendered pro-tumorigenic even prior to their mobilization from the marrow and recruitment to sites where responding tumors reside (Elkabets et al., 2011; McAllister et al., 2008). Therefore, bone marrow derived cells could play a direct role in programming responding tumor cell malignancy.

BMCs were isolated from mice bearing TNBC instigating tumors (BMC-TNBC) or MATRIGEL plugs (BMC-C) and found that EGF and IGF-1 expression levels were both ~2-fold higher in BMC-TNBC than in BMC-C (FIG. 21D, 26D). We then tested the function of the various BMC preparations by culturing them with 1-IMLER-HR responding tumor cells in medium devoid of EGF and insulin/IGF-1 (FIG. 21E).

Responding cells that had been co-cultured with BMC-TNBC underwent 50% enrichment in the CD44+/CD24− population above those cultured with BMC-C and was coupled with a concomitant reduction in the differentiated populations (FIG. 21F). The BMC-TNBCs also induced significant upregulation Oct4A, Zeb1 and vimentin relative to responding tumor cells co-cultured with BMC-C (FIG. 21G). Expression of c-myc was not statistically different between cohorts (FIG. 21G); however, we determined that c-myc upregulation is EGF dose-dependent (FIG. 26E). These data therefore suggested that BMC-TNBC might be responsible for the vast majority of responding tumor cell malignant programming.

To test whether BMCs had a role in modulating responding tumor cell malignancy in vivo, BMC-TNBC and BMC-C were isolated and mixed with responder cells prior to injection into host mice, according to our established protocol (McAllister et al., 2008) (FIG. 21H). In addition, and in order to determine whether any effects we might observe were specific to TNBC, we mixed responder cells with BMCs from mice bearing LBC tumors (BMC-LBC). Responding tumors were then analyzed 58 days after injection of admixtures.

Admixing BMC-TNBC resulted in desmoplastic responding tumors in 100% of the mice; these tumors were ~2.4-fold larger than those that had been admixed with BMCs from cancer-free hosts (100% incidence) (FIG. 21I). BMCs from mice bearing LBC tumors (BMC-LBC) also promoted tumor growth in 100% of the mice; however, they did not significantly enhance the final mass of responding tumors above that of the cancer-free control BMCs, and these tumors were not desmoplastic (FIG. 21I).

The malignancy profile factors were significantly enriched in the responder tumors that had been admixed with BMC-TNBC relative to those from cancer-free controls (FIG. 21J). BMC-LBC did not affect the malignancy profile of the responding tumor cells and were no different from BMC-C (FIG. 21J). Likewise, the majority (~80%) of tumor cells in the BMC-TNBC cohort maintained the CD44+/CD24− phenotype and failed to differentiate, as they had in the BMC-C or BMC-LBC cohorts (FIG. 21J).

Collectively, these results indicated that BMCs from hosts bearing TNBC phenocopied the effects of the TNBC systemic environment. These pro-tumorigenic BMCs were equipped with the ability to promote responding tumor malignancy, either directly or in cooperation with other stromal components, ostensibly by providing a source of both EGF and IGF-1.

Figure 22:
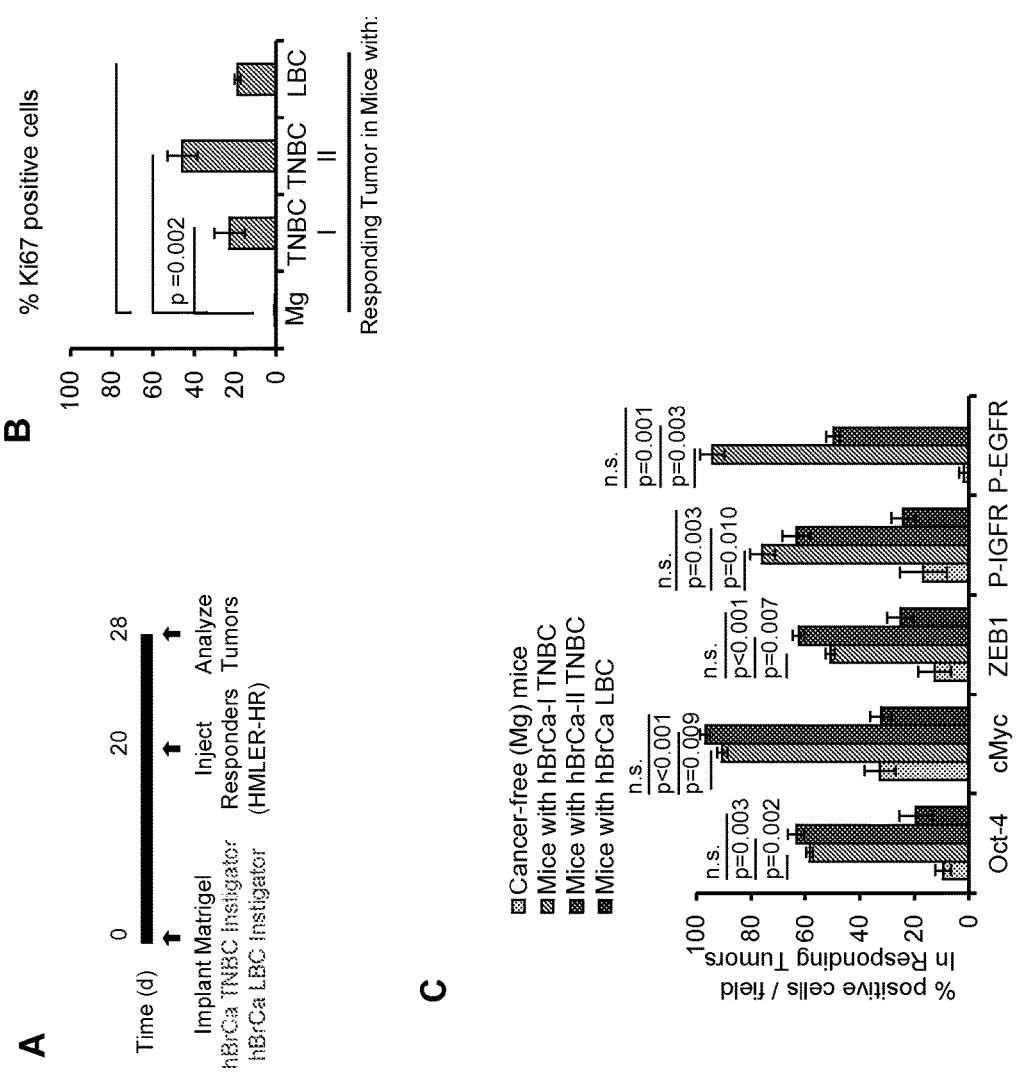
FIGS. 22A-22C. Human Tumor Specimens Establish Tumor-Supportive Systemic Environments that Influence Disease Malignancy.
Figure 27:
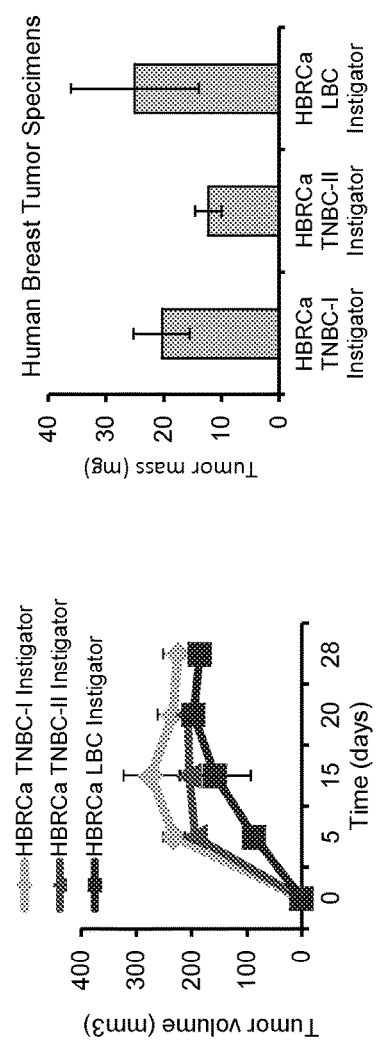
FIG. 27. Identification of Instigating Human Breast Tumor Surgical Specimens and hallmarks of systemic instigation. Left, growth kinetics of TNBC or LBC instigating human tumor specimens (HBRCa TNBC-I, HBRCa TNBC-II, HBRCa LBC) growing opposite responding tumor cells for 28 days (n=3 mice per tumor specimen). Right, final mass of TNBC or LBC HBRCa instigator tumors 28 days after injection; values were not statistically significantly different.

Breast Cancer Patient Tumors Drive Malignancy Profiles in a Subtype-Specific Systemic Fashion In an effort to understand whether human primary tumors establish similar pro-tumorigenic environments, we analyzed the effect of three different tumor specimens from breast cancer patients on otherwise dormant breast cancer cells. Two samples were obtained from women with TNBC (ER−/PR−/Her2−) and one sample from a woman with LBC (ER-E/PR+/Her2+). The samples were designated as: hBrCa TNBC-I, hBrCa TNBC-II, and hBrCa-LBC. Each tumor specimen was minced and divided into equal portions that were surgically implanted beneath the skin of 3 different Nude mice. After a 20-day period of equivalent instigating tumor growth (FIG. 27A), responder cells (HMLER-HR) were injected into the contralateral flank of these mice (FIG. 22A). Eight days after injection, when responder cell plugs in each cohort were of comparable size (data not shown), all responding tumors were recovered for analysis.

Responding tumor cells recovered from the systemic environments created by hBrCa TNBC-I, hBrCa-TNBC-II and hBrCa-LBC were significantly more proliferative than those from the MATRIGEL environment, as determined by staining for the proliferation marker, Ki67 (FIG. 22B) Immunohistochemical analysis revealed that responding tumor cells growing in the systemic environments created by both hBrCa TNBC-I and hBrCa TNBC-II were significantly enriched for malignancy profile factors, as well as activated EGFR and IGFR, relative to MATRIGEL environment controls (FIG. 22C). In contrast, responder cells from tumors that had been subjected to the hBraCa LBC-induced environment lost expression of CD44 and were ~5.5-fold enriched for CD24 relative to MATRIGEL controls (FIG. 22C). In these LBC-instigated responding tumors, expression of malignancy profile factors was no different from that of controls (FIG. 22C).

These results suggested that primary human tumors might be stratified based on their ability to create pro-tumorigenic systemic environments. We previously established that instigating TNBC tumors secrete OPN, which is necessary for TNBC-dependent systemic instigation, while instigating LBC tumors rely on OPN-independent mechanisms to promote responding tumor growth (McAllister et al., 2008, and unpublished data) (data not shown). Indeed, elevated plasma levels of OPN correlate with metastatic disease and poor prognosis for patients with various types of cancer (Bramwell et al., 2006), including triple negative and basal-like breast cancers (Wang et al., 2010). A tissue microarray (TMA) that included 8 primary breast tumors and their matched lymph node (LN) metastases were analyzed to test whether OPN expression in primary breast tumors would predict the presence of the malignant profile in their matched LN metastasis.

Six of the eight primary tumors expressed OPN to varying extents while two tumors were devoid of OPN expression (data not shown). The matched LN metastases from the two primary tumors that were devoid of OPN expression did not express the malignancy factors Oct4 and Zeb1 (data not shown). Two of the primary tumors in which OPN staining was scored as weak had corresponding LN metastases that displayed only a partial malignancy profile (data not shown). The remaining four OPN-positive primary tumors had matched LN metastases that expressed both of the malignancy factors, Oct4 and Zeb1, and these were the only LN metastases that showed evidence of both EGFR and IGFR activation (data not shown).

Therefore, testing real human tumor specimens in the described in vivo model gave a clear indication that breast tumors were capable of establishing systemic environments that had a relevant impact upon disease malignancy. Although preliminary, the TMA analysis indicated that OPN expression might provide a means of stratifying human tumors for their ability to establish the type of pro-tumorigenic systemic environment that mitigates distant tumor growth by inducing the malignancy profile, as it is defined here.

EGF and IGF-1 Together Modulate Indolent and Malignant States In Vitro

The results here indicated that EGF and IGF-1 were expressed exclusively in the TNBC-induced microenvironment and that the cognate receptors were activated in responding tumor cells under TNBC instigating conditions. Whether EGFR and IGF1R signaling were necessary and/or sufficient for modulating responding tumor malignancy remained to be investigated. To do so, the effects of either depleting EGF and/or insulin from HMLER-HR responder cells that had been cultured in complete medium (C.M.) or adding EGF and/or insulin to cells that had been cultured in depleted medium (D.M., medium depleted of both EGF and insulin) were examined. For these studies, cells were treated under various conditions for 4 days, then assessed differentiation status by flow cytometry, expression of malignancy factors (e.g. Oct-4, Zeb1, c-myc) by qPCR, and tumor-forming capacity by soft agar colony formation.

Figure 23:
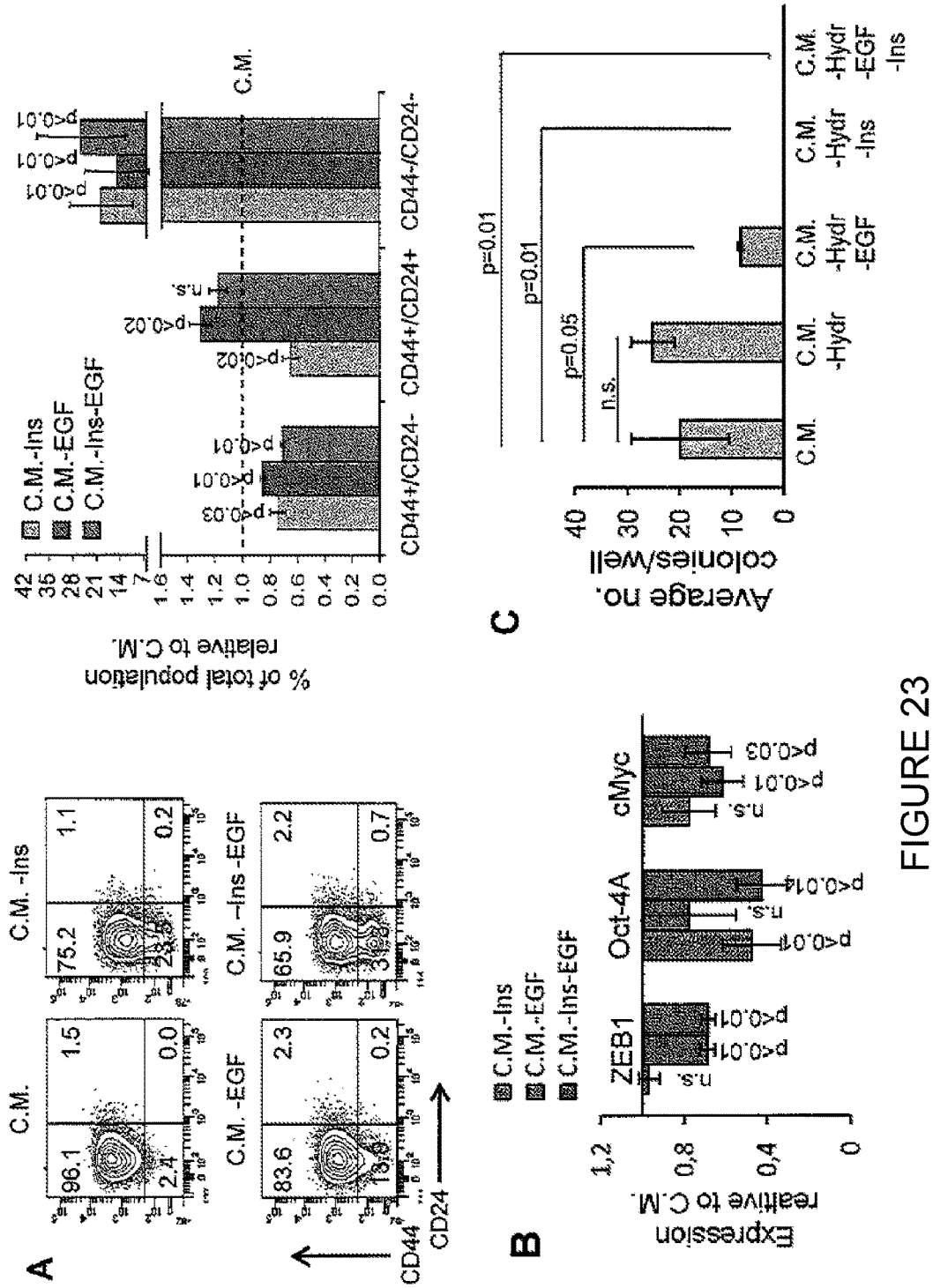
FIGS. 23A-23J. EGF and IGF-1 Modulate Indolent and Malignant States in vitro.
Figure 23:
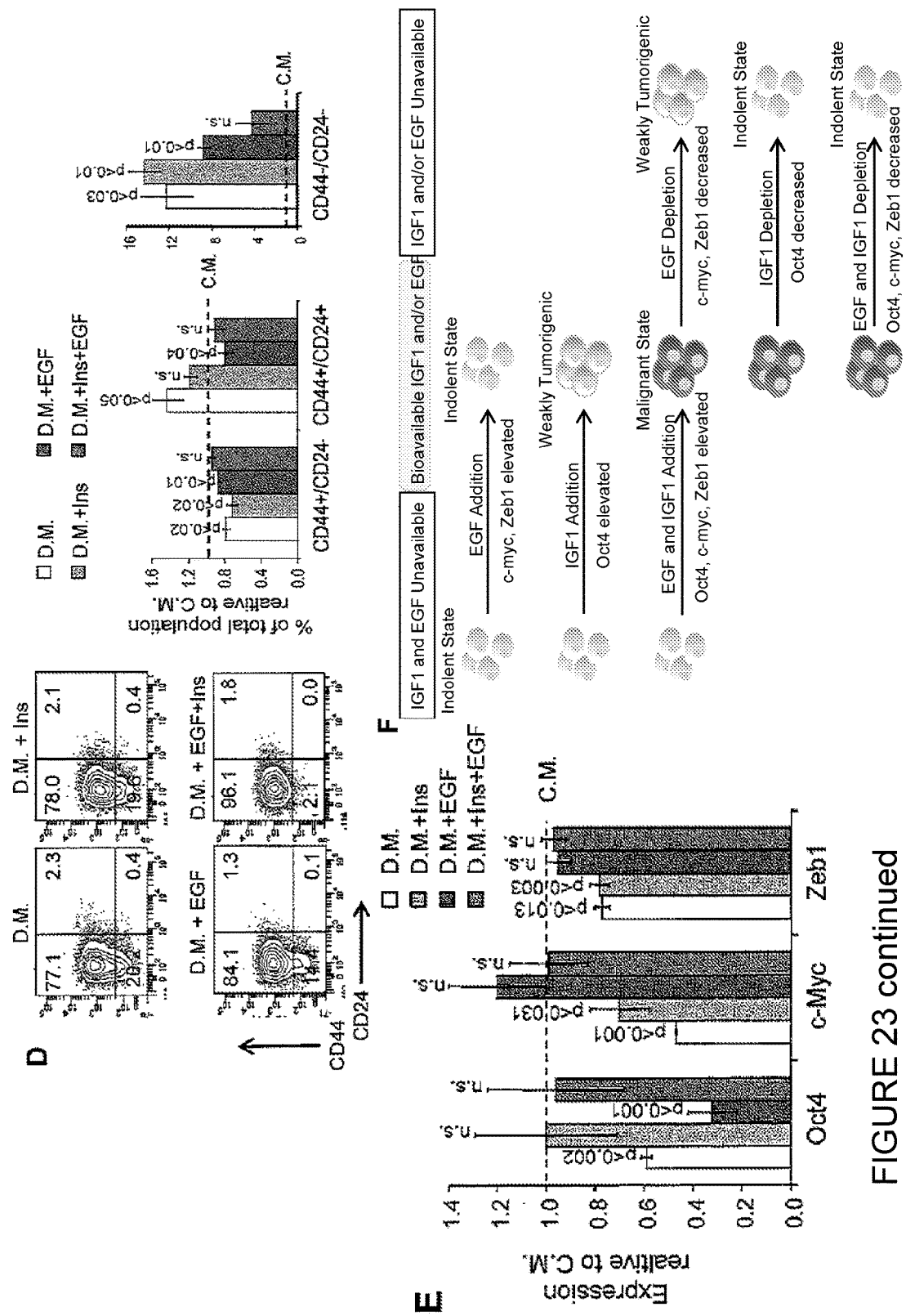
Figure 23:
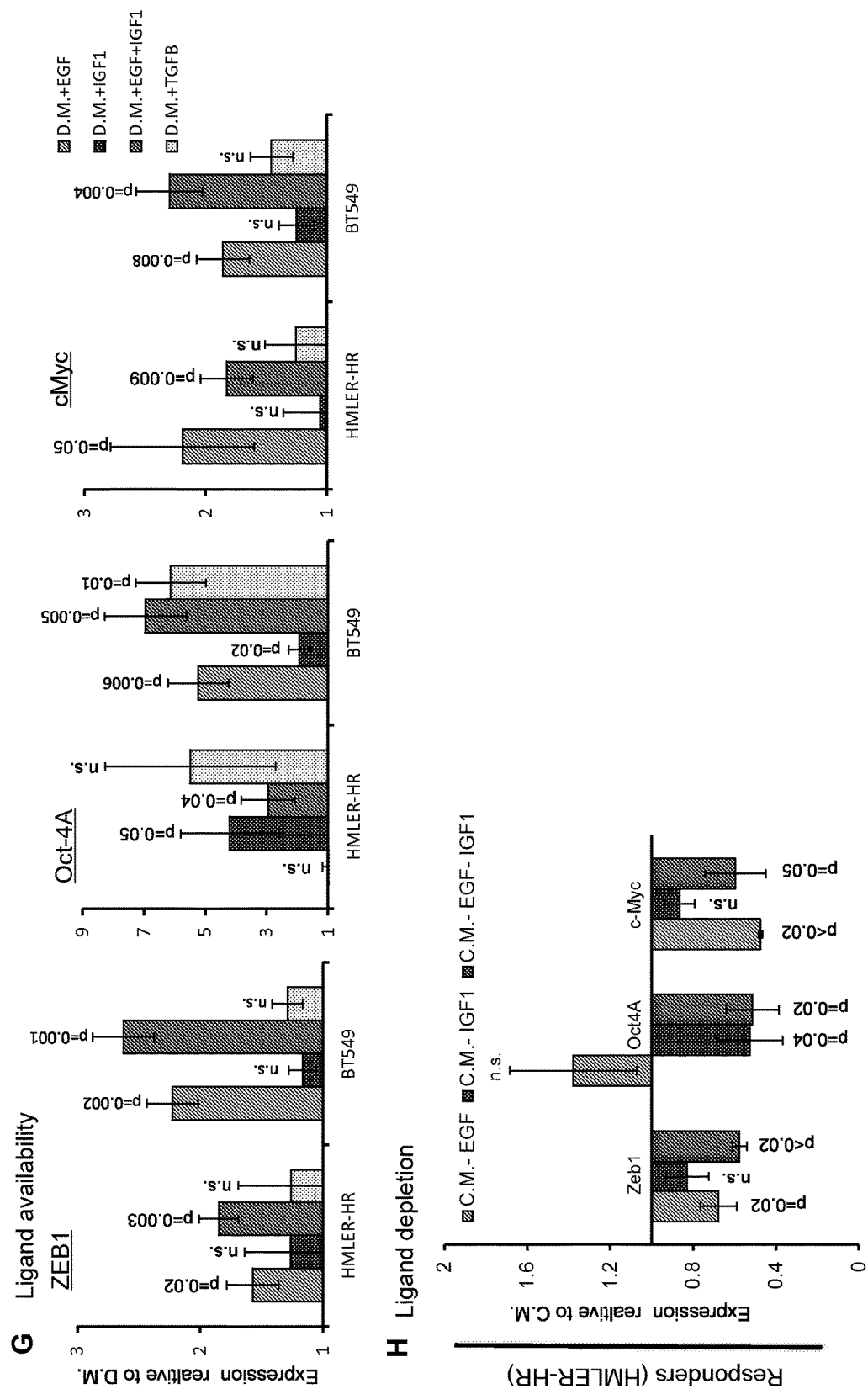
Figure 23:
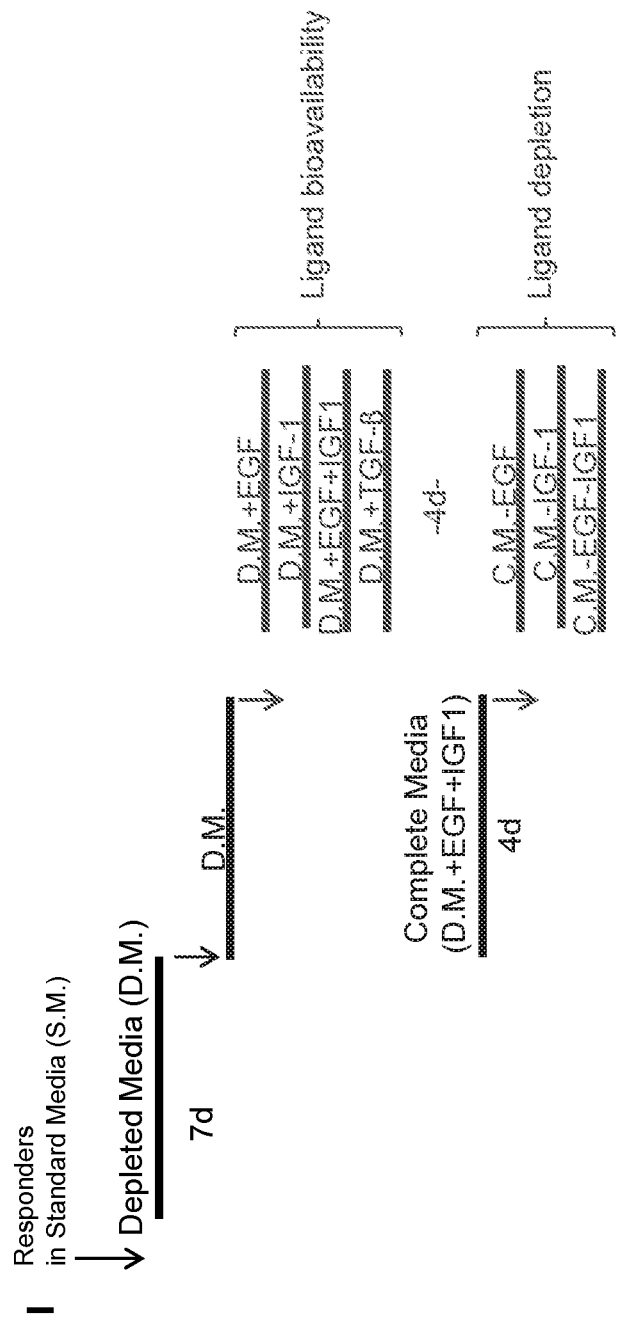
Figure 23:
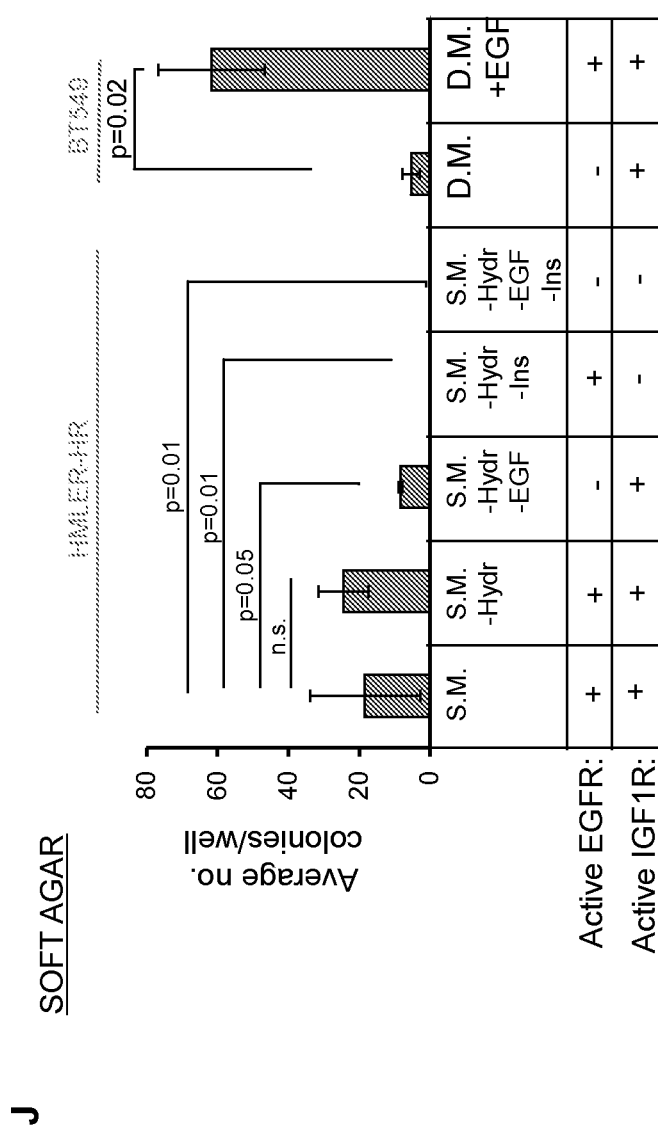
Figure 28:
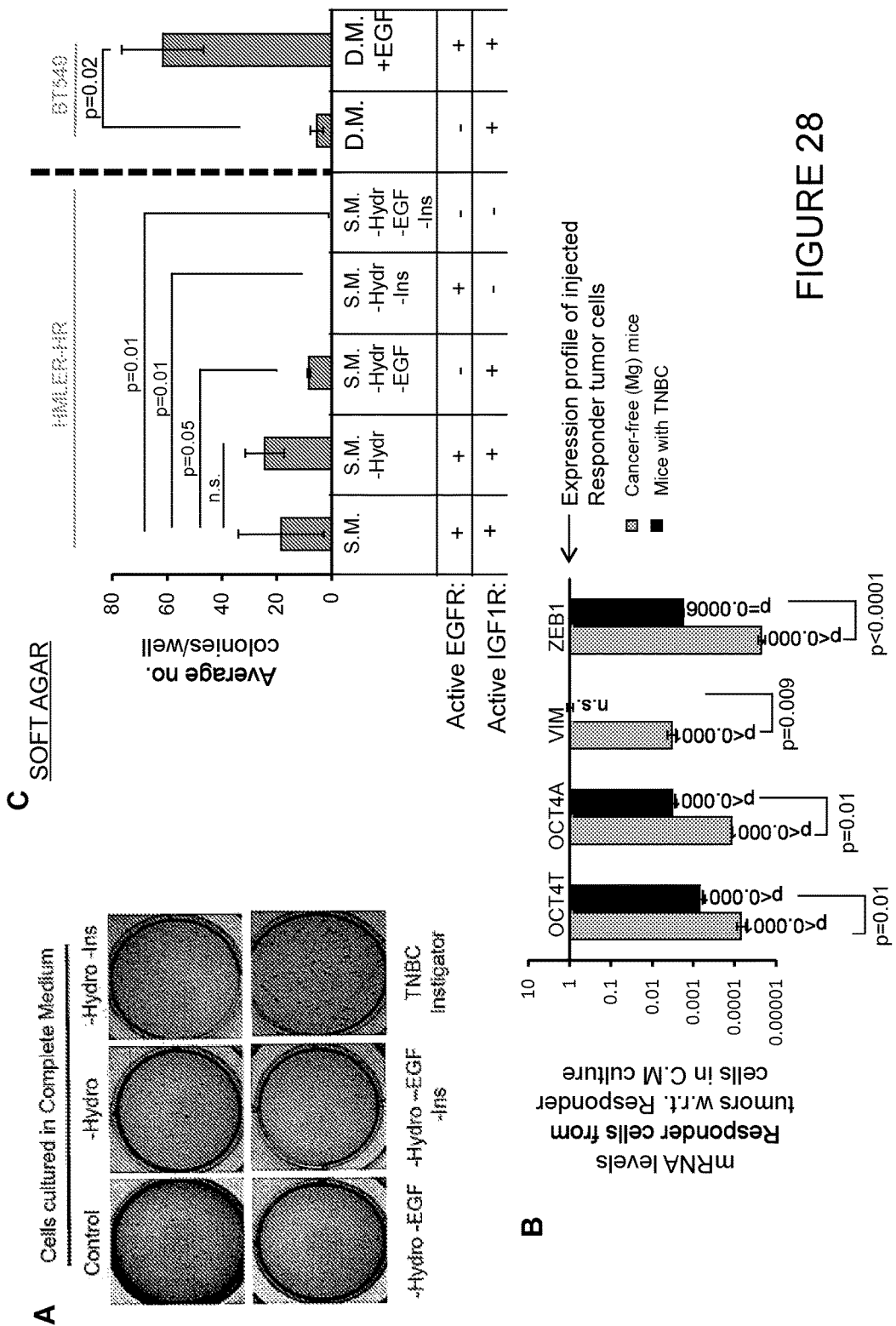
FIGS. 28A-28E. EGF and IGF-1 Together Modulate Indolent and Malignant States in vitro.
Figure 28:
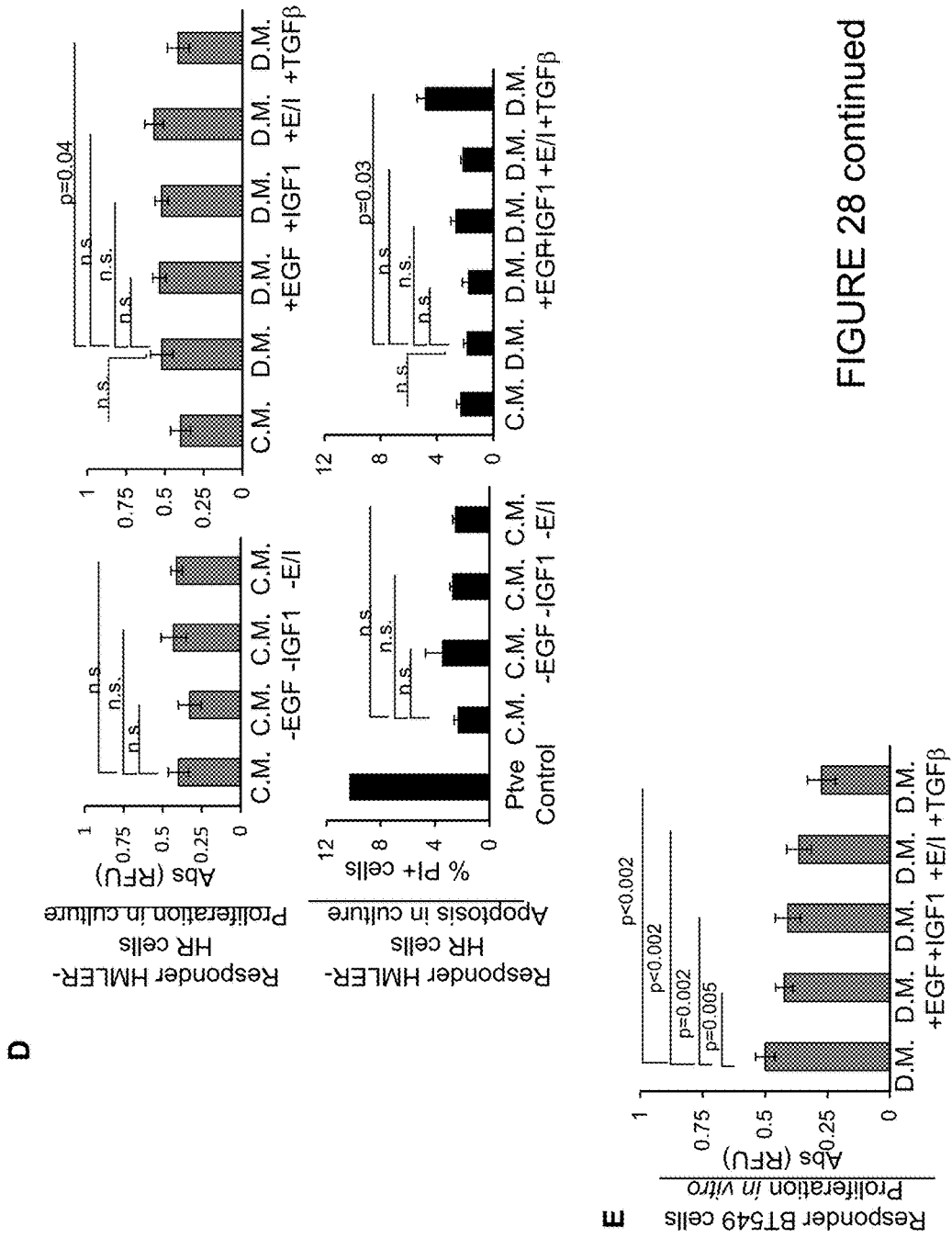

Depleting EGF from the C.M. resulted in a moderate ~13% loss of CD44+ cells and a ~37% enrichment of CD24+ cells (FIG. 23A). Expression of c-myc and Zeb1 were significantly reduced, yet expression of Oct4 was unchanged relative to control C.M. (FIG. 23B). Nevertheless, these cells maintained modest in vitro tumorigenic capacity (FIG. 23C, 28A). Depletion of insulin from C.M. resulted in a ~22% loss of the CD44+/CD24− population (~10-fold enrichment of cells with the CD44−/CD24− phenotype) (FIG. 23A). These cells showed a significant loss of Oct4 but not of c-myc or Zeb1 expression (FIG. 23B) and completely lost colony-forming capacity (FIG. 23C, 28A). Depriving the population of both EGF and insulin resulted in an overall ~31% reduction in CD44+/CD24− cells (~13-fold enrichment of CD44−/CD24− cells; ~21% enrichment of CD24+ cells) (FIG. 23A). This population also displayed significant reductions in Oct4, c-Myc, and Zeb1 expression, and a complete loss of tumor-forming capacity (FIG. 23A-23C, 28A).

Adding insulin to cells that had been kept in D.M. for 4 days restored Oct4 expression to levels that were comparable to the C.M. controls; however c-Myc and Zeb1 levels remained significantly lower than the controls. Insulin was also not sufficient to restore CD44 expression (FIG. 23D, 23E). Unlike insulin, adding EGF to cells cultured in D.M. was sufficient to restore CD44 expression (FIG. 23D), although not to the full extent as cells maintained in C.M. (FIG. 23A, 23D). EGF treatment also restored Zeb1 and c-Myc expression to levels that were comparable to C.M. (FIG. 23E), while Oct4 expression was unaffected by addition of EGF. Addition of both EGF and insulin to the D.M. completely restored CD44/CD24 expression patterns and Oct4A, c-Myc and Zeb1 expression were restored to the same extent as the population maintained in C.M. (FIG. 23D, 23E).

Figure 25:
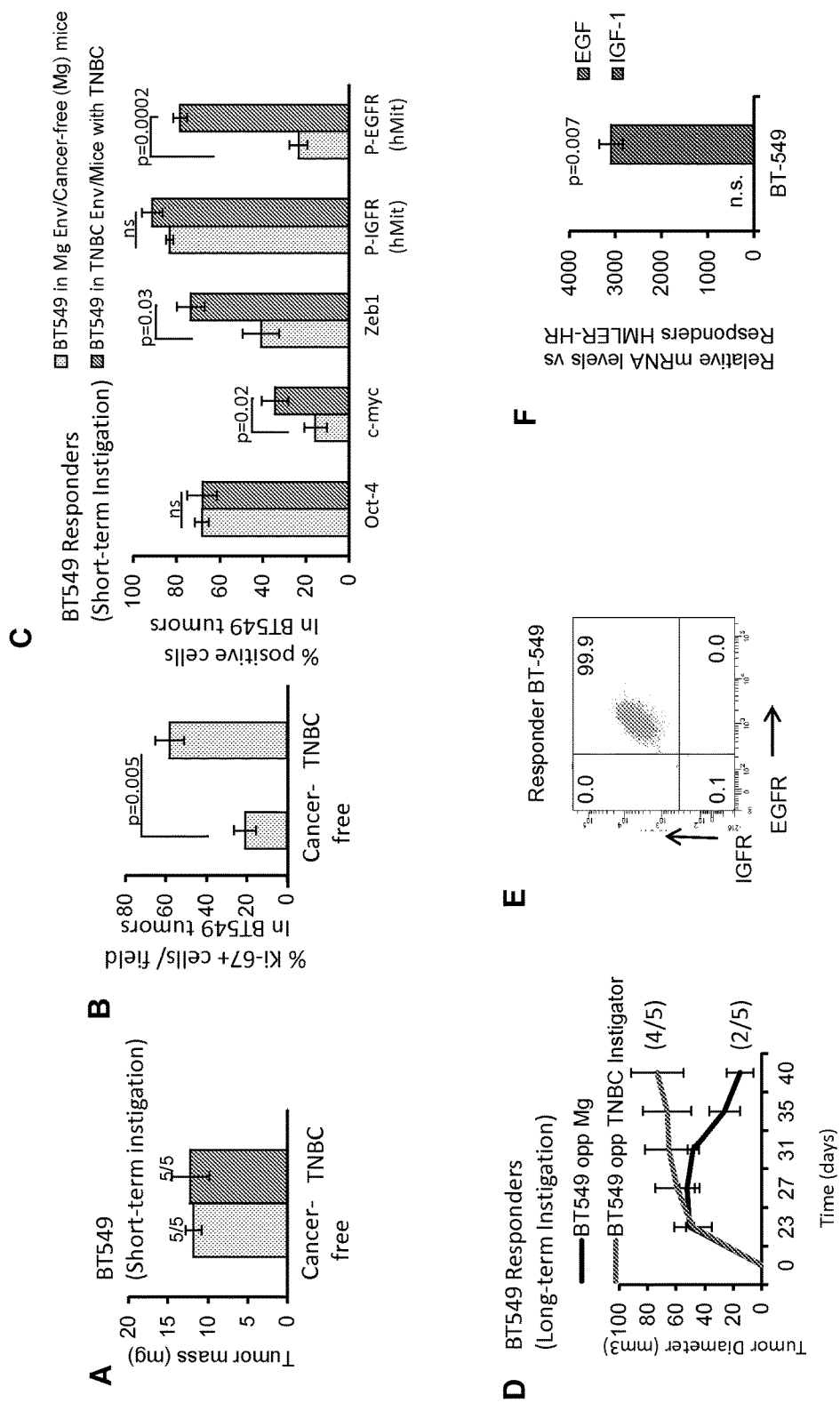
FIGS. 25A-25F. Response to the Pro-Tumorigenic TNBC Environment is Not Oncotype Specific.

Hence, the data supported a model in which EGFR and IR/IGFIR signaling pathways together modulate interconversion of responsive tumor cell populations between indolent and malignant states (FIG. 23F). Under conditions of both EGFR and IR/IGF1R ligand bioavailability, EGF depletion alone was not sufficient to convert cells to the indolent state—depletion of insulin/IGF-1 was also required. Under conditions when ligands were not bioavailable, EGFR and IGF1R activation together were necessary to convert a responsive population of cells from a state of indolence to one of malignancy. These conclusions were supported by the present in vivo observations; upon injection, HMLER-HR responder cells (i.e., from culture in C.M.) existed in the malignant state, which was lost in the MATRIGEL environment, whereas this loss was significantly attenuated in the TNBC systemic environment in which bioavailable sources of EGF and IGF-1 were provided (FIG. 28B). Similarly, autocrine expression of IGF-1 was not sufficient to convert BT549 cells to the malignant state in the MATRIGEL environment, in which EGF was not bioavailable; however, when both ligands were bioavailable in the TNBC environment, these cells achieved malignancy (FIG. 25).

EGFR and IGFR Inhibition Restricts Responder Cells to an Indolent State In Vivo

Clinical studies support the importance of EGFR as a target for therapy, as it is expressed in a large subset of triple negative primary breast carcinomas and EGFR ligands are found in 50-90% of primary carcinomas from patients' with poor prognosis (Pal et al., 2011; Saeki et al., 1995). Several anti-EGFR molecules have been shown to inhibit neoplastic growth in experimental models (Blackledge and Averbuch, 2004). However, in phase II clinical trials of breast cancer patients with advanced disease, fewer than 10% of patients responded to EGFR-target therapy and resistance to treatment appeared to be a primary contributor to patient demise (Morgillo et al., 2007a). It has been suggested that signaling through other tyrosine kinase receptors, such as IGF1R, may confer resistance to EGFR inhibition (Jones et al., 2004; Morgillo et al., 2007b). High levels of phosphorylated IGF1R/insulin receptor and its ligand are present in malignant human breast tissues and are associated with poor patient prognosis due to its putative role in various aspects of tumor development and metastasis (Chitnis et al., 2008; Pollak, 2008; Resnik et al., 1998). Prompted by these clinical findings and our own results, we tested whether EGFR and IGFR dual inhibition would prevent outgrowth of responding tumors in the context of TNBC instigation.

Figure 24:
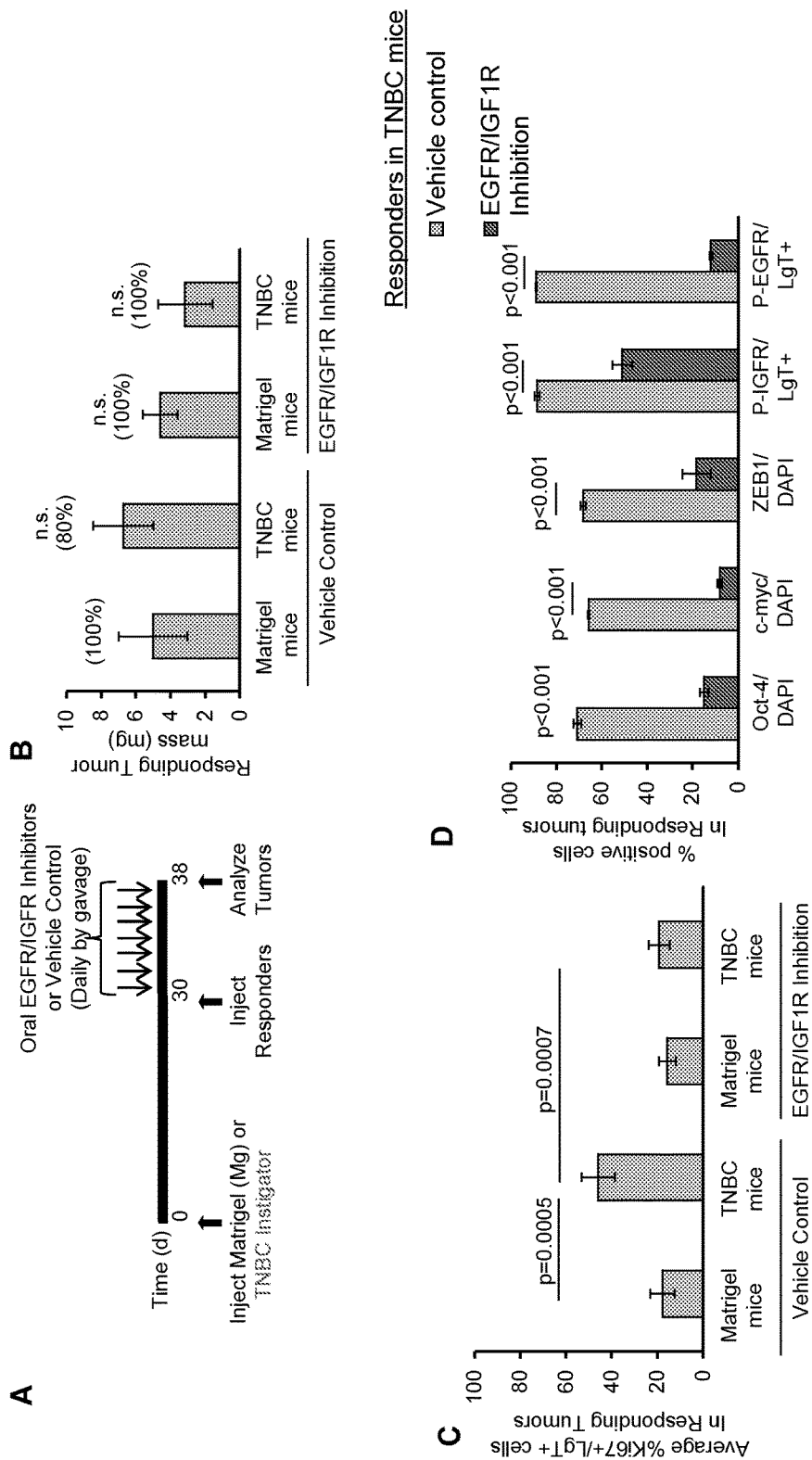
FIGS. 24A-24D. EGFR/IGFR Dual Inhibition Maintains Responding Tumors in an Indolent State.
Figure 29:
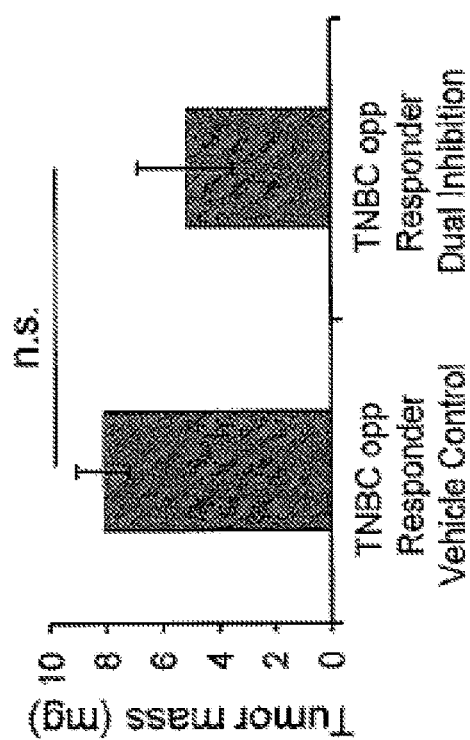
FIG. 29. EGFR/IGFR inhibitors do not affect the phenotype of responding tumor cells in the control Matrigel environment. Final mass of TNBC instigators after 5 weeks of growth (mice were treated during the last 8 days with vehicle DMSO or both the EGFR inhibitor-erlotinib; dose 100 mg/kg/day- and IGFR inhibitor-BMS-754807; dose 50 mg/kg/day-every day by oral gavage) (n=5 mice per group). Differences were not statistically significant (n.s.).

MATRIGEL or instigating TNBC tumor cells were injected into nude mice and allowed to grow for 30 days before injecting responding tumor cells into the contralateral flank, according to our protocol (FIG. 24A). After injection of responders, mice were enrolled into cohorts that were treated with either a combination of the EGFR inhibitor, erlotinib (100 mg/kg/day) and the IGFR inhibitor, BMS-754807 (50 mg/kg/day) or DMSO vehicle control once per day for eight days. We harvested tumors after 8 days, a time point at which the conversion of the malignant profile occurred and at which it was still possible to recover tumors from control mice. We confirmed that activation of EGFR and IGFIR/IR were both significantly attenuated in the drug-treated cohorts, but not in control cohorts (FIG. 24D). The drug treated mice also developed a skin rash, which has been reported for patients treated with erlotinib (Numico et al., 2011). Importantly, instigating TNBC tumor mass was not affected by dual inhibitor treatment during this dosing regimen (FIG. 29).

As expected, responding tumor cells in the vehicle-treated TNBC environment were significantly more proliferative than those exposed to the vehicle-treated control MATRIGEL environment (~46% vs. ~18%, respectively), as determined by staining for the proliferation marker, Ki67 (FIG. 24C). Dual EGFR/IGFR inhibition resulted in a ~60% decrease in Ki67+ responder cells that had been exposed to the TNBC environment. Proliferation of responding tumor cells in the MATRIGEL environment (~18%) were unaffected by drug treatment (~19%) (FIG. 24C).

Responding tumors from the vehicle treated mice formed with a desmoplastic stroma under instigating conditions (data not shown), and maintained expression of the malignancy profile (FIG. 24D). Responding tumor plugs exposed to the TNBC environment in mice that had been treated with EGFR/IGFR inhibitors also showed evidence of a myofibroblast-rich, reactive stroma (data not shown). The percentage of responding cells expressing CD44+/CD24− was not affected by dual inhibition; however, expression of Oct-4, c-myc, and Zeb1, were drastically reduced in these responding tumor cells (~79%, ~87%, and ~73% reductions, respectively) relative to the vehicle controls (FIG. 24D).

Taken together, these results indicated that inhibition of both EGF and IGF receptor activation restricted responding tumor cells to a non-proliferative, indolent state without affecting recruitment of reactive stroma. Hence, the mechanism of action of EGFR/IGFR dual inhibition ostensibly occurred within the responding tumor microenvironment to inhibit paracrine interactions between responding tumor cells and their systemically-mandated microenvironment.

References

Al-Hajj, M., Wicha, M. S., Benito-Hernandez, A., Morrison, S. J., and Clarke, M. F. (2003). Prospective identification of tumorigenic breast cancer cells. Proc Nati Acad Sci USA 100, 3983-3988.

Ben-Porath, I., Thomson, K W., Carey, V. J., Ge, R., Bell, G. W., Regev, A., and Weinberg, R. A. (2008). An embryonic stem cell-like gene expression signature in poorly differentiated aggressive human tumors. Nat Genet 40, 499-507.

Blackledge, G., and Averbuch, S. (2004). Gefitinib ('Iressa', ZD1839) and new epidermal growth factor receptor inhibitors. Br J Cancer 90, 566-572.

Botquin, V., Hess, H., Fuhrmann, G., Anastassiadis, C., Gross, M. K., Vriend, G., and Scholer, H. R. (1998). New POU dimer configuration mediates antagonistic control of an osteopontin preimplantation enhancer by Oct-4 and Sox-2. Genes Dev 12, 2073-2090.

Bramwell, V. H., Doig, G. S., Tuck, A. B., Wilson, S. M., Tonkin, K. S., Tomiak, A., Perera, F., Vandenberg, T. A., and Chambers, A. F. (2006). Serial plasma osteopontin levels have prognostic value in metastatic breast cancer. Clin Cancer Res 12, 3337-3343.

Carboni, J. M., Wittman, M., Yang, Z., Lee, F., Greer, A., Hurlburt, W., Hillerman, S., Cao, C., Cantor, G. H., Dell-John, J., et al. (2009). BMS-754807, a small molecule inhibitor of insulin-like growth factor-1R/IR. Mol Cancer Ther 8, 3341-3349.

Castano, Z., Tracy, K., and McAllister, S. S. (2011). The tumor macroenvironment and systemic regulation of breast cancer progression. Int J Dev Biol 55, 889-897.

Chitnis, M. M., Yuen, J. S., Protheroe, A. S., Pollak, M., and Macaulay, V. M. (2008). The type 1 insulin-like growth factor receptor pathway. Clin Cancer Res 14, 6364-6370.

Demicheli, R. (2001). Tumour dormancy: findings and hypotheses from clinical research on breast cancer. Semin Cancer Biol 11, 297-306.

Denardo, D. G., Brennan, D. J., Rexhepaj, E., Ruffell, B., Shiao, S. L., Madden, S. F., Gallagher, W. M., Wadhwani, N., Keil, S. D., Junaid, S. A., et al. (2011). Leukocyte Complexity Predicts Breast Cancer Survival and Functionally Regulates Response to Chemotherapy. Cancer Discov 1, 54-67.

Dent, R., Trudeau, M., Pritchard, K. 1., Hanna, W. M., Kahn, H. K., Sawka, C. A., Lickley, L. A., Rawlinson, E., Sun, P., and Narod, S. A. (2007). Triple-negative breast cancer: clinical features and patterns of recurrence. Clin Cancer Res 13, 4429-4434.

Elenbaas, B., Spirio, L., Koerner, F., Fleming, M. D., Zimonjic, D. B., Donaher, J. L., Popescu, N. C., Hahn, W. C., and Weinberg, R. A. (2001). Human breast cancer cells generated by oncogenic transformation of primary mammary epithelial cells. Genes Dev 15, 50-65.

Elkabets, M., Gifford, A. M., Scheel, C., Nilsson, B., Reinhardt, F., Bray, M. A., Carpenter, A. E., Jirstrom, K., Magnusson, K., Ebert, B. L., et al. (2011). Human tumors instigate granulin-expressing hematopoietic cells that promote malignancy by activating stromal fibroblasts in mice. J Clin Invest 121, 784-799.

Foulkes, W. D., Smith, I. E., and Reis-Filho, J. S. (2010). Triple-negative breast cancer. N Engl J Med 363, 1938-1948.

Guarneri, V., and Conte, P. (2009). Metastatic breast cancer: therapeutic options according to molecular subtypes and prior adjuvant therapy. Oncologist 14, 645-656.

Guo, Y., Costa, R., Ramsey, H., Starnes, T., Vance, G., Robertson, K., Kelley, M., Reinbold, R., Scholer, H., and Hromas, R. (2002). The embryonic stem cell transcription factors Oct-4 and FoxD3 interact to regulate endodermal-specific promoter expression. Proc Natl Acad Sci USA 99, 3663-3667.

Hahn, W. C., Counter, C. M., Lundberg, A. S., Beijersbergen, R. L., Brooks, M. W., and Weinberg, R. A. (1999). Creation of human tumour cells with defined genetic elements. Nature 400, 464-468.

Hynes, N. E., and Lane, H. A. (2005). ERBB receptors and cancer: the complexity of targeted inhibitors. Nat Rev Cancer 5, 341-354.

Ince, T. A., Richardson, A. L., Bell, G. W., Saitoh, M., Godar, S., Karnoub, A. E., Iglehart, I D., and Weinberg, R. A. (2007). Transformation of different human breast epithelial cell types leads to distinct tumor phenotypes. Cancer Cell 12, 160-170.

Jones, H. E., Goddard, L., Gee, J. M., Hiscox, S., Rubin', M., Barrow, D., Knowlden, J. M., Williams, S., Wakeling, A. E., and Nicholson, R. I. (2004). Insulin-like growth factor-I receptor signalling and acquired resistance to gefitinib (ZD1839; Iressa) in human breast and prostate cancer cells. Endocr Relat Cancer 11, 793-814.

Joyce, J. A., and Pollard, J. W. (2009). Microenvironmental regulation of metastasis. Nat Rev Cancer 9, 239-252.

Kenny, P. A., Lee, G. Y., Myers, C. A., Neve, R. M., Semeiks, J. R., Spellman, P. T., Lorenz, K., Lee, E. H., Barcellos-Hoff, M. H., Petersen, 0. W., et al. (2007). The morphologies of breast cancer cell lines in three-dimensional assays correlate with their profiles of gene expression. Mol Oncol 1, 84-96.

Kim, M. Y., Oskarsson, T., Acharyya, S., Nguyen, D. X., Zhang, X. H., Norton, L., and Massague, J. (2009). Tumor self-seeding by circulating cancer cells. Cell 139, 1315-1326.

Klein, C. A. (2009). Parallel progression of primary tumours and metastases. Nat Rev Cancer 9, 302-312.

Lee, M. J., Ye, A. S., Gardino, A. K., Heijink, A. M., Sorger, P. K., Macbeath, G., and Yaffe, M. B. (2012). Sequential application of anticancer drugs enhances cell death by rewiring apoptotic signaling networks. Cell 149, 780-794.

Li, Y., and Geng, Y. J. (2010). A potential role for insulin-like growth factor signaling in induction of pluripotent stem cell formation. Growth Norm IGF Res 20, 391-398.

Liao, D. J., and Dickson, R. B. (2000). c-Myc in breast cancer. Endocr Relat Cancer 7, 143-164.

Litzenburger, B. C., Creighton, C. J., Tsimelzon, A., Chan, B. T., Hilsenbeck, S. G., Wang, T., Carboni, J. M., Gottardis, M. M., Huang, F., Chang, J. C., et al. (2011). High IGF-IR activity in triple-negative breast cancer cell lines and tumorgrafts correlates with sensitivity to anti-IGF-IR therapy. Clin Cancer Res 17, 2314-2327.

Mani, S. A., Guo, W., Liao, M. J., Eaton, E. N., Ayyanan, A., Zhou, A N., Brooks, M., Reinhard, F., Zhang, C. C., Shipitsin, M., et al. (2008). The epithelial-mesenchymal transition generates cells with properties of stem cells. Cell 133, 704-715.

McAllister, S. S., Gifford, A. M., Greiner, Al., Kelleher, S. P., Saelzler, M. P., Ince, T. A., Reinhardt, F., Harris, L. N., Hylander, B. L., Repasky, E. A, et al. (2008). Systemic endocrine instigation of indolent tumor growth requires osteopontin. Cell 133, 994-1005. McAllister, S. S., and Weinberg, R. A. (2010). Tumor-host interactions: a far-reaching relationship. J Clin Oncol 28, 4022-4028.

Meyers, M. O., Klauber-Demore, N., 011ila, D. W., Amos, K. D., Moore, D. T., Drobish, A. A., Burrows, E. M., Dees, E. C., and Carey, L. A. (2011). Impact of breast cancer molecular subtypes on locoregional recurrence in patients treated with neoadjuvant chemotherapy for locally advanced breast cancer. Ann Surg Oncol 18, 2851-2857.

Moreno-Bueno, G., Portillo, F., and Cano, A. (2008). Transcriptional regulation of cell polarity in EMT and cancer. Oncogene 27, 6958-6969.

Morgillo, F., Bareschino, M. A., Bianco, R., Tortora, G., and Ciardiello, F. (2007a). Primary and acquired resistance to anti-EGFR targeted drugs in cancer therapy. Differentiation 75, 788-799.

Morgillo, F., Kim, W. Y., Kim, E S., Ciardiello, F., Hong, W. K., and Lee, H. Y. (2007b). Implication of the insulin-like growth factor-IR pathway in the resistance of non-small cell lung cancer cells to treatment with gefitinib. Clin Cancer Res 13, 2795-2803.

Nichols, J., Zevnik, B., Anastassiadis, K., Niwa, H., Klewe-Nebenius, D., Chambers, I., Scholer, H., and Smith, A. (1998). Formation of pluripotent stem cells in the mammalian embryo depends on the POU transcription factor Oct4. Cell 95, 379-391.

Numico, G., Silvestris, N., and Grazioso Russi, E. (2011). Advances in EGFR-directed therapy in head and neck cancer. Front Biosci (Schol Ed) 3, 454-466.

Orimo, A., Gupta, P. B., Sgroi, D. C., Arenzana-Seisdedos, F., Delaunay, T., Naeem, R., Carey, V. J., Richardson, A. L., and Weinberg, R. A. (2005). Stromal fibroblasts present in invasive human breast carcinomas promote tumor growth and angiogenesis through elevated SDF-1/CXCL12 secretion. Cell 121, 335-348.

Pal, S. K., Childs, B. H., and Pegram, M. (2011). Triple negative breast cancer unmet medical needs. Breast Cancer Res Treat 125, 627-636.

Perou, C. M., Sortie, T., Eisen, M. B., van de Rijn, M., Jeffrey, S. S., Rees, C. A., Pollack, J. R., Ross, D. T., Johnsen, H., Akslen, L. A., et al. (2000). Molecular portraits of human breast tumours. Nature 406, 747-752.

Polyak, K., and Weinberg, R. A. (2009). Transitions between epithelial and mesenchymal states: acquisition of malignant and stem cell traits. Nat Rev Cancer 9, 265-273.

Pollak, M. (2008). Insulin and insulin-like growth factor signalling in neoplasia. Nat Rev Cancer 8, 915-928.

Resnik, J. L., Reichart, D. B., Huey, K., Webster, N. J., and Seely, B. L. (1998). Elevated insulin-like growth factor I receptor autophosphorylation and kinase activity in human breast cancer. Cancer Res 58, 1159-1164.

Rowinsky, E. K., Schwartz, J. D., Zojwalla, N., Youssoufian, H., Fox, F., Pultar, P., and Ludwig, D. L. (2011). Blockade of Insulin-Like Growth Factor Type-1 Receptor With Cixutumumab (1MC-A12): A Novel Approach to Treatment for Multiple Cancers. Curr Drug Targets.

Saeki, T., Salomon, D. S., Johnson, G. R., Gullick, W. J., Mandai, K., Yamagami, K., Moriwaki, S., Tanada, M., Takashima, S., and Tahara, E. (1995). Association of epidermal growth factor-related peptides and type I receptor tyrosine kinase receptors with prognosis of human colorectal carcinomas. Jpn J Clin Oncol 25, 240-249.

Sarrio, D., Franklin, C. K., Mackay, A., Reis-Filho, J. S., and Isacke, C. M. (2012). Epithelial and mesenchymal subpopulations within normal basal breast cell lines exhibit distinct stem cell/progenitor properties. Stem Cells 30, 292-303.

Scheel, C., Eaton, E N., Li, S. H., Chaffer, Cl., Reinhardt, F., Kah, K. J., Bell, G., Guo, W., Rubin, J., Richardson, Al., et al. (2011). Paracrine and autocrine signals induce and maintain mesenchymal and stem cell states in the breast. Cell 145, 926-940.

Shankar, S., Nall, D., Tang, S. N., Meeker, D., Passarini, J., Sharma, J., and Srivastava, R. K. (2011). Resveratrol inhibits pancreatic cancer stem cell characteristics in human and KrasG12D transgenic mice by inhibiting pluripotency maintaining factors and epithelial-mesenchymal transition. PLoS One 6, e16530.

Sinn, E., Muller, W., Pattengale, P., Tepler, I., Wallace, R., and Leder, P. (1987). Coexpression of MMTV/v-Ha-ras and MMTV/c-myc genes in transgenic mice: synergistic action of oncogenes in vivo. Cell 49, 465-475.

Sorlie, T., Perou, C. M., Tibshirani, R., Aas, T., Geisler, S., Johnsen, H., Hastie, T, Eisen, M. B., van de Rijn, M., Jeffrey, S. S., et at (2001). Gene expression patterns of breast carcinomas distinguish tumor subclasses with clinical implications. Proc Natl Acad Sci USA 98, 10869-10874.

van Riggelen, J., Yetil, A., and Feisher, D. W. (2010). MYC as a regulator of ribosome biogenesis and protein synthesis. Nat Rev Cancer 10, 301-309.

Vergara, D., Valente, C. M., Tinelli, A., Siciliano, C., Lorusso, V., Acierno, R., Giovinazzo, G., Santino, A., Storelli, C., and Maffia, M. (2011). Resveratrol inhibits the epidermal growth factor-induced epithelial mesenchymal transition in MCF-7 cells. Cancer Lett 310, 1-8.

Visvader, J. E. (2009). Keeping abreast of the mammary epithelial hierarchy and breast tumorigenesis. Genes Dev 23, 2563-2577.

Wang, X., Chao, L., Ma, G., Chen, L., Jin, G., Hua, M., Liu, H., Ouyang, A., and Zhang, X. (2010). Primary breast carcinoma: association of mammographic calcifications with osteopontin expression. Radiology 254, 69-78.

Wong, D. J., Liu, H., Ridky, T. W., Cassarino, D., Segal, E., and Chang, H, Y. (2008). Module map of stem cell genes guides creation of epithelial cancer stem cells. Cell Stem Cell 2, 333-344.

Example 4—Identification of Luminal Breast Cancers that Establish a Tumor Supportive Macroenvironment Defined by Pro-Angiogenic Platelets and Bone Marrow Derived Cells Introduction Breast cancer is a heterogeneous disease that is categorized into molecular and histopathological subtypes based predominantly on analysis of hormone and growth factor receptors—namely estrogen (ER), progesterone (PR), and HER2/Erbb2 (Her2) (1). Women with triple-negative breast cancer (TNBC; i.e. ER−/PR−/Her2−) are at the greatest risk of early recurrence (2). Luminal breast cancers (LBC), which often include ER+ tumors, are the most prevalent form of breast cancer. These tumors are often differentiated and associated with good prognosis, yet some patients with LBC experience recurrent disease even 15-20 years after their initial diagnosis and surgery (3). Although classification into these categories has some correlation with patient outcome, it is difficult to accurately predict which patients will relapse. Furthermore, there is no correlation between molecular classification and patient response to current treatment therapies (4).

In some patients with metastatic breast cancer, tumor cells clearly disseminate prior to surgery, but remain undetected for protracted periods of time before the patient becomes symptomatic (5). Incipient primary tumors and second primary tumors can also exist in a state of indolence before being detected. For example, autopsy studies of people without a medical history of cancer revealed that indolent cancers are highly prevalent within the general population (6). What causes indolent tumors to erupt into overt disease is unknown, making it difficult to predict which cancer patients are likely to relapse or to benefit from preemptive therapy.

The systemic environment is appreciated as an important determinant of tumor malignancy and progression (7). We previously established that indolent cancer cells ("responders") that are disseminated to various anatomical locations within host mice can be stimulated to form malignant tumors as a consequence of aggressively growing triple-negative breast tumors ("instigators") located at distant anatomical sites (8,9). A growing body of evidence supports the notion that tumors that co-exist within a patient who has multiple tumor burden (e.g., multiple disseminated metastases) can interact systemically to modulate overall cancer progression (10). Responding tumor outgrowth occurs as a consequence of systemically-acting cytokines and bone marrow derived cells that are rendered pro-tumorigenic by the instigating triple-negative breast tumors. This cascade of events, termed "systemic instigation", results in the outgrowth of highly desmoplastic, malignant tumors (8). We designed studies to determine if other breast cancer subtypes employ these same mechanisms. A deeper understanding of systemic tumor-promoting processes should improve identification of patients who would benefit from adjuvant therapy.

Materials and Methods

Cell Lines

Generation of HMLER-hygro-H-rasV12 ("HMLER-HR"), BPLER, and MCF7-Ras human mammary epithelial tumor cells have been previously described (11-13). Expression of cytokeratins and introduced oncogenes was validated for these studies; no additional authentication was performed by the authors.

Animals and Tumor Xenografts

Female Nude mice were purchased from Taconic (Hudson N.Y.). All experiments were performed in accordance with regulations of the Children's Hospital Boston Institutional Animal Care and Use Committee (protocol 09-12-1566). Unless otherwise indicated, tumor cells were suspended in 20% MATRIGEL (BD Biosciences) and injected subcutaneously into nonirradiated mice. Tumors were measured on the flanks of live mice using calipers; volume was calculated as $0.5*length*(width^2)$.

Bone Marrow Harvest and Transplantation

BMCs were harvested from donor mice by flushing femurs with sterile Hanks' balanced salt solution (HBBS; GIBCO) with penicillin/streptomycin/fungisone. Cells were washed twice with sterile HBBS, dissociated with 18 g needle, and filtered through 70 μm nylon mesh. Bone marrow transplantation was performed as previously described (9).

Flow Cytometric Analysis

Fresh tissues were digested in 1 mg/ml collagenase A for 1-4 hr at 37° C. with continuous rotation. Resulting cell suspensions were dispersed with an 18 g needle, washed twice with resuspension buffer (2% heat-inactivated fetal calf serum in sterile HBBS) and filtered through 70 μm nylon mesh. Cells were labeled for flow cytometry by incubation with appropriate antibodies for 30 min-1 hr at 4° C. with continuous rotation. Antibodies listed in Table 2.

Immunohistochemistry

Dissected tissues were fixed in 4% paraformaldehyde, embedded in paraffin, and sectioned onto PROBEON Plus microscope slides (Fisher Scientific, Pittsburgh Pa.) for immunohistochemistry using Vectastain Elite ABC kits (Vector Laboratories, Burlingame Calif.) as previously described (9) or ALEXAFLUOR fluorescence-conjugated antibodies (INVITROGEN, Carlsbad Calif.). Antibodies listed in Table 2.

Platelet Preparations

Human and mouse platelets were isolated from whole blood by differential centrifugation as described (47).

Angiogenesis Assay

Platelet releasates and cell conditioned media were tested for induction of human umbilical vein endothelial cells (HUVECs) capillary tube formation on MATRIGEL matrix in vitro using the In Vitro Angiogenesis Assay Kit (Millipore ECM625) according to manufacturer's instructions. Angiogenic ability was quantified by counting branch points, defined as the intersection of three or more capillary tubes. Branch points were counted each hour, from 4-7 hours and data represented as the average number of branch points per sample during the entire experimental time course.

Cytokine Array

Conditioned media or platelet lysates were tested on Human Angiogenesis Antibody Arrays (RayBiotech, Norcross Ga.) according to manufacturer's instructions.

Aspirin Treatment 450 mg Aspirin (Sigma, A2093-100G) was dissolved in 11 ml DMSO to make a 41 mg/ml concentrated stock solution. 30 min before injection, 1.6 ml of stock solution was diluted in 11.6 ml of PBS to make a 5 mg/ml injection solution.

Vehicle control was made with 1.6 ml DMSO diluted in 11.6 ml PBS. Mice were injected i.p. with aspirin at 100 mg/kg, once per week. A similar volume:weight ratio of vehicle was administered to control animals.

Human Breast Cancer and Renal Cell Carcinoma Tumor Specimens

Primary breast tumors were collected and processed shortly after resection in compliance with a protocol approved by the Brigham and Women's Hospital (IRB 93-085). Each tumor was analyzed for ER/PR/HER2 status. cRCC surgical specimens were obtained with patient consent from the Department of Pathology in compliance with a protocol approved by Brigham & Women's Hospital, Boston Mass. (DFCI IRB #01-130). All specimens were used without patient identifiers. Tumors were cut to 3-4 mm pieces, washed in RPMI, and frozen in RPMI+10% DMSO. For xenograft studies, tumor specimens were quickly thawed at 37° C., washed 3 times in RPMI, and minced finely into <1 mm organoids to ensure tissue homogeneity. Organoids were divided into equal portions, transferred to individual wells of a 96-well plate, covered with 50% MATRIGEL in RPMI media, and incubated for 10 min at 37° C. to form cohesive plugs. One organoid plug was selected at random to confirm that samples contained viable tumor cells. Remaining organoid plugs were surgically implanted beneath the skin of Nude mice following sterile surgical procedure as previously described (9).

Statistical Analyses

Data are expressed as mean±SEM. Data were analyzed by Student's t-test and were considered statistically significant if $p<0.05$.

Results

Breast Cancer Subtype Determines Disseminated Tumor Phenotype

Figure 30:
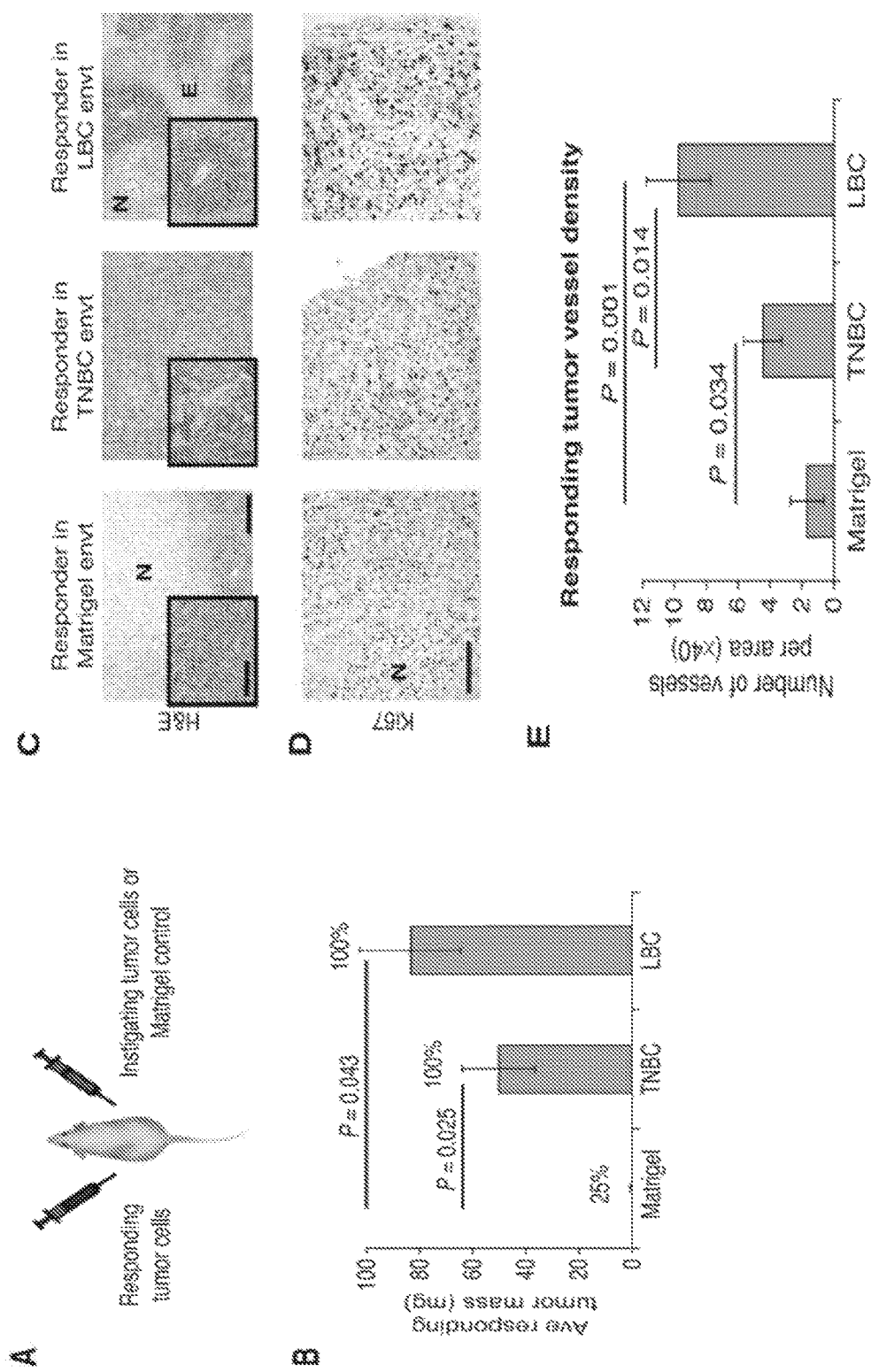
FIGS. 30A-30G. Breast cancer subtype-specific systemic environments affect bone marrow derived cells and phenotype of otherwise indolent tumors at distant sites.
Figure 30:
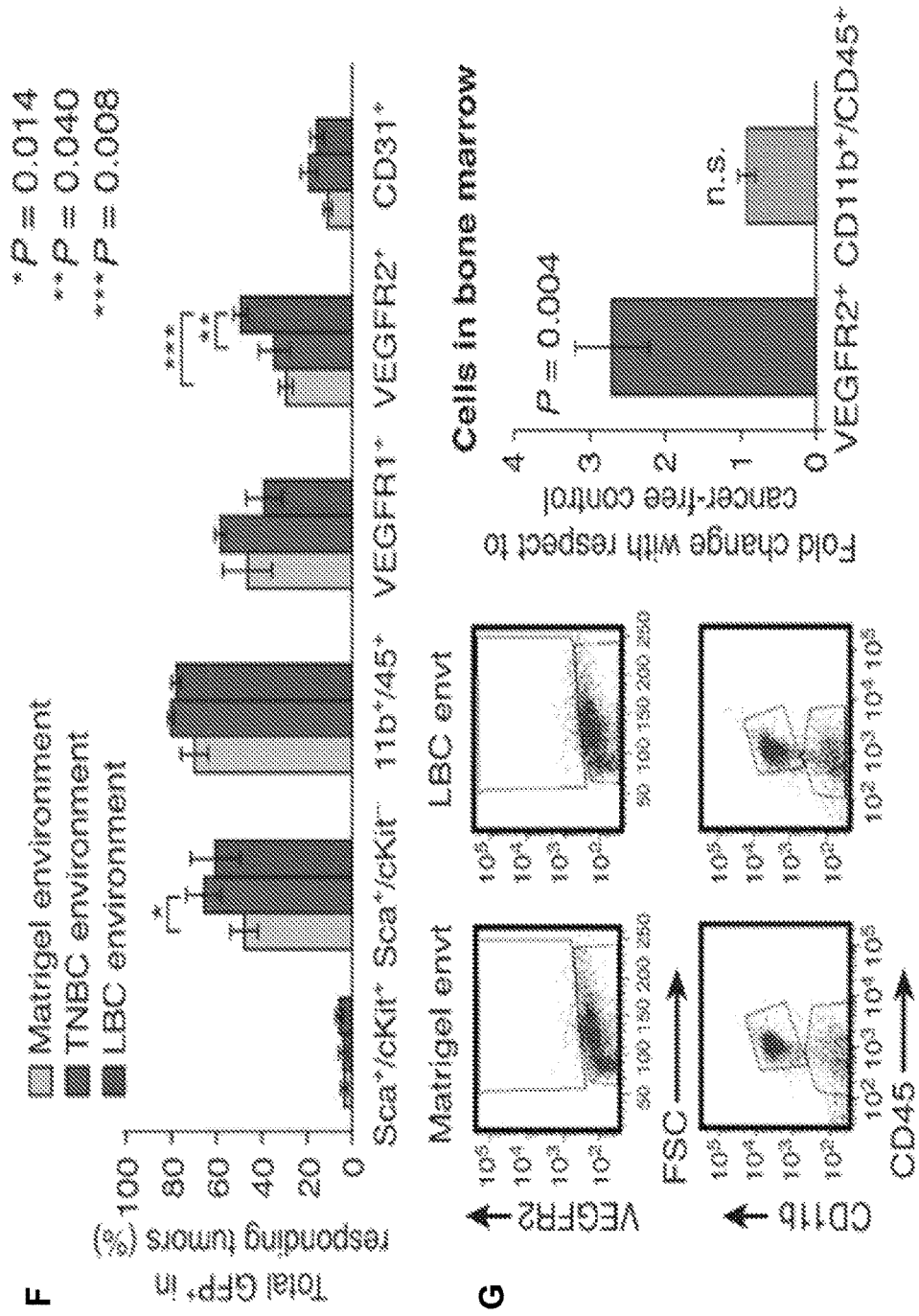

In order to understand whether luminal breast cancers (LBC) exert similar pro-tumorigenic systemic effects as instigating triple-negative breast cancers (TNBC), we injected responding human breast cancer HMLER-HR cells (9,11) contralaterally to either LBC tumor cells (MCF7Ras (12)), TNBC tumor cells (BPLER (13)), or MATRIGEL vehicle control in Nude mice, according to our human tumor xenograft protocol (FIG. 30A. tissue from 3 of the 4 mice that had been injected with responding tumor cells opposite MATRIGEL control were recovered; however, microscopic analysis revealed that only one tissue plug contained a small responding tumor (~10 mg) while the other two did not form bone fide tumors (FIG. 30B). Responding cells formed tumors in 100% of the mice bearing the systemic environments established by TNBC and LBC (FIG. 30B). Importantly, the resulting responding tumors were formed by the human responder cells that had been injected (data not shown).

Responding tumors that were instigated by TNBC displayed no observable necrosis and were moderately mitotic (FIGS. 30C and 30D). As it was observed previously (8), these responder tumors formed a desmoplastic stroma infiltrated by alpha-smooth muscle actin (αSMA)-positive myofibroblasts (data not shown). In contrast, responding tumors growing in the LBC environment had areas of observable edema and necrosis, and were highly mitotic (FIGS. 30C and 30D). These responding tumors were extensively vascularized without forming desmoplastic stroma (FIG. 30C). These histopathological phenotypes were consistent with breast adenocarcinomas observed in the clinic (2). The control tumor recovered from the MATRIGEL environment was comprised of viable responder cells only at the tumor periphery (FIGS. 30C and 30D).

The differences in responding tumor histopathology suggested that LBC might employ different systemic tumor-promoting mechanisms than TNBC. Indeed, levels of the cytokine osteopontin (OPN), an endocrine factor that is necessary for TNBC-dependent systemic instigation (9) were secreted at ~450-fold lower levels from the LBC tumor cells than from the TNBC tumor cells (p=0.002) and were no different than that of the responding tumor cells (data not shown).

VEGFR2-Positive Cells Incorporate into Vasculature in LBC-Instigated Tumors

Tumors that responded to the TNBC environment had significantly higher vessel density than the control tissues (~2.6-fold); however, those in the LBC environment had higher microvessel density than either control tissues (5.7-fold, p=0.001) or TNBC-induced tumors (2.2-fold, p=0.014) (FIG. 30E). Blood vessels in the LBC-induced responding tumors contained few CD31-positive cells, were weakly positive for mouse endothelial cell antigen (Meca32), and lacked pericyte coverage, as indicated by the absence of associated αSMA-positive cells (data not shown) even though peri-tumoral vasculature stained strongly for MECA32 and αSMA (data not shown). Therefore, responding tumors were examined for the presence of vascular endothelial growth factor receptor 2 (VEGFR2)-positive cells, which aid the formation of blood vessels to varying extents under different pathological conditions (14). In the tumors that responded to LBC-dependent systemic instigation, the vast majority of blood vessels were comprised of VEGFR2+ cells (data not shown). Vasculature in the tumors instigated by TNBC was predominantly devoid of VEGFR2+ cells (data not shown).

VEGFR2+ endothelial precursor cells have been shown to originate in the bone marrow (14, 15) and their elevated numbers in the circulation correlate with advanced stage in patients with invasive breast cancer (16). Therefore, the recruitment of bone marrow derived cells (BMDCs) into the various responding tumors in Nude mice that had been successfully engrafted with GFP+BMCs prepared from eGFPRag1−/− mice were examined (data not shown). Tissue plugs were recovered 4 weeks after injection of the responding tumor cells, when the average tissue mass in each group was 10 mg (not shown). In the plugs extracted from sites where responding tumor cells had been injected contralaterally to MATRIGEL, only ~5% of the total cellular portion of these tissues was comprised of GFP+BMDCs (data not shown). The numbers of BMDCs in these tissues were not significantly different from those of the contralateral MATRIGEL plug or control lung tissues, which contained ~3% GFP+ cells (data not shown). In contrast, BMDCs were incorporated to a significantly greater extent into responder tumors promoted by both TNBC (p=0.006) and LBC (p=0.012) instigators; ~20% of the total cellular portion of these tumors was comprised of GFP+ bone marrow-derived cells (data not shown).

In responding tumors from the LBC environment, VEGFR2+ cells comprised ~50% of the total number of GFP-positive BMDCs (FIG. 30F). These numbers represented a 39% increase above those of TNBC-induced tumors and a 67% increase above tissues in the MATRIGEL environment. In consonance with our earlier report (8), pro-tumorigenic Sca1+/cKit− hematopoietic BMDCs were incorporated to a significantly greater extent into responding tumors stimulated by TNBC than those recovered opposite MATRIGEL (FIG. 30F). The contributions of CD11b+/CD45+, Sca+/cKit+, VEGFR1+, and CD31+ cells to the total GFP+BMDC population were not significantly different between the cohorts of mice (FIG. 30F).

VEGFR2+ cells were also ~2.7-fold more abundant in the bone marrow of mice bearing LBC tumors than in those bearing TNBCs or MATRIGEL control (FIG. 30G). The numbers of other BMC populations in the marrow, such as CD11b+/CD45+ myeloid cells, were not statistically different between groups (FIG. 30G).

Collectively, these data indicated that luminal breast tumors mediated the expansion of VEGFR2+ bone marrow cells that were subsequently mobilized to distant responding tumor sites. Within the responding tumor microenvironment VEGFR2+ cells contributed, at least in part, to the formation of tumor vasculature.

LBC Enhances Platelet Recruitment to Responding Tumors

The plasma levels of some common pro- and anti-angiogenic circulating cytokines were analyzed as potential mediators of systemic instigation in the LBC environment but found no statistically significant differences between cohorts (data not shown). Others have shown that proteins, including angiogenic regulators, are enriched several hundred-fold in circulating platelets as compared to the plasma and that platelets are potent mediators of angiogenesis (17-19); therefore it is possible that platelets were ideal candidates as mediators of systemic instigation.

Figure 31:
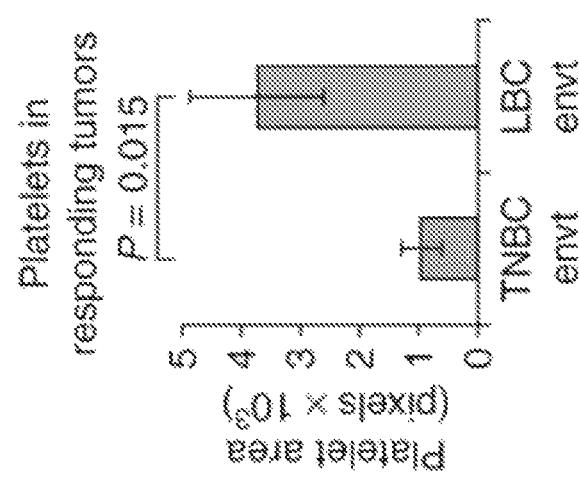
FIG. 31. Platelets are recruited to responding tumors during LBC systemic instigation. CellProfiler software outlines of p-selectin-positive areas used for quantification. Graph represents average p-selectin-positive area per immunofluorescent image of responding tumors in indicated macroenvironments stained for p-selectin to visualize platelets; TNBC n=15 images; LBC n=19 images.

Responding tumors that formed as a consequence of LBC instigation recruited ~3.7-fold more platelets than those stimulated by TNBC (FIG. 31). Responding tumors were therefore analyzed for expression of ligands that are known to mediate platelet adhesion, including collagen IV (ColIV) and CD24. ColIV is a potent chemoattractant that recruits platelets to injured vessels during wound healing or tumor formation (20). CD24 is a cell surface glycoprotein that is used as a surrogate marker for differentiation status of breast and other cancer cells (21) and can bind to the platelet-expressed adhesion molecule, p-selectin (22).

The vast majority of blood vessels within the responding tumors instigated by LBC contained areas of exposed collagen, whereas collagen deposition was predominantly confined to the intra-tumoral extracellular matrix in responders from the MATRIGEL and TNBC environments (data not shown). Moreover, carcinoma cells from responding tumors that had been instigated by LBC were highly enriched for cell surface expression of CD24, particularly in areas surrounding blood vessels (data not shown), when compared with those injected opposite TNBC or MATRIGEL control, in which CD24 expression was limited to a few responding cells (data not shown). Platelets were observed within these CD24- and ColIV-rich areas of LBC-instigated responding tumors compared to similar areas in control responding tumors in which p-selectin-positive platelets were not obvious (data not shown), even though circulating platelet counts were elevated in both cohorts relative to cancer-free mice (data not shown).

These results indicated that different tumor-promoting systemic environments had a profound impact on the ability of tumor cells to recruit platelets.

Platelets are Rendered Pro-Angiogenic by Instigating LBC Tumors

Figure 32:
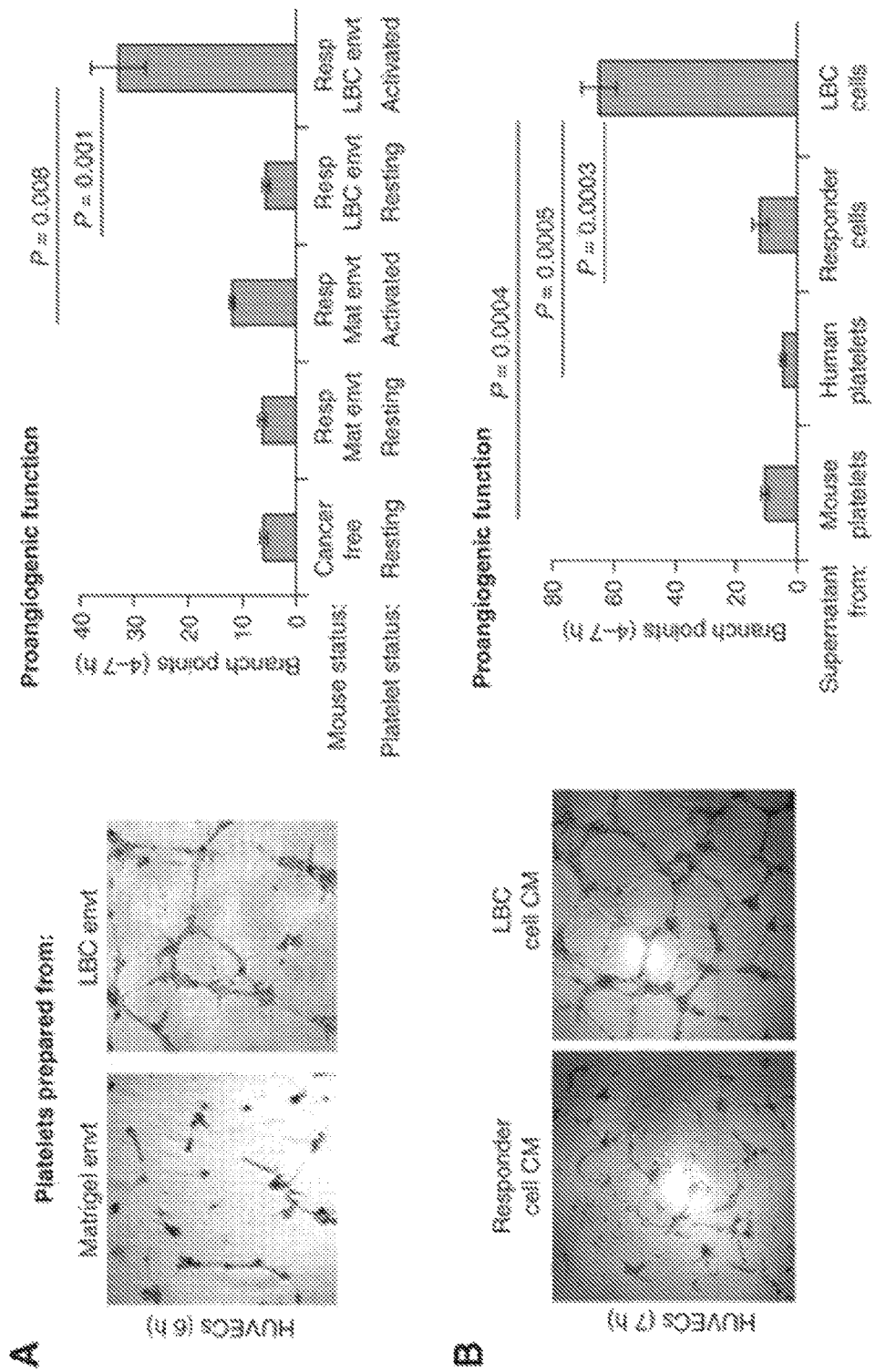
FIG. 32A-32E. Platelets in the LBC environment are enhanced for pro-angiogenic function and take up pro-angiogenic factors secreted by LBC tumor cells.
Figure 32:
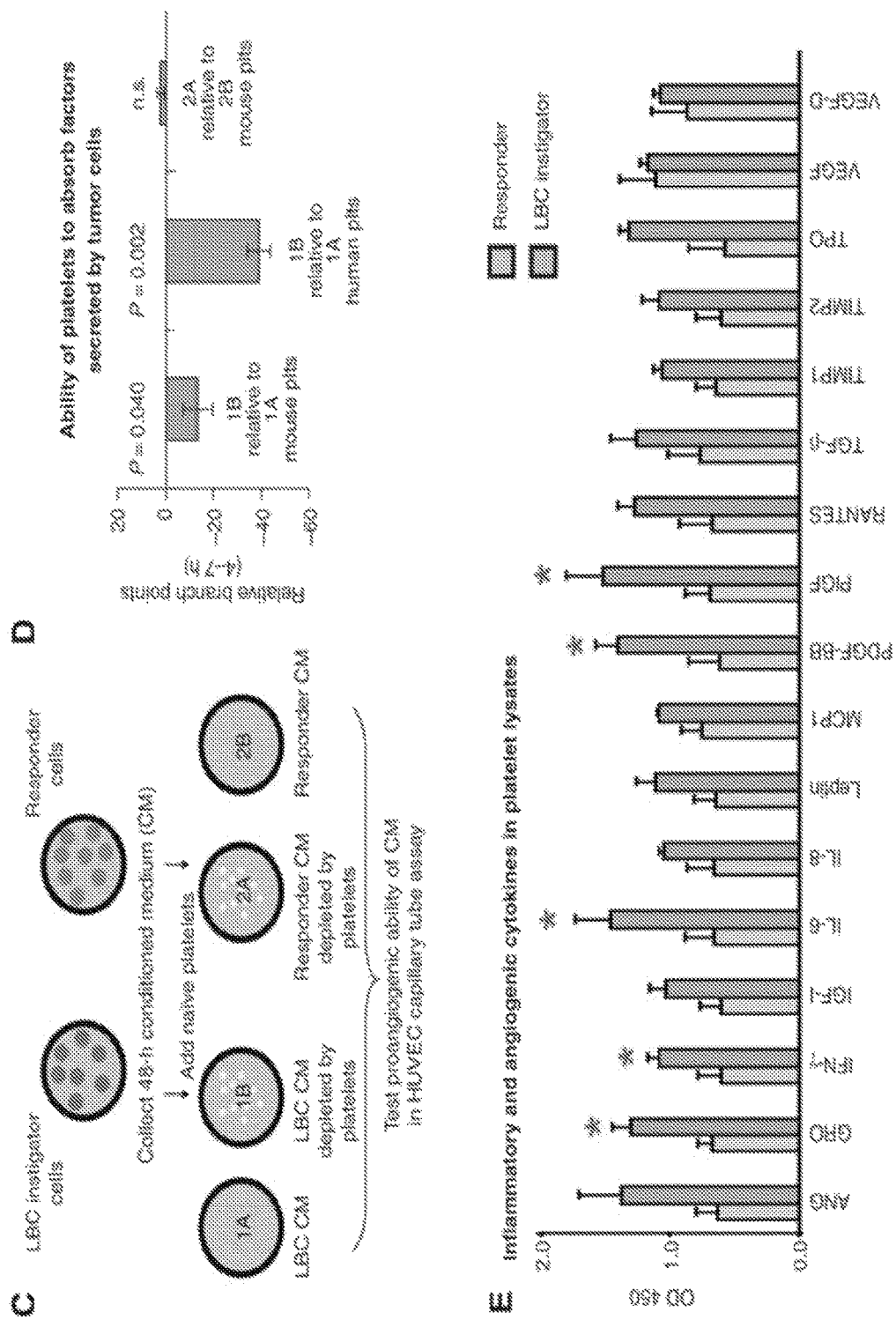

The fact that platelets had selectively accumulated in responding tumors exposed to the LBC systemic environment suggested that they might play a functional role in tumor promotion. Hence, the ability of platelets, prepared from various tumor-bearing mice, to stimulate angiogenesis were analyzed, using a standard in vitro human umbilical vein endothelial cell (HUVEC) assay. Resting platelets harvested from cancer-free mice and from mice bearing responding tumors opposite either MATRIGEL control or LBC tumors induced capillary tube formation to similar extents (FIG. 32A). ADP-activated platelets from mice bearing responding tumors opposite MATRIGEL control were unable to stimulate angiogenesis above baseline controls (FIG. 32A). In significant contrast, ADP-activated platelets from mice bearing LBC tumors had ~4-fold enhanced angiogenesis-promoting ability (FIG. 32A).

In light of this striking result, the source of the platelet pro-angiogenic potential was investigated, primarily whether the potential was directly imparted by instigating LBC tumors. First, the pro-angiogenic capacity of conditioned medium (CM) from cultured cells were assessed. As controls, medium from resting mouse and human platelets prepared from cancer-free subjects were used, which minimally promoted capillary tube formation (FIG. 32B). The CM from responding tumor cells did not significantly enhance in vitro angiogenesis to any extent above that of the control CM from resting platelets (FIG. 32B). In sharp contrast, CM from LBC cells significantly enhanced in vitro angiogenesis by ~6.5-fold above that of the responder cells or resting platelet controls (FIG. 32B).

Next, the platelets were tested for its capability of taking up pro-angiogenic factors released by instigating LBC tumor cells. The experiment comprised co-culturing naïve, cancer-free mouse or human platelets with either responder or instigator cells in vitro. The supernatants from these co-cultures were interrogated for their ability to induce capillary tube formation, reasoning that if platelets absorbed pro-angiogenic factors from the medium, then supernatants from LBCs would have reduced angiogenic capacity following their exposure to platelets (FIG. 32C). Naïve platelets did not significantly alter the angiogenic ability of the responding tumor cell CM, which was negligible (FIG. 32B, 32D). Supernatants from LBC instigating cells, which were otherwise highly pro-angiogenic (FIG. 32B), exhibited ~15-fold and ~40-fold reductions in angiogenic ability when the LBC cells were cultured with naive mouse or human platelets, respectively (FIG. 32D). These results were consistent with previous reports (17) and established that both human and mouse platelets were capable of packaging pro- and anti-angiogenic factors secreted by LBC tumor cells.

In order to identify pro-angiogenic factors carried by platelets during LBC systemic instigation, a human cytokine array were performed on various platelet lysates. When compared to platelets from mice bearing responding tumors (no systemic instigation), a number of pro-angiogenic and pro-inflammatory human cytokines were significantly more concentrated in the platelets from mice bearing LBC instigating tumors, including GRO (p=0.012), IFNg (p=0.050), IL6 (p=0.044), PDGF-BB (p=0.033), and P1GF (p=0.044) (FIG. 32E). These results were validated by immunostaining platelets prepared from the various cohorts of mice (data not shown). Notably, platelet-derived levels of vascular endothelial growth factor (VEGF) and thrombospondin (TSP), the most extensively studied pro- and anti-angiogenic cytokines, respectively, were not significantly different between cohorts (FIG. 32E).

In order to understand whether some of these cytokines were functioning at responding tumor sites, the activation status of signal transducer and activator of transcription 3 (STAT3) was examined; STAT3 plays an important tumor-supportive role in both breast tumor cells and in the tumor microenvironment (23,24). STAT3 is a downstream effector of growth factor receptors for cytokines identified in our screen, including IL6 and PDGF (25). Using an antibody specific to the activated, phosphorylated form of both human and mouse STAT3 (p-STAT3), it was noted that the levels of p-STAT3 were negligible in control responding tumors opposite MATRIGEL or TNBC (data not shown). In marked contrast, p-STAT3 staining was abundant in responding tumors that grew contralaterally to LBC tumors, and was localized predominantly to the nucleus of stromal cells within these tumors (data not shown). There was no significant difference in p-STAT3 levels when comparing BMCs from mice bearing the LBC instigating tumors to those of cancer-free controls (data not shown), suggesting that the enhancement of STAT3 activity observed in the LBC-bearing mice did not occur in BMCs prior to their mobilization.

Taken together, these data established that LBC tumors loaded platelets with pro-inflammatory and pro-angiogenic factors and provided evidence that these factors were released at distant responding tumors sites. Despite equal concentrations of VEGF and TSP in platelets from both groups, platelets from LBC-bearing hosts had far greater pro-angiogenic activity, thus underscoring the importance of the complete repertoire of cytokine cargo carried by platelets under different pathological conditions.

BMC-LBC Mediate Enrichment of CD24+ Responding Tumor Cells

A paradigm of TNBC-mediated systemic instigation is that BMCs (specifically Sca1+/cKit− cells) are rendered pro-tumorigenic prior to mobilization from the marrow into the circulation; hence, when BMCs from hosts bearing TNBCs are admixed with responder cells prior to injection, the BMCs mimic the effects of the TNBC instigating tumors (8). The BMCs were therefore tested for whether its recruitment into responding tumors (data not shown) played an active role in the LBC systemic instigation process. To do so, admixtures of responder cells and BMCs prepared from various mice were injected into nude mice and tested for their tumor-promoting ability (FIG. 33A).

Figure 33:
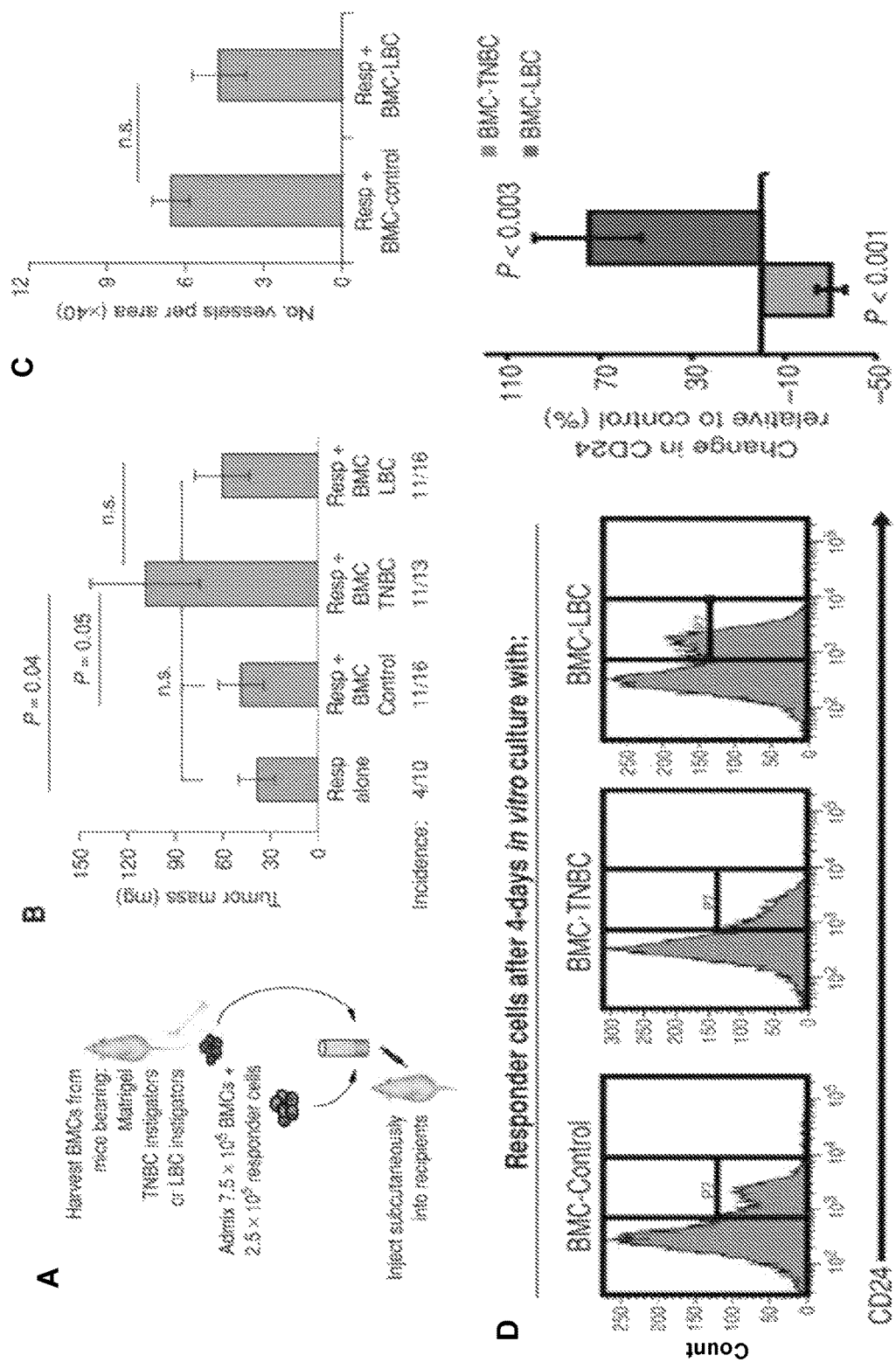
FIGS. 33A-33D. BMCs from mice bearing LBC tumors enrich responding tumor cells for CD24 surface expression but lack instigating ability.

BMCs prepared from mice bearing TNBC (BMC-TNBC) were sufficient for responding tumor growth (FIG. 33B). Responding tumors formed in 85% of these mice and tumors were ~2.8-fold larger than those that had formed on their own (40% incidence) or that had been admixed with BMCs from cancer-free hosts (68% incidence) (FIG. 33B). BMCs from mice bearing LBC tumors (BMC-LBC), however, did not significantly enhance incidence (68%) or mass of responding tumors above that of the cancer-free control BMCs (FIG. 33B). Nevertheless, consistent with the enrichment of CD24 on responder cells in the LBC environment (data not shown), CD24 was likewise enriched on the surface of responding tumor cells that had been admixed with the BMC-LBCs (data not shown), and p-selectin-positive platelet aggregates were localized to the CD24-rich areas of these tumors (data not shown). The area covered by CD24+ cells in responding tumors admixed with BMCs from control mice was not as extensive as that of tumors admixed with BMC-LBC; consequently, fewer platelets were observed in the control tumors (data not shown).

In order to understand whether BMCs from LBC tumor bearing mice directly mediated tumor cell surface enrichment of CD24, adherent GFP-positive (GFP+) responding tumor cells were cultured with BMCs prepared from various cohorts of mice and analyzed tumor cell expression of CD24 after 4 days by flow cytometry. Responding cells that had been cultured with BMCs harvested from TNBC-bearing mice (BMC-TNBC) displayed a ~30% decrease in CD24 expression (FIG. 33D), while exposure to BMCs from LBC-bearing mice (BMC-LBC) resulted in a ~75% increase in the CD24-positive responding cell population relative to controls (FIG. 33D).

Hence, BMCs from mice bearing LBC tumors were necessary and sufficient to enrich CD24-positive responding tumor cells, which recruited platelets. Nevertheless, these events were not sufficient to enhance responding tumor malignancy. The resulting tumors were further examined for additional hallmarks of LBC-mediated tumor-promotion. While VEGFR2 cells were more abundant in the tumors that had been admixed with BMC-LBC, they did not appear to incorporate into tumor vasculature (data not shown). The numbers of phosphorylated STAT3-positive cells, an indicator for the presence of pro-angiogenic platelets, were minimal and no different in the BMC-LBC admixed tumors than they were in the BMC-control admixed tumors (data not shown). Consequently, there was no difference in tumor vessel density between the two cohorts (FIG. 33C) and in both cases, fewer vessels were apparent than in the tumor-promoting LBC systemic environment (FIG. 30E).

These findings indicated that without the stimulus provided by the LBC tumor, the platelets were not loaded with angiogenesis-promoting cargo and that instigating tumor-educated platelets were crucial for systemic promotion of responding tumor growth.

Instigating and Non-Instigating Primary Human Luminal Breast Cancers

Figure 34:
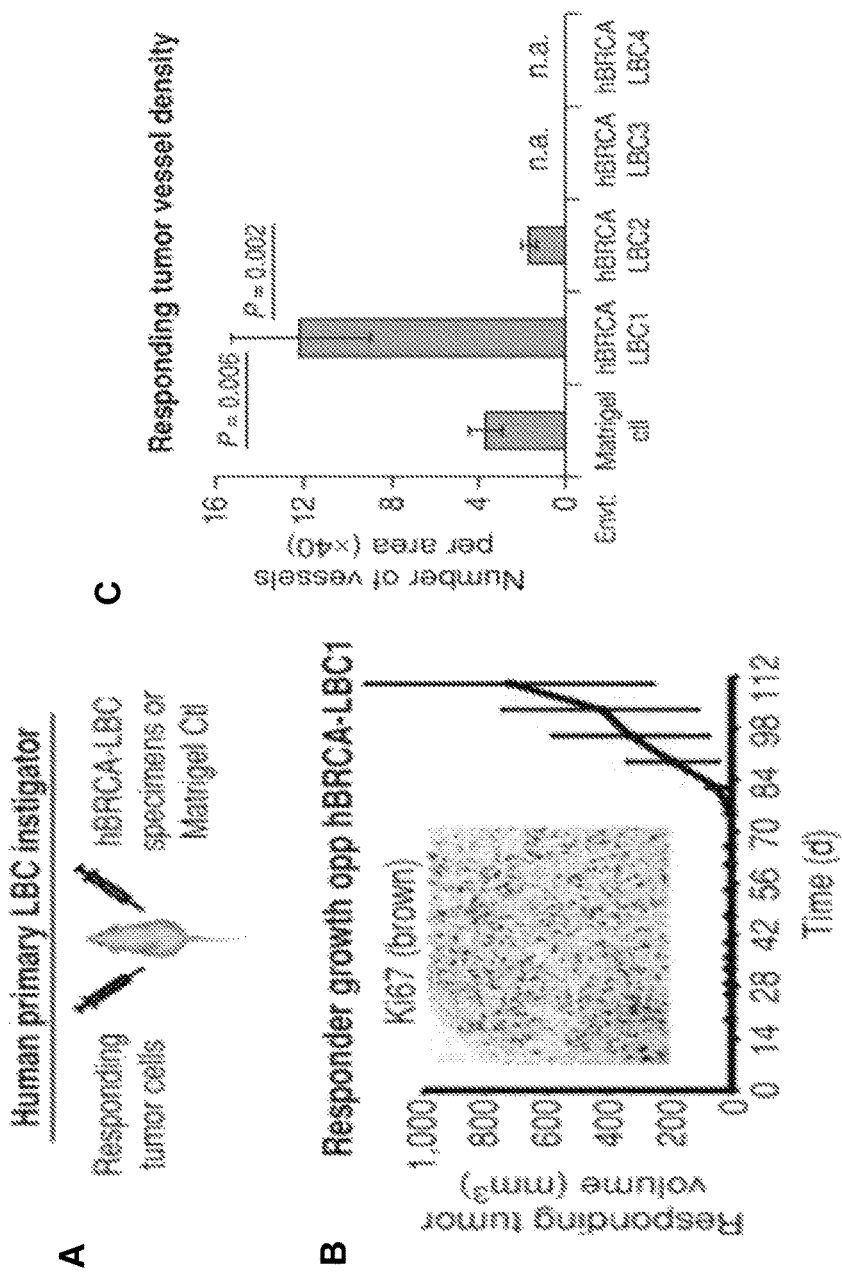
FIGS. 34A-34I. Instigating, non-instigating, and responding human tumor specimens.
Figure 34:
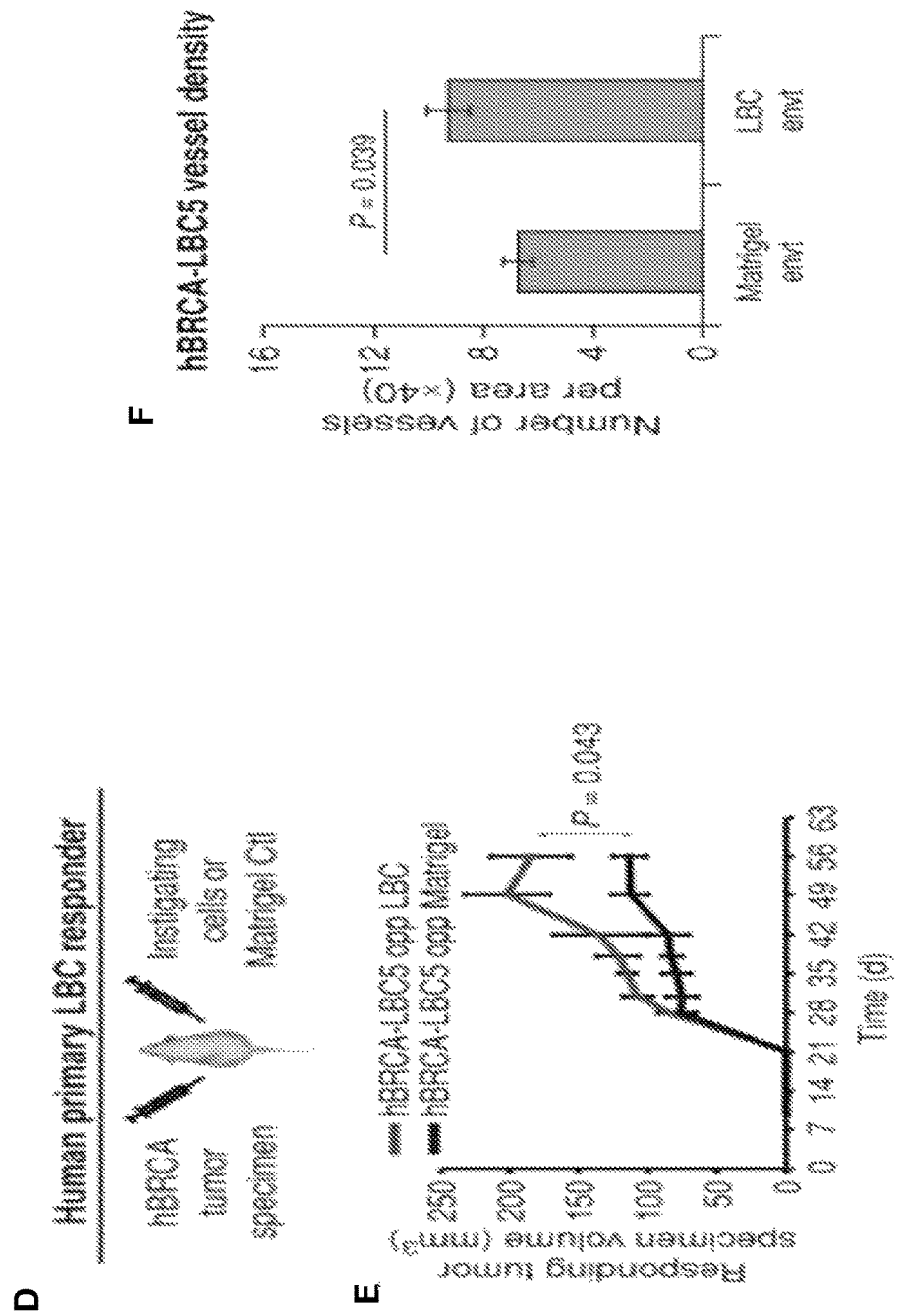
Figure 34:
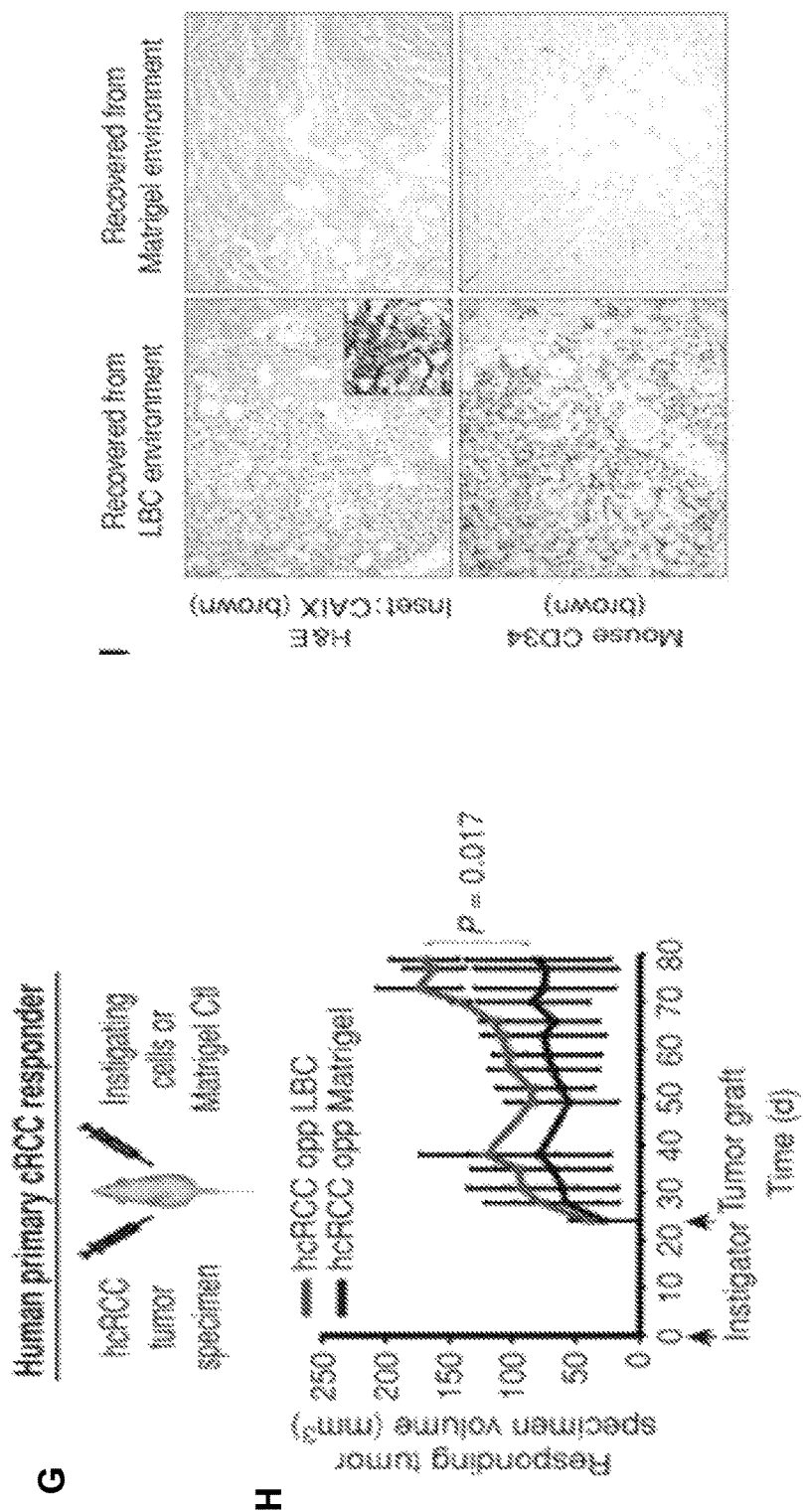

In order to understand whether this type of systemic instigation processes might reflect real human tumor behavior, 4 different primary human tumor specimens from patients with luminal breast cancer (hBRCA-LBC 1-4) were tested for their ability to establish a pro-tumorigenic macroenvironment. To do so, human tumor specimens or MATRIGEL control plugs were surgically implanted subcutaneously into Nude mice contralaterally to responding human cells (FIG. 34A). These patient tumors were diagnosed as invasive ductal carcinoma, grade II/III, positive for ER and PR, with differing HER2 status, and each human tumor specimen retained its morphological characteristics and cytokeratin expression in the mice (data not shown).

One tumor, hBRCA-LBC1, established a pro-tumorigenic environment that supported growth of highly proliferative responding tumors in 100% (3/3) of the mice (FIG. 34B). This instigating tumor specimen exhibited identical growth kinetics whether it was implanted opposite MATRIGEL control or opposite the responding tumor cells (data not shown). One (1/3) responding tumor was recovered opposite hBRCA-LBC2, none (0/3) were recovered opposite hBRCA-LBC3 or hBRCA-LBC4, and three (3/3) tissue plugs were recovered in the MATRIGEL control conditions.

All of the tumors that responded to hBRCA-LBC1 displayed hallmarks of LBC-mediated tumor promotion, including CD24 enrichment, p-selectin positive platelet aggregates, phospho-STAT3 positivity, and vessels marked by exposed collagen and incorporation of VEGFR2-positive cells when compared with the tumor recovered opposite non-instigating hBRCA-LBC2, in which enrichment of these hallmarks was not observed (data not shown). Consequently, microvessel density in the responding tumors from the instigating hBRCA-LBC1 environment was significantly higher than those of the MATRIGEL (~3.4-fold) or non-instigating hBRCA-LBC2 (~7.2-fold) environments (FIG. 34C).

These results provided important evidence that primary tumor xenografts could be stratified based on their ability to establish a pro-tumorigenic systemic environment that promoted vascularization and growth of distant disseminated tumors.

Identification of Responding Tumors from Cancer Patients

The results indicated that populations of cells that disseminate from a primary tumor in a patient with metastatic disease could respond to systemic signals to convert from a state of indolence to one of overt growth. To test this theory, a tumor specimen from a patient with luminal breast cancer (hBRCA5, data not shown) that remained indolent when implanted into tumor-free control mice (not shown) was selected. From this tumor, organoids (see Methods) were prepared and surgically implanted beneath the skin of Nude mice bearing either instigating LBC tumors or control MATRIGEL plugs on the contralateral flanks (FIG. 34D).

All of the hBRCA5 organoids implanted into the LBC environment formed aggressively growing tumors that were significantly larger than the control organoids (FIG. 34E) and displayed all of the hallmarks of the LBC-mediated response. Specifically, the instigated hBRCA5 tumors were enriched for CD24, phospho-STAT3-positive cells, vessels with exposed collagen, VEGFR2-positive vessel cells, and p-selectin platelet aggregates compared with hBRCA5 organoids in the control environment (data not shown). Moreover, the instigated tumors had a subtle yet significant increase (~38%) in vessel density than the counterpart control tissues (FIG. 34F).

Clear cell renal cell carcinoma (cRCC) is typically a highly vascularized cancer. In cRCC patients, levels of circulating VEGFR2+ progenitor cells correlate with outcome (26) and tumor cell enrichment of CD24 correlates with reduced progression free survival (27). We therefore tested the hypothesis that organoids prepared from a nephrectomy surgical specimen, taken from a patient with cRCC, would take advantage of the pro-angiogenic systemic macroenvironment established by instigating LBC tumors. cRCC organoids were surgically implanted beneath the skin of Nude mice bearing either instigating LBC or control macroenvironments (FIG. 34G). One random organoid sample was selected for histology to confirm that all animals received approximately equal portions of tumor tissue (data not shown).

cRCC tissues recovered from mice bearing the LBC systemic environment were ~2-fold larger in volume and in mass than those that had been implanted opposite MATRIGEL control (FIG. 34H). Microscopic examination revealed the presence of tumor cell nodules in two of four grafts implanted in LBC tumor bearing mice but in none of the three grafts implanted in mice bearing MATRIGEL plugs (FIG. 34I, top panels). Moreover, sparse cells with morphological features compatible with cRCC were detected in the other two LBC-instigated grafts that did not contain tumor nodules and in one of the grafts implanted opposite MATRIGEL control (not shown).

Immunohistochemical analysis demonstrated that the tumor cells composing the nodules within the LBC-instigated grafts expressed the cRCC marker Carbonic Anhydrase IX (CAIX) (FIG. 34I, inset), and thus retained immunophenotypic features of the fresh tumor sample removed from the patient (data not shown) Immunohistochemical labeling of mouse-derived CD34-positive cells revealed that one of the tumor nodules displayed high density of microvessels lined by murine endothelial cells compared with grafts implanted opposite MATRIGEL control (FIG. 34I, bottom panels).

Collectively these data indicated that human tumor breast cancer and clear cell renal carcinoma specimens that otherwise did not form successful grafts were able to take advantage of a pro-tumorigenic systemic environment to form vascularized, growing tumors.

Platelet Activity is Necessary for LBC-Mediated Systemic Instigation

In order to explore therapeutic potential and identify whether platelets were necessary for delivering the pro-tumorigenic instigating stimulus in the LBC macroenvironment, we treated mice with aspirin, which inhibits platelet activity (28). Mice were injected with LBC instigators that were permitted to grow for 4 weeks prior to initiation of weekly treatments of either aspirin or vehicle control; responders were then injected into these mice two days following the first aspirin treatment (FIG. 35A). While responding tumors formed in 90% of the mice treated with vehicle control, only 20% of the mice treated with aspirin developed responding tumors (FIG. 35B). Importantly, aspirin did not significantly affect instigating LBC tumor growth or circulating platelet counts in the two cohorts of mice (data not shown).

As expected, responding tumors growing contralaterally to instigating LBC from vehicle treated mice recruited VEGFR2-positive cells and were infiltrated with p-STAT3 positive stromal cells (data not shown). In stark contrast, aspirin treatment completely inhibited the incorporation of VEGFR2-positive cells into responding tumor sites (data not shown). These tissues were also negative for p-STAT3, suggesting that release of platelet-derived cytokines had not taken place at these tumor sites, as it had in the vehicle-treated controls (data not shown).

Inhibition of responding tumor growth in response to aspirin was not due to a suppression of VEGFR2 cells in the marrow, as the numbers of VEGFR2-positive cells in the marrows of both vehicle-treated and aspirin-treated mice were ~2-fold higher than cancer-free mice and were not significantly different from one another (FIG. 35C). Moreover, aspirin treatment did not affect the ability of BMCs to enrich responding cell CD24 surface expression; tumor cells cultured with BMCs from either vehicle or aspirin treated mice had a ~90% increase in CD24 expression above those exposed to control BMCs from tumor-free mice, (FIG. 35D).

These results established that platelets mediated critical steps in the LBC-mediated systemic instigation cascade. Under instigating conditions, aspirin did not affect the instigating tumor or the activity of tumor-supportive VEGFR2+ cells in the marrow. Instead, platelet activity manifested most predominantly at the responding tumor site, where platelets were necessary for releasing pro-angiogenic cytokines and recruiting vessel-forming VEGFR2+ cells that facilitated the conversion from indolence to malignancy.

In conclusion, the inventors describe a functional role for the systemic macroenvironment modulated by primary tumors that can ultimately determine growth and phenotype of secondary tumors (FIG. 36). In the presence of an instigating LBC tumor: i) circulating platelets are loaded with a repertoire of cytokines that significantly enhances their pro-angiogenic ability, and ii) the bone marrow is marked by an elevated number of VEGFR2+ cells. At the sites where otherwise indolent tumors reside, the pro-angiogenic platelets accumulate, most likely in response to exposed collagen and tumor cell CD24 presentation. Bone marrow cells play a two-part role: i) to provide VEGFR2+ cells that form the vasculature in response to pro-angiogenic factors, and ii) to mediate enrichment of tumor cell CD24, which can serve to recruit the pro-angiogenic platelets.

The significance of our results using instigating and responding primary human breast tumor specimens is supported by clinical observations that surgical resection of primary tumors improved the survival of women who presented with metastatic breast cancer at the time of diagnosis (29). Analysis of metastatic tumors from breast cancer patients demonstrated that CD24 expression is enhanced on tumor cells at metastatic sites relative to those in the primary tumor (30). CD24 has also been correlated with increased metastatic potential and reduced survival in both breast cancer (31,32) and cRCC (27) patients. Our study is the first to show that tumor cell enrichment of CD24 has important functional consequences and is directly driven by bone marrow derived cells—and not just any bone marrow cells, but only those from hosts bearing instigating luminal breast cancers.

cRCC is another example of a cancer for which surgical removal of the primary tumor (i.e., cytoreductive nephrectomy) improves patient outcome when performed prior to cytokine therapy (33,34). By demonstrating that human cRCC surgical specimens benefit from the macroenvironment established by instigating luminal breast cancers, we do not imply that the mechanisms of systemic instigation apply only to patients with concurrent breast and renal cell carcinoma. Rather, other cancer types, such as cRCC, might operate in a similar fashion to that of instigating luminal breast cancers to support the outgrowth of disseminated tumor cells. Indeed, systemic instigation processes might not only apply to the communication system between a primary tumor and its metastases, but between primary tumor foci (i.e, multifocal tumors), multiple primary tumors (i.e., contralateral breast cancer), or different metastatic colonies (7).

The references cited herein and throughout the specification are incorporated herein by reference.

References

1. Perou C M, Sorlie T, Eisen M B, van de Rijn M, Jeffrey S S, Rees C A, et al. Molecular portraits of human breast tumours. Nature 2000; 406: 747-52.
2. Foulkes W D, Smith I E, and Reis-Filho J S. Triple-negative breast cancer. N Engl J Med 2010; 363: 1938-48.
3. Lowery A J, Kell M R, Glynn R W, Kerin M J, and Sweeney K J. Locoregional recurrence after breast cancer surgery: a systematic review by receptor phenotype. Breast Cancer Res Treat 2011; 133: 831-41.
4. Sorlie T, Wang Y, Xiao C, Johnsen H, Naume B, Samaha R R, et al. Distinct molecular mechanisms underlying clinically relevant subtypes of breast cancer: gene expression analyses across three different platforms. BMC Genomics 2006; 7: 127.

5. Pantel K, Brakenhoff R H, and Brandt B. Detection, clinical relevance and specific biological properties of disseminating tumour cells. Nat Rev Cancer 2008; 8: 329-40.
6. Nielsen M, Thomsen J L, Primdahl S, Dyreborg U, and Andersen J A. Breast cancer and atypia among young and middle-aged women: a study of 110 medicolegal autopsies. Br J Cancer 1987; 56: 814-9.
7. Castano Z, Tracy K, and McAllister S S. The tumor macroenvironment and systemic regulation of breast cancer progression. Int J Dev Biol 2011; 55: 889-97.
8. Elkabets M, Gifford A M, Scheel C, Nilsson B, Reinhardt F, Bray M A, et al. Human tumors instigate granulin-expressing hematopoietic cells that promote malignancy by activating stromal fibroblasts in mice. J Clin Invest 2011; 121: 784-99.
9. McAllister S S, Gifford A M, Greiner A L, Kelleher S P, Saelzler M P, Ince T A, et al. Systemic endocrine instigation of indolent tumor growth requires osteopontin. Cell 2008; 133: 994-1005.
10. McAllister S S, and Weinberg R A. Tumor-host interactions: a far-reaching relationship. J Clin Oncol 2010; 28: 4022-8.
11. Elenbaas B, Spirio L, Koerner F, Fleming M D, Zimonjic D B, Donaher J L, et al. Human breast cancer cells generated by oncogenic transformation of primary mammary epithelial cells. Genes Dev 2001; 15: 50-65.
12. Orimo A, Gupta P B, Sgroi D C, Arenzana-Seisdedos F, Delaunay T, Naeem R, et al. promote tumor growth and angiogenesis through elevated SDF-1/CXCL12 secretion. Cell 2005; 121: 335-48.
13. Ince T A, Richardson A L, Bell G W, Saitoh M, Godar S, Karnoub A E, et al. Transformation of different human breast epithelial cell types leads to distinct tumor phenotypes. Cancer Cell 2007; 12: 160-70.
14. Rafii S, Lyden D, Benezra R, Hattori K, and Heissig B. Vascular and haematopoietic stem cells: novel targets for anti-angiogenesis therapy? Nat Rev Cancer 2002; 2: 826-35.
15. Gao D and Mittal V. The role of bone-marrow-derived cells in tumor growth, metastasis initiation and progression. Trends Mol Med 2009; 15: 333-43.
16. Naik R P, Jin D, Chuang E, Gold E G, Tousimis E A, Moore A L, et al. Circulating endothelial progenitor cells correlate to stage in patients with invasive breast cancer. Breast Cancer Res Treat 2008; 107: 133-8.
17. Battinelli E M, Markens B A, and Italiano J E, Jr. Release of angiogenesis regulatory proteins from platelet alpha granules: modulation of physiologic and pathologic angiogenesis. Blood 2011; 118: 1359-69.
18. Italiano J E, Jr., Richardson J L, Patel-Hett S, Battinelli E, Zaslaysky A, Short S, et al. Angiogenesis is regulated by a novel mechanism: pro- and antiangiogenic proteins are organized into separate platelet alpha granules and differentially released. Blood 2008; 111: 1227-33.
19. Sabrkhany S, Griffioen A W, and Oude Egbrink M G. The role of blood platelets in tumor angiogenesis. Biochim Biophys Acta 2010; 1815: 189-96.
20. Gay L J and Felding-Habermann B. Contribution of platelets to tumour metastasis. Nat Rev Cancer 2011; 11: 123-34.
21. Al-Ha]] M, Wicha M S, Benito-Hernandez A, Morrison S J, and Clarke M F. Prospective identification of tumorigenic breast cancer cells. Proc Natl Acad Sci USA 2003; 100: 3983-8.
22. Aigner, S., Sthoeger, Z. M., Fogel, M., Weber, E., Zarn, J., Ruppert, M., et al. CD24, a mucin-type glycoprotein, is a ligand for P-selectin on human tumor cells. Blood 1997; 89: 3385-95.
23. Marotta, L. L., Almendro, V., Marusyk, A., Shipitsin, M., Schemme, J., Walker, S. R., et al. The JAK2/STAT3 signaling pathway is required for growth of CD44CD24 stem cell-like breast cancer cells in human tumors. J Clin Invest 2011; 121: 2723-35.
24. Yu H, Pardoll D, and Jove R. STATs in cancer inflammation and immunity: a leading role for STAT3. Nat Rev Cancer 2009; 9: 798-809.
25. Yu H, Kortylewski M, and Pardoll D. Crosstalk between cancer and immune cells: role of STAT3 in the tumour microenvironment. Nat Rev Immunol 2007; 7: 41-51.
26. Farace, F., Gross-Goupil, M., Tournay, E., Taylor, M., Vimond, N., Jacques, N., et al. Levels of circulating CD45(dim)CD34(+)VEGFR2(+) progenitor cells correlate with outcome in metastatic renal cell carcinoma patients treated with tyrosine kinase inhibitors. Br J Cancer 2011; 104: 1144-50.
27. Lee H J, Kim D I, Kwak C, Ku J H, and Moon K C. Expression of CD24 in clear cell renal cell carcinoma and its prognostic significance. Urology 2008; 72: 603-7.
28. Coppinger, J. A., O'Connor, R., Wynne, K., Flanagan, M., Sullivan, M., Maguire, P. B., et al. Moderation of the platelet releasate response by aspirin. Blood 2007; 109: 4786-92.
29. Ruiterkamp J, Ernst M F, van de Poll-Franse L V, Bosscha K, Tjan-Heijnen V C, and Voogd A C. Surgical resection of the primary tumour is associated with improved survival in patients with distant metastatic breast cancer at diagnosis. Eur J Surg Oncol 2009; 35: 1146-51.
30. Park S Y, Lee H E, Li H, Shipitsin M, and Gelman R, Polyak K. Heterogeneity for stem cell-related markers according to tumor subtype and histologic stage in breast cancer. Clin Cancer Res 2010; 16: 876-87.
31. Cao X, Geradts J, Dewhirst M W, and Lo H W. Upregulation of VEGF-A and CD24 gene expression by the tGLI1 transcription factor contributes to the aggressive behavior of breast cancer cells. Oncogene 2012; 31: 104-15.
32. Kristiansen, G., Winzer, K. J., Mayordomo, E., Bellach, J., Schluns, K., Denkert, C., et al. CD24 expression is a new prognostic marker in breast cancer. Clin Cancer Res 2003; 9: 4906-13.
33. Abel E J and Wood C G. Cytoreductive nephrectomy for metastatic RCC in the era of targeted therapy. Nat Rev Urol 2009; 6: 375-83.
34. Aben, K. K., Heskamp, S., Janssen-Heijnen, M. L., Koldewijn, E. L., van Herpen, C. M., Kiemeney, L. A., et al. Better survival in patients with metastasised kidney cancer after nephrectomy: a population-based study in the Netherlands. Eur J Cancer 2011; 47: 2023-32.
35. Almog N. Molecular mechanisms underlying tumor dormancy. Cancer Lett 2010; 294: 139-46.
36. Stone, R. L., Nick, A. M., McNeish, I. A., Balkwill, F., Han, H. D., Bottsford-Miller, J., et al. Paraneoplastic thrombocytosis in ovarian cancer. N Engl J Med 2012; 366: 610-8.
37. Labelle M, Begum S, and Hynes R O. Direct signaling between platelets and cancer cells induces an epithelial-mesenchymal-like transition and promotes metastasis. Cancer Cell 2011; 20: 576-90.
38. Gisterek, I., Matkowski, R., Lacko, A., Sedlaczek, P., Szewczyk, K., Biecek, P., et al. Serum vascular endothelial growth factors a, C and d in human breast tumors. Pathol Oncol Res 2009; 16: 337-44.
39. Peterson, J. E., Zurakowski, D., Italiano, J. E., Jr., Michel, L. V., Connors, S., Oenick, M., et al. VEGF, PF4 and PDGF are elevated in platelets of colorectal cancer patients. Angiogenesis 2012; 15: 265-73.
40. Shojaei F. Anti-angiogenesis therapy in cancer: Current challenges and future perspectives. Cancer Lett 2012; 320: 130-7.
41. Twombly R. Avastin's uncertain future in breast cancer treatment. J Natl Cancer Inst 2011; 103: 458-60.
42. Thun M J, Jacobs E J, and Patrono C. The role of aspirin in cancer prevention. Nat Rev Clin Oncol 2012; 9: 259-67.
43. Bastiaannet, E., Sampieri, K., Dekkers, 0. M., de Craen, A. J., van Herk-Sukel, M. P., Lemmens, V., et al. Use of Aspirin postdiagnosis improves survival for colon cancer patients. Br J Cancer 2012; 106: 1564-70.
44. Lim, W. Y., Chuah, K. L., Eng, P., Leong, S. S., Lim, E., Lim, T. K., et al. Aspirin and non-aspirin non-steroidal anti-inflammatory drug use and risk of lung cancer. Lung Cancer 2012; 77: 246-51.
45. Ni X, Ma J, Zhao Y, Wang Y, and Wang S. Meta-analysis on the association between non-steroidal anti-inflammatory drug use and ovarian cancer. Br J Clin Pharmacol 2012.
46. Rothwell P M, Wilson M, Price J F, Belch J F, Meade T W, and Mehta Z. Effect of daily aspirin on risk of cancer metastasis: a study of incident cancers during randomised controlled trials. Lancet 2012; 379: 1591-601.
47. Thon, J. N., Montalvo, A., Patel-Hett, S., Devine, M. T., Richardson, J. L., Ehrlicher, A., et al. Cytoskeletal mechanics of proplatelet maturation and platelet release. J Cell Biol 2010; 191: 861-74.

TABLE 1

PCR Oligonucleotide Primers, (H: human, M: mouse)

| Name | Sequence | Size amplified | |
|---|---|---|---|
| H-Zeb1 (Pena C et al., 2008) | F: GCCAATAAGCAAACGATTCTG R: TTTGGCTGGATCACTTTCAAG | 100 bp | SEQ ID No. 1 SEQ ID No. 2 |
| H-VIM (Mani et al., 2008) | F: GAGAACTTTGCCGTTGAAGC R: GCTTCCTGTAGGTGGCAATC | 162 bp | SEQ ID No. 3 SEQ ID No. 4 |
| H-OCT4 (Peng S et al., 2010) | F: GTGGAGGAAGCTGACAACAA R: GCCGGTTACAGAACCACACT | 203 bp Transcript 1, 2 or 3 | SEQ ID No. 5 SEQ ID No. 6 |
| H-OCT-4A (Wang Wi et al., 2009) | F: AGCAAAACCCGGAGGAGT R: CCACATCGGCCTGTGTATATC | 113 bp | SEQ ID No. 7 SEQ ID No. 8 |
| H-cMyc (Wang J et al., PlosOne 2008) | F: TCAAGAGGCGAACACACAAC R: GGCCTTTTCATTGTTTTCCA | 109 bp | SEQ ID No. 9 SEQ ID No. 10 |
| H-EGF (Patsialou A. et al., Cancer Research 2009) | F: CAATGCAACCAACTTCATGG R: AAGCTTCGCTCCATTACCTG | 120 bp | SEQ ID No. 11 SEQ ID No. 12 |
| H-IGF1 | F: GTGACATTGCTCTCAACATCTCCCA R: GCGAGGAGGACATGGTGTGCA | 187 bp | SEQ ID No. 13 SEQ ID No. 14 |
| H-GAPDH | F: GAAGGTGAAGGTCGGAGTC R: GAAGATGGTGATGGGATTTC | 225 bp | SEQ ID No. 15 SEQ ID No. 16 |
| H-βactin | F: ACTATGACTTAGTTGCGTTACAC R: GCCATGCCAATCTCATCTTG | 75 bp | SEQ ID No. 17 SEQ ID No. 18 |
| M-EGF (Christopher R et al., 1999) | F: AATAGTTATCCAGGATGCCC R: ACGCAGCTCCCACCATCG TA | 158 bp | SEQ ID No. 19 SEQ ID No. 20 |
| M-IGF1 (Yu S. et al., Prostate 2011) | F: GGTGGATGCTCTTCAGTTC R: TTTGTAGGCTTCAGTGGG | 173 bp | SEQ ID No. 21 SEQ ID No. 22 |
| M-IL6 | F: GCTGGAGTCACAGAAGGAGTGGCT R: GGCATAACGCACTAGGTTTGCCGA | 117 bp | SEQ ID No. 23 SEQ ID No. 24 |
| M-CCL8 | F: AGGCTCCAGTCACCTGCTGCT R: ACCACAGCTTCCATGGGCAC | 109 bp | SEQ ID No. 25 SEQ ID No. 26 |
| M-CXCL1 | F: GAGCTGCGCTGTCAGTGCCT R: CAAGGCAAGCCTCGCGACCA | 142 bp | SEQ ID No. 27 SEQ ID No. 28 |
| M-CSF1R (Patsialou A et al., Cancer Research 2009) | F: TGGTGCACCCCCTAGTTCTCT R: GGCCACTCCTGTGAGCTTAG | 201 bp | SEQ ID No. 29 SEQ ID No. 30 |

TABLE 1-continued

PCR Oligonucleotide Primers, (H: human, M: mouse)

| Name | Sequence | Size amplified | |
|---|---|---|---|
| M-WNT3 | F: TGAGTCCCGAGGCTGGGTGG<br>R: GTCCCTCTCGGTGGGTGGCT | 70 bp | SEQ ID No. 31<br>SEQ ID No. 32 |
| M-IL14 | F: CGGCAGGAGCACCCATCGAC<br>R: GCCCGGCTTGGTTCTCGGTT | 87 bp | SEQ ID No. 33<br>SEQ ID No. 34 |
| M-SPP1 | F: TCGGAGGAAACCAGCCAAGGACT<br>R: AAGCTTCTTCTCCTCTGAGCTGCCA | 129 bp | SEQ ID No. 35<br>SEQ ID No. 36 |
| M-FRZB | F: CCTGAGGCCATCGTCACCGC<br>R: GCAACGTTCGCTGCTTGCCC | 87 bp | SEQ ID No. 37<br>SEQ ID No. 38 |
| M-IGF2<br>(Dong/Myung Shin et al., Leukemia 2009) | F: TGGTCCCAGAGAGGTTTTAGGTGG<br>R: ACTTGCTCCCGCCTGATGTAAC | 222 bp | SEQ ID No. 39<br>SEQ ID No. 40 |
| M-βactin<br>(Ohtani et al., PNAS 2007) | F: GTATGGAATCCTGTGGCATC<br>R: AAGCACTTGCGGTGCACGAT | 283 bp | SEQ ID No. 41<br>SEQ ID No. 42 |
| M-GAPDH | F: GGTGAAGGTCGGTGTGAACG<br>R: CTCGCTCCTGGAAGATGGTG | 233 bp | SEQ ID No. 43<br>SEQ ID No. 44 |

TABLE 2

Antibodies

Specific Antibodies for Immunofluorescence

| Antibody | Dilution | Company |
|---|---|---|
| Rabbit polyclonal anti-GFP | 1:1000 | Abcam (ab290) |
| Rabbit polyclonal anti-Oct4 | 1:100 | Chemicon AB3209 |
| Rabbit polyclonal anti-ZEB1 | 1:50 | Santa Cruz sc-25388 |
| Mouse monoclonal anti-CK14 | 1:20 | Leica (NCL-L-LL002) |
| Rabbit polyclonal anti-CK18 | 1:100 | Abcam (ab32118) |
| Rabbit polyclonal anti-Ki67 | 1:200 | Thermo scientific (9106) |
| Mouse monoclonal anti-SMA | 1:50 | Vector (VP-S281) |
| Mouse monoclonal anti-SV40 LgT | 1:75 | Santa cruz (sc-147) |
| Mouse monoclonal anti-c-myc | 1:100 | Millipore (MAB 8864) |
| P-IGFR/IR | 1:50 | Abcam (ab39398) |
| P-EGFR | 1:600 | Cell Signaling (3777) |
| Alexa Fluor 488 goat anti-mouse | 1:200 | Invitrogen (A11001) |
| Alexa Fluor 594 goat anti-rabbit | 1:200 | Invitrogen (A11012) |
| Alexa Fluor 647 goat anti-rat | 1:200 | Invitrogen (A21247) |

Specific Antibodies for FACS

| Antibody | Dilution/Concentration | Company |
|---|---|---|
| CD16/CD32 F$_c$γ III/II receptor | 250 ng/10$^6$ cells | BD Pharmingen |
| APC-humanIGF1R (clone147) | 1:20 | eBiosciences |
| PE-humanEGFR | 1:20 | BD Pharmingen |

TABLE 3

List of genes or proteins.

| List of Gene | Cancer type | Genes that upregulate | Activation | Genes that downregulate | Genes that are mutated |
|---|---|---|---|---|---|
| IL6 | Non-small cell lung cancer, ovarian cancer, breast cancer, prostate cancer, pancreatic cancer, multiple mieloma, colorectal cancer | x | | | x |
| IL1 beta | pancreatic cancer, colorectal cancer, lung cancer, ovarian cancer, prostate cancer, breast cancer | x | | | x |
| TNFalpha | Colorectal cancer, breast cancer, gastric cancer, cervical cancer | | | | x |
| EGFR | Cervical cancer, colorectal cancer, lung cancer, breast cancer, urothelial cell carcinoma | | x | | x |

TABLE 3-continued

List of genes or proteins.

| List of Gene | Cancer type | Genes that upregulate | Activation | Genes that downregulate | Genes that are mutated |
|---|---|---|---|---|---|
| IGF1R | Myeloma, breast cancer | | x | | |
| Oct-04 | Breast cancer, nasopharyngeal carcinoma, ovarian cancer, neuroendocrine tumors of the ileum | x | | | |
| cMyc | Breast cancer, ovarian cancer, B-cell lymphomas | x | | | x |
| NANOG | Ovarian cancer | x | | | |
| SOX2 | nasopharyngeal carcinoma | | | | |
| LIF | Melanoma | x | | | |
| PI3K | Prostate cancer, cervical cancer, B-cell lymphomas; urothelial cell carcinoma, breast cancer, clear-cell renal cell carcinoma | | x | | x |
| mTOR | nasopharyngeal carcinoma, B-cell lymphomas, clear-cell renal cell carcinoma | x | x | | x |
| P-AKT | Myeloma, urothelial cell carcinoma; clear-cell renal cell carcinoma | | x | | x |
| NFKbeta | Leukemia, lung adenocarcinoma | | x | | |
| ZEB1 | Breast cancer, endometrial carcinoma | x | | | |
| Twist | Endometrial cancer, prostate cancer, pancreatic cancer, breast cancer, cutaneous squamous cell carcinomas | x | | | |
| Vimentin | Pancreatic cancer, urothelial cell carcinoma | x | | | |
| E-cadherin | Breast cancer, prostate cancer, squamous cell lung carcinoma, endometrial carcinoma, melanoma, hepatocellular carcinoma | | | x | |
| TGFbeta | Prostate cancer, breast cancer | x | | | |
| Slug | Endometrial carcinoma | x | | | |
| Sox2 | Nasopharyngeal carcinoma, pancreatic cancer, gastric cancer | x | | | |
| Snail | Prostate cancer, breast cancer, melanoma | x | | | |
| PTEN | Melanoma, colorectal cancer | | | x | x |
| p53 | Lung cancer, clear-cell renal cell carcinoma | | | x | x |
| K-Ras | Colorectal cancer, lung cancer | | | | x |
| MMP9 | Hepatocellular carcinoma, breast cancer | x | | | |
| B-catenin | Urothelial cell carcinoma | x | | | |
| Wnt3A | Breast cancer | | | | |
| CD44 | Gastric cancer, breast cancer, pancreatic cancer | x | | | |
| CD24 | Breast Cancer | | | | |
| CD133 | Nasopharyngeal carcinoma, gastric cancer, pancreatic cancer | x | | | |
| ALDH1 | Pancreatic cancer, breast cancer | x | | | |
| Nestin | | | | | |
| Tenascin C | | | | | |
| Osteopontin | Breast cancer | x | | | |
| HGF | | | | | |
| FGF | Colorectal cancer | x | | | |
| EGF | Cervical cancer, breast cancer | x | | | |
| IGF-1 | Myeloma, prostate cancer, pancreatic adenocarcinoma, breast cancer | x | | | |
| Phospho-MAPK | Myeloma, cervical cancer | | x | | |
| claudin | | | | X | |
| HER2 | breast cancer | x | | | x |

TABLE 4

The 17-signature associated with metastasis.

| Gene | Gene name | GenBank ID |
|---|---|---|
| *Upregulated in metastases* | | |
| SNRPF | Small nuclear ribonucleoprotein F | AI032612 |
| EIF4EL3 | Elongation initiation factor 4E-like 3 | AF038957 |
| HNRPAB | Heterogeneous nuclear ribonucleoprotein A/B | M65028 |
| DHPS | Deoxyhypusine synthase | U79262 |
| PTTG1 | Securin | AA203476 |
| COL1A1 | Type 1 collagen, α1 | Y15915 |
| COL1A2 | Type 1 collagen, α2 | J03464 |
| LMNB1 | Lamin B1 | L37747 |
| *Downregulated in metastases* | | |
| ACTG2 | Actin, γ2 | D00654 |
| MYLK | Myosin light chain kinase | U48959 |
| MYH11 | Myosin, heavy chain 11 | AF001548 |
| CNN1 | Calponin 1 | D17408 |
| HLA-DPB1 | MHC Class II, DPβ1 | M83664 |
| RUNX1 | Runt-related transcription factor 1 | D43969 |
| MT3 | Metallothionein 3 | S72043 |
| NR4A1 | Nuclear hormone receptor TR3 | L13740 |
| RBM5 | RNA binding motif 5 | AF091263 |

TABLE 5

List of genes or proteins that correlate negatively or positively with cancer malignant state. Van't Veer et al. Nature, 2002, 451: 530-535

| accession # | correlation | gene name | description |
|---|---|---|---|
| NM_003748 | 0.420671 | ALDH4 | aldehyde dehydrogenase 4 (glutamate gamma-semialdehyde dehydrogenase; pyrroline-5-carboxylate dehydrogenase) |
| NM_003862 | 0.410964 | FGF18 | fibroblast growth factor 18 |
| Contig32125_RC | 0.409054 | | ESTs |
| U82987 | 0.407002 | BBC3 | Bcl-2 binding component 3 |
| AB037863 | 0.402335 | KIAA1442 | KIAA1442 protein |
| NM_020974 | 0.399987 | CEGP1 | CEGP1 protein |
| Contig55377_RC | 0.3906 | | ESTs |
| NM_003882 | 0.384479 | WISP1 | WNT1 inducible signaling pathway protein 1 |
| NM_000849 | 0.380831 | GSTM3 | glutathione S-transferase M3 (brain) |
| Contig48328_RC | 0.375252 | | ESTs, Weakly similar to T17248 hypothetical protein DKFZp586G1 122.1 [*H. sapiens*] |
| Contig46223_RC | 0.374289 | | ESTs |
| NM_006117 | 0.37329 | PECI | peroxisomal D3,D2-enoyl-CoA isomerase |
| NM_003239 | 0.371524 | TGFB3 | transforming growth factor, beta 3 |
| NM_018401 | 0.368349 | HSA250839 | gene for serine/threonine protein kinase |
| AF257175 | 0.3659 | | *Homo sapiens* hepatocellular carcinoma-associated antigen 64 (HCA64) mRNA, complete cds |
| AF201951 | 0.363953 | CFFM4 | high affinity immunoglobulin epsilon receptor beta subunit |
| NM_001282 | 0.363326 | AP2B1 | adaptor-related protein complex 2, beta 1 subunit |
| Contig63102_RC | 0.359255 | FLJ11354 | hypothetical protein FLJ11354 |
| NM_000286 | 0.355105 | PEX12 | peroxisomal biogenesis factor 12 |
| Contig34634_RC | 0.350892 | GCN1L1 | GCN1 (general control of amino-acid synthesis 1, yeast)-like 1 |
| NM_000320 | 0.350505 | QDPR | quinoid dihydropteridine reductase |
| AB033007 | 0.35035 | KIAA1181 | KIAA1181 protein |
| AL355708 | 0.349459 | | *Homo sapiens* mRNA full length insert cDNA clone EUROIMAGE 44260 |
| NM_000017 | 0.348527 | ACADS | acyl-Coenzyme A dehydrogenase, C-2 to C-3 short chain |
| NM_006763 | 0.345013 | BTG2 | BTG family, member 2 |
| AF148505 | 0.344597 | MMSDH | methylmalonate-semialdehyde dehydrogenase |
| Contig57595 | 0.343518 | | ESTs |
| NM_001280 | 0.34211 | CIRBP | cold inducible RNA-binding protein |
| AJ224741 | 0.337959 | MATN3 | matrilin 3 |
| U45975 | 0.336027 | PIB5PA | phosphatidylinositol (4,5) bisphosphate 5-phosphatase, A |
| Contig49670_RC | 0.335911 | | *Homo sapiens* cDNA: FLJ23228 fis, clone CAE06654 |
| Contig753_RC | 0.335828 | | ESTs |
| Contig25055_RC | 0.333901 | | ESTs, Weakly similar to DWHUT L-serine dehydratase [*H. sapiens*] |
| Contig53646_RC | 0.333838 | | ESTs |
| Contig42421_RC | 0.332726 | | ESTs, Weakly similar to unnamed protein product [*H. sapiens*] |
| Contig51749_RC | 0.332572 | RAI2 | retinoic acid induced 2 |
| AL137514 | 0.33157 | | *Homo sapiens* mRNA; cDNA DKFZp564L0678 (from clone DKFZp564L0678) |
| NM_004911 | 0.330593 | ERP70 | protein disulfide isomerase related protein (calcium-binding protein, intestinal- |
| NM_000224 | 0.329843 | KRT18 | keratin 18 |
| NM_013262 | 0.327746 | MIR | myosin regulatory light chain interacting protein |
| Contig41887_RC | 0.327671 | | ESTs, Weakly similar to Homolog of rat Zymogen granule membrane protein [*H. sapiens*] |
| NM_004163 | 0.327549 | RAB27B | RAB27B, member RAS oncogene family |
| AB020689 | 0.327146 | KIAA0882 | KIAA0882 protein |
| NM_015416 | 0.326658 | DKFZP586A011 | DKFZP586A011 protein |
| Contig43747_RC | 0.326592 | | ESTs |
| NM_012429 | 0.325185 | SEC14L2 | SEC14 (S. cerevisiae)-like 2 |
| AB033043 | 0.322738 | DKFZP761L0424 | hypothetical protein DKFZp761L0424 |
| AL133619 | 0.322487 | | *Homo sapiens* mRNA; cDNA DKFZp434E2321 (from clone DKFZp434E2321); partial cds |
| NM_016569 | 0.321978 | TBX3-iso | TBX3-iso protein |
| NM_004480 | 0.318701 | FUT8 | fucosyltransferase 8 (alpha (1,6)fucosyltransferase) |
| NM_004798 | 0.318314 | KIF3B | kinesin family member 3B |

TABLE 5-continued

List of genes or proteins that correlate negatively or positively with cancer malignant state. Van't Veer et al. Nature, 2002, 451: 530-535

| accession # | correlation | gene name | description |
| --- | --- | --- | --- |
| Contig37063_RC | 0.316439 | | ESTs |
| NM_000507 | 0.316439 | FBP1 | fructose-1,6-bisphosphatase 1 |
| AB037745 | 0.316433 | KIAA1324 | KIAA1324 protein |
| Contig50802_RC | 0.314566 | | ESTs |
| NM_001007 | 0.314244 | RPS4X | ribosomal protein S4, x-linked |
| Contig53742_RC | 0.312734 | | ESTs |
| NM_018104 | 0.31192 | FLJ10474 | hypothetical protein FLJ10474 |
| Contig51963 | 0.311766 | MGC2827 | hypothetical protein MGC2827 |
| Contig53268_RC | 0.309868 | FLJ12150 | hypothetical protein FLJ12150 |
| NM_012261 | 0.309834 | HS1119D91 | similar to S68401 (cattle) glucose induced gene |
| NM_020244 | 0.309523 | LOC56994 | cholinephosphotransferase 1 |
| Contig55813_RC | 0.308283 | | ESTs, Moderately similar to hypothetical protein [*H. sapiens*] |
| Contig27312_RC | 0.307881 | | ESTs |
| Contig44064_RC | 0.307246 | | ESTs |
| NM_002570 | 0.307121 | PACE4 | paired basic amino acid cleaving system 4 |
| NM_002900 | 0.306855 | RBP3 | retinol-binding protein 3, interstitial |
| AL050090 | 0.306113 | DKFZP586F1018 | DKFZP586F1018 protein |
| NM_015417 | 0.305725 | DKFZP434I114 | DKFZP434I114 protein |
| Contig47405_RC | 0.304337 | | ESTs |
| NM_016337 | 0.303423 | RNB6 | RNB6 |
| Contig55829_RC | 0.303133 | | ESTs, Weakly similar to cDNA EST EMBL: D75782 comes from this gene |
| Contig37598 | 0.302795 | MMSDH | methylmalonate-semialdehyde dehydrogenase |
| Contig45347_RC | 0.300785 | KIAA1683 | KIAA1683 protein |
| NM_020675 | −0.300019 | AD024 | AD024 protein |
| NM_003234 | −0.300316 | TFRC | transferrin receptor (p90, CD71) |
| AL080110 | −0.300519 | | *Homo sapiens* mRNA; cDNA DKFZp586G1922 (from clone DKFZp586G1922) |
| AL137295 | −0.300887 | | *Homo sapiens* mRNA; cDNA DKFZp434M2216 (from clone DKFZp434M2216) |
| Contig17359_RC | −0.301147 | | ESTs, Weakly similar to S72481 probable transposase [*H. sapiens*] |
| NM_013296 | −0.301291 | HSU54999 | LGN protein |
| NM_019013 | −0.301444 | FLJ10156 | hypothetical protein |
| AF052159 | −0.301473 | | *Homo sapiens* clone 24416 mRNA sequence |
| Contig55313_RC | −0.302308 | | ESTs |
| NM_002358 | −0.30251 | MAD2L1 | MAD2 (mitotic arrest deficient, yeast, homolog)-like 1 |
| NM_004358 | −0.303113 | CDC25B | cell division cycle 25B |
| Contig50106_RC | −0.304123 | | *Homo sapiens* mRNA for KIAA1708 protein, partial cds |
| NM_005342 | −0.30429 | HMG4 | high-mobility group (nonhistone chromosomal) protein 4 |
| NM_014754 | −0.306887 | PTDSS1 | phosphatidylserine synthase 1 |
| U58033 | −0.306994 | MTMR2 | myotubularin related protein 2 |
| Contig64688 | −0.307043 | FLJ23468 | hypothetical protein FLJ23468 |
| NM_001827 | −0.308101 | CKS2 | CDC28 protein kinase 2 |
| Contig3902_RC | −0.308255 | | Human DNA sequence from clone RP5-858B6 on chromosome 1q42. 13-43 Contains ESTs, STSs, GSSs and a CpG island. Contains three novel genes |
| Contig41413_RC | −0.308372 | RRM2 | ribonucleotide reductase M2 polypeptide |
| NM_015434 | −0.308773 | DKFZP434B168 | DKFZP434B168 protein |
| NM_014078 | −0.308816 | L13 | L13 protein |
| NM_018120 | −0.309766 | FLJ10511 | hypothetical protein FLJ10511 |
| NM_001124 | −0.309959 | ADM | adrenomedullin |
| L27560 | −0.312261 | | Human insulin-like growth factor binding protein 5 (IGFBP5) mRNA |
| Contig45816_RC | −0.312313 | | ESTs |
| AL050021 | −0.312792 | | *Homo sapiens* mRNA; cDNA DKFZp564D016 (from clone DKFZp564D016) |
| NM_006115 | −0.312978 | PRAME | preferentially expressed antigen in melanoma |
| NM_001333 | −0.3143 | CTSL2 | cathepsin L2 |
| NM_005496 | −0.314665 | SMC4L1 | SMC4 (structural maintenance of chromosomes 4, yeast)-like 1 |
| Contig51519_RC | −0.315998 | | ESTs |
| Contig1778_RC | −0.316409 | | ESTs |
| NM_014363 | −0.316504 | SACS | spastic ataxia of Charlevoix-Saguenay (sacsin) |
| NM_001905 | −0.316985 | CTPS | CTP synthase |
| NM_018454 | −0.317076 | BM037 | uncharacterized bone marrow protein BM037 |
| NM_002811 | −0.317445 | PSMD7 | proteasome (prosome, macropain) 26S subunit, non-ATPase, 7 (Mov34 homolog) |
| NM_004603 | −0.317755 | STX1A | syntaxin 1A (brain) |
| AB032973 | −0.318432 | LCHN | LCHN protein |
| NM_006096 | −0.318612 | NDRG1 | N-myc downstream regulated |
| D25328 | −0.318951 | PFKP | phosphofructokinase, platelet |
| Contig46802_RC | −0.319329 | | *Homo sapiens* scavenger receptor cysteine-rich type 1 protein M160 precursor, mRNA, complete cds, alternatively spliced |
| X94232 | −0.319413 | MAPRE2 | microtubule-associated protein, RP/EB family, member 2 |
| NM_018004 | −0.320034 | FLJ10134 | hypothetical protein FLJ10134 |
| Contig8581_RC | −0.320433 | | ESTs |
| Contig55188_RC | −0.320483 | FLJ22341 | hypothetical protein FLJ22341 |
| Contig50410 | −0.32152 | | *Homo sapiens* mRNA; cDNA DKFZp586J0720 (from clone DKFZp586J0720) |
| Contig53226_RC | −0.321716 | | ESTs |
| NM_012214 | −0.321864 | MGAT4A | mannosyl (alpha-1,3-)-glycoprotein beta-1,4-N-acetylglucosaminyltransferase, isoenzyme A |
| NM_006201 | −0.322398 | PCTK1 | PCTAIRE protein kinase 1 |
| NM_006372 | −0.322482 | NSAP1 | NS1-associated protein 1 |
| Contig13480_RC | −0.322679 | | ESTs |

TABLE 5-continued

List of genes or proteins that correlate negatively or positively with cancer malignant state. Van't Veer et al. Nature, 2002, 451: 530-535

| accession # | correlation | gene name | description |
| --- | --- | --- | --- |
| AL137502 | −0.323276 | DKFZP761H171 | hypothetical GTP-binding protein DKFZp761H171 |
| Contig40128_RC | −0.323586 | | ESTs |
| NM_003676 | −0.323889 | DEGS | degenerative spermatocyte (homolog *Drosophila*; lipid desaturase) |
| NM_013437 | −0.32456 | ST7 | potential tumor suppressor |
| Contig2504_RC | −0.324997 | | ESTs |
| AL133603 | −0.325006 | | *Homo sapiens* mRNA; cDNA DKFZp434E1515 (from clone DKFZp434E1515) |
| NM_012177 | −0.325709 | FBXO5 | F-box only protein 5 |
| R70506_RC | −0.325832 | | *Homo sapiens* sprouty-4C mRNA, complete cds |
| NM_003662 | −0.326725 | PIR | Pirin |
| NM_018136 | −0.327067 | FLJ10549 | hypothetical protein FLJ 10549 |
| NM_000158 | −0.327818 | GBE1 | glucan (1,4-alpha-), branching enzyme 1 (glycogen branching enzyme, Andersen disease, glycogen storage disease type IV) |
| NM_018410 | −0.327831 | DKFZp762E1312 | hypothetical protein DKFZp762E1312 |
| Contig21812_RC | −0.32832 | FLJ21924 | hypothetical protein FLJ21924 |
| NM_004052 | −0.329067 | BNIP3 | BCL2/adenovirus E1B 19 kD-interacting protein 3 |
| Contig4595 | −0.329257 | | ESTs, Weakly similar to weak similarity to collagens [*C. elegans*] |
| Contig60864_RC | −0.329699 | | ESTs |
| NM_003878 | −0.330329 | GGH | gamma-glutamyl hydrolase (conjugase, folylpolygammaglutamyl hydrolase) |
| U96131 | −0.330572 | TRIP13 | thyroid hormone receptor interactor 13 |
| NM_005563 | −0.330573 | LAP18 | leukemia-associated phosphoprotein p18 (stathmin) |
| NM_018455 | −0.331027 | BM039 | uncharacterized bone marrow protein BM039 |
| Contig44799_RC | −0.331595 | | ESTs |
| NM_003258 | −0.332658 | TK1 | thymidine kinase 1, soluble |
| NM_004456 | −0.332666 | EZH2 | enhancer of zeste (*Drosophila*) homolog 2 |
| NM_003158 | −0.332698 | STK6 | serine/threonine kinase 6 |
| NM_014750 | −0.332765 | KIAA0008 | KIAA0008 gene product |
| Contig25343_RC | −0.33287 | | ESTs |
| NM_005196 | −0.333427 | CENPF | centromere protein F (350/400 kD, mitosin) |
| Contig57864_RC | −0.333585 | | ESTs |
| NM_014109 | −0.333637 | PRO2000 | PRO2000 protein |
| NM_002808 | −0.334053 | PSMD2 | proteasome (prosome, macropain) 26S subunit, non-ATPase, 2 |
| Contig58368_RC | −0.334201 | LOC56901 | NADH: ubiquinone oxidoreductase MLRQ subunit homolog |
| Contig46653_RC | −0.335042 | | ESTs |
| NM_004504 | −0.335652 | HRB | HIV-1 Rev binding protein |
| M21551 | −0.336781 | NMB | neuromedin B |
| NM_014875 | −0.337104 | KIAA0042 | KIAA0042 gene product |
| NM_001168 | −0.338128 | BIRC5 | baculoviral IAP repeat-containing 5 (survivin) |
| NM_003376 | −0.338866 | VEGF | vascular endothelial growth factor |
| NM_018098 | −0.339792 | FLJ10461 | hypothetical protein FLJ10461 |
| AF161553 | −0.341001 | NS1-BP | NS1-binding protein |
| NM_020166 | −0.342723 | MCCC1 | methylcrotonoyl-Coenzyme A carboxylase 1 (alpha) |
| NM_017779 | −0.342905 | FLJ20354 | hypothetical protein FLJ20354 |
| NM_018265 | −0.344069 | FLJ10901 | hypothetical protein FLJ10901 |
| AF155117 | −0.344538 | | *Homo sapiens* NY-REN-62 antigen mRNA, partial cds |
| NM_004701 | −0.346075 | CCNB2 | cyclin B2 |
| NM_006281 | −0.347976 | STK3 | serine/threonine kinase 3 (Ste20, yeast homolog) |
| Contig44289_RC | −0.34813 | | ESTs |
| NM_004336 | −0.34954 | BUB1 | budding uninhibited by benzimidazoles 1 (yeast homolog) |
| Contig33814_RC | −0.349802 | | ESTs |
| NM_003600 | −0.352033 | STK15 | serine/threonine kinase 15 |
| NM_006265 | −0.352035 | RAD21 | RAD21 (S. pombe) homolog |
| NM_000291 | −0.352119 | PGK1 | phosphoglycerate kinase 1 |
| NM_000096 | −0.35245 | CP | ceruloplasmin (ferroxidase) |
| NM_001673 | −0.352502 | ASNS | asparagine synthetase |
| NM_001216 | −0.353255 | CA9 | carbonic anhydrase IX |
| NM_014968 | −0.354256 | KIAA1104 | KIAA1104 protein |
| NM_018354 | −0.356001 | FLJ11190 | hypothetical protein FLJ11190 |
| NM_007036 | −0.356542 | ESM1 | endothelial cell-specific molecule 1 |
| NM_004702 | −0.356595 | CCNE2 | cyclin E2 |
| Contig2399_RC | −0.356602 | SM-20 | similar to rat smooth muscle protein SM-20 |
| NM_001809 | −0.357716 | CENPA | centromere protein A (17 kD) |
| Contig20217_RC | −0.357877 | | ESTs |
| NM_003981 | −0.358259 | PRC1 | protein regulator of cytokinesis 1 |
| NM_007203 | −0.359573 | AKAP2 | A kinase (PRKA) anchor protein 2 |
| NM_006681 | −0.359698 | NMU | neuromedin U |
| AF055033 | −0.359944 | IGFBP5 | insulin-like growth factor binding protein 5 |
| NM_014889 | −0.360044 | MP1 | metalloprotease 1 (pitrilysin family) |
| NM_020386 | −0.360778 | LOC57110 | H-REV107 protein-related protein |
| NM_000599 | −0.361285 | IGFBP5 | insulin-like growth factor binding protein 5 |
| Contig56457_RC | −0.361645 | TMEFF1 | transmembrane protein with EGF-like and two follistatin-like domains 1 |
| NM_005915 | −0.363852 | MCM6 | minichromosome maintenance deficient (mis5, S. pombe) 6 |
| Contig24252_RC | −0.364986 | | ESTs |
| Contig55725_RC | −0.365347 | | ESTs, Moderately similar to T50635 hypothetical protein DKFZp762L0311.1 |
| NM_002916 | −0.365585 | RFC4 | replication factor C (activator 1) 4 (37 kD) |
| NM_014321 | −0.365812 | ORC6L | origin recognition complex, subunit 6 (yeast homolog)-like |
| NM_006931 | −0.366486 | SLC2A3 | solute carrier family 2 (facilitated glucose transporter), member 3 |

TABLE 5-continued

List of genes or proteins that correlate negatively or positively with cancer malignant state. Van't Veer et al. Nature, 2002, 451: 530-535

| accession # | correlation | gene name | description |
|---|---|---|---|
| AL080079 | −0.367388 | DKFZP564D0462 | hypothetical protein DKFZp564D0462 |
| Contig51464_RC | −0.367446 | FLJ22477 | hypothetical protein FLJ22477 |
| NM_000788 | −0.367698 | DCK | deoxycytidine kinase |
| NM_016448 | −0.369416 | L2DTL | L2DTL protein |
| X05610 | −0.370857 | COL4A2 | collagen, type IV, alpha 2 |
| NM_014791 | −0.370858 | KIAA0175 | KIAA0175 gene product |
| Contig40831_RC | −0.372931 | | ESTs |
| AK000745 | −0.373061 | | *Homo sapiens* cDNA FLJ20738 fis, clone HEP08257 |
| NM_015984 | −0.373876 | UCH37 | ubiquitin C-terminal hydrolase UCH37 |
| NM_016577 | −0.376227 | RAB6B | RAB6B, member RAS oncogene family |
| Contig32185_RC | −0.379169 | | *Homo sapiens* cDNA FLJ 13997 fis, clone Y79AA1002220 |
| AF052162 | −0.380834 | FLJ12443 | hypothetical protein FLJ12443 |
| AF073519 | −0.38334 | SERF1A | small EDRK-rich factor 1A (telomeric) |
| NM_003607 | −0.384392 | PK428 | Ser-Thr protein kinase related to the myotonic dystrophy protein kinase |
| NM_006101 | −0.385893 | HEC | highly expressed in cancer, rich in leucine heptad repeats |
| NM_003875 | −0.386515 | GMPS | guanine monphosphate synthetase |
| Contig25991 | −0.390367 | ECT2 | epithelial cell transforming sequence 2 oncogene |
| Contig35251_RC | −0.390407 | | *Homo sapiens* cDNA: FLJ22719 fis, clone HSI14307 |
| NM_004994 | −0.391694 | MMP9 | matrix metalloproteinase 9 (gelatinase B, 92 kD gelatinase, 92 kD type IV |
| NM_000436 | −0.392119 | OXCT | 3-oxoacid CoA transferase |
| NM_002073 | −0.395461 | GNAZ | guanine nucleotide binding protein (G protein), alpha z polypeptide |
| NM_002019 | −0.398066 | FLT1 | fms-related tyrosine kinase 1 (vascular endothelial growth factor/vascular permeability factor receptor) |
| NM_000127 | −0.399515 | EXT1 | exostoses (multiple) 1 |
| NM_020188 | −0.400072 | DC13 | DC13 protein |
| AL137718 | −0.404979 | | *Homo sapiens* mRNA; cDNA DKFZp434C0931 (from clone DKFZp434C0931); partial cds |
| Contig28552_RC | −0.409259 | | *Homo sapiens* mRNA; cDNA DKFZp434C0931 (from clone DKFZp434C0931); partial cds |
| Contig38288_RC | −0.414971 | | ESTs, Weakly similar to ISHUSS protein disulfide-isomerase [*H. sapiens*] |
| AA555029_RC | −0.424122 | | ESTs |
| NM_016359 | −0.424927 | LOC51203 | clone HQ0310 PRO0310p1 |
| Contig46218_RC | −0.432539 | | ESTs |
| Contig63649_RC | −0.468129 | | ESTs |
| AL080059 | −0.527145 | | *Homo sapiens* mRNA for KIAA1750 protein, partial cds |

What is claimed:

1. An assay comprising
in vitro co-culturing a population of cancer responder cells with a population of non-tumor cells in the presence of plasma or platelets or exosomes, wherein the non-tumor cells are selected from the group consisting of bone marrow-derived circulating cells, buffy coat cells, peripheral circulating cells, and immune cells; and
measuring for at least one malignant phenotype exhibited by the cancer responder cells;
wherein at least one of (1) the population of cancer responder cells, (2) the population of non-tumor cells or (3) plasma, platelets, or exosomes is patient-derived and at least one of (1), (2) or (3) are standard positive plasma, platelets, exosomes or cell populations known to provide a tumor supportive environment.

2. The assay of claim 1, wherein the cancer responder cells are selected from a group consisting of defined cancer responder cell lines, primary cancer/tumor cells, or circulating cancer cells.

3. The assay of claim 1, wherein the at least one malignant phenotype measured is selected from the group consisting of the ability to proliferate on soft agar, the ability to proliferate and form a tumor in vitro, the ability to proliferate and form a tumor in vivo, the expression of malignancy markers, and the expression of cancer stem cell markers.

4. The assay of claim 1, further comprising co-culturing the populations of responder cells and non-tumor cells with a population of fibroblast cells.

5. The assay of claim 4, wherein the population of fibroblast cells is obtained from a healthy, cancer-free tissue from a subject.

6. The assay of claim 4, wherein the population of fibroblast cells is obtained from a cancer tumor tissue excised from a subject.

7. The assay of claim 4, wherein the population of fibroblast cells is separated by a membrane from the population of cancer responder cells and the population of non-tumor cells in the co-culture.

8. The assay of claim 1, further comprising contacting the co-culture with at least a test agent or compound.

9. The assay of claim 1, wherein the population of cancer responder cells are selected from HME, HMLE, HMLER hygro-H-rasV12 (HMLER-HR), HMLER-puro-H rasV12, BPE, BPLER, BT-549, and MCF7, MCF7-Ras human breast tumor cells.

10. The assay of claim 1, wherein the cancer responder cells are in an indolent state.

11. The assay of claim 1, wherein the malignant phenotype exhibited by the cancer responder cells is an increase in expression of Oct4, Oct4A, c-Myc, Zeb1, osteopontin, epidermal growth factor receptor (EGFR) and insulin-like growth factor 1 receptor (IGF-1R), or there is
an increase in CD44hi+/CD24low− cells.

12. The assay of claim 1, wherein the malignant phenotype exhibited by the cancer responder cells is an increase in expression of CD24, or an increase in CD44hi+/CD24low− cells.

13. The assay of claim 1, wherein the non-tumor cells are obtained from a bone marrow aspirate, a bone marrow biopsy, a spleen biopsy, a blood sample, a lymph node aspirate or biopsy or resection, or a non-tumor portion of a cancer from a patient.

* * * * *

UNITED STATES PATENT AND TRADEMARK OFFICE
CERTIFICATE OF CORRECTION

| | |
|---|---|
| PATENT NO. | : 10,295,530 B2 |
| APPLICATION NO. | : 14/424948 |
| DATED | : May 21, 2019 |
| INVENTOR(S) | : McAllister et al. |

It is certified that error appears in the above-identified patent and that said Letters Patent is hereby corrected as shown below:

In the Specification

At Column 1, Line 16:
Insert the following heading and paragraph:
--GOVERNMENT SUPPORT
This invention was made with government support under CA166284 awarded by the National Institutes of Health. The government has certain rights in the invention.--

Signed and Sealed this
Second Day of May, 2023

Katherine Kelly Vidal
Director of the United States Patent and Trademark Office

SEQUENCE LISTING

<160> NUMBER OF SEQ ID NOS: 44

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gccaataagc aaacgattct g                                           21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tttggctgga tcactttcaa g                                           21

<210> SEQ ID NO 3
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 3
gagaactttg ccgttgaagc                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcttcctgta ggtggcaatc                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtggaggaag ctgacaacaa                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gccggttaca gaaccacact                                              20

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agcaaaaccc ggaggagt                                                18

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccacatcggc ctgtgtatat c                                            21

<210> SEQ ID NO 9
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 9
tcaagaggcg aacacacaac                                                     20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggccttttca ttgttttcca                                                     20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caatgcaacc aacttcatgg                                                     20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aagcttcgct ccattacctg                                                     20

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtgacattgc tctcaacatc tccca                                               25

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcgaggagga catggtgtgc a                                                   21

<210> SEQ ID NO 15
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 15
gaaggtgaag gtcggagtc                                              19

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gaagatggtg atgggatttc                                             20

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
actatgactt agttgcgtta cac                                         23

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gccatgccaa tctcatcttg                                             20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aatagttatc caggatgccc                                             20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acgcagctcc caccatcgta                                             20

<210> SEQ ID NO 21
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 21
ggtggatgct cttcagttc                                                    19

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tttgtaggct tcagtggg                                                     18

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gctggagtca cagaaggagt ggct                                              24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggcataacgc actaggtttg ccga                                              24

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aggctccagt cacctgctgc t                                                 21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
accacagctt ccatggggca c                                                 21

<210> SEQ ID NO 27
<211> LENGTH: 20
<212> TYPE: DNA
<213> ORGANISM: Artificial Sequence
```

<220> FEATURE:
<223> OTHER INFORMATION: Description of Artificial Sequence: Synthetic primer

<400> SEQUENCE: 27
gagctgcgct gtcagtgcct                                               20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
caaggcaagc ctcgcgacca                                               20

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
tggtgcaccc cctagttctc t                                             21

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
ggccactcct gtgagcttag                                               20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
tgagtcccga ggctgggtgg                                               20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
gtccctctcg gtgggtggct                                               20

<210> SEQ ID NO 33
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 33
cggcaggagc acccatcgac                                                    20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gcccggcttg gttctcggtt                                                    20

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tcggaggaaa ccagccaagg act                                                23

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
aagcttcttc tcctctgagc tgcca                                              25

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cctgaggcca tcgtcaccgc                                                    20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gcaacgttcg ctgcttgccc                                                    20

<210> SEQ ID NO 39
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 39
tggtcccaga gaggttttag gtgg                                              24

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
acttgctccc gcctgatgta ac                                                22

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gtatggaatc ctgtggcatc                                                   20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aagcacttgc ggtgcacgat                                                   20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ggtgaaggtc ggtgtgaacg                                                   20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ctcgctcctg gaagatggtg                                                   20
```